US008329882B2

(12) United States Patent
Smolke et al.

(10) Patent No.: US 8,329,882 B2
(45) Date of Patent: Dec. 11, 2012

(54) GENETIC CONTROL OF MAMMALIAN CELLS WITH SYNTHETIC RNA REGULATORY SYSTEMS

(75) Inventors: Christina D. Smolke, Stanford, CA (US); Yvonne Y. Chen, Pasadena, CA (US); Michael C. Jensen, Sierra Madre, CA (US)

(73) Assignees: California Institute of Technology, Pasadena, CA (US); City of Hope, Duarte, CA (US)

( * ) Notice: Subject to any disclaimer, the term of this patent is extended or adjusted under 35 U.S.C. 154(b) by 0 days.

(21) Appl. No.: 12/708,506

(22) Filed: Feb. 18, 2010

(65) Prior Publication Data

US 2010/0226901 A1     Sep. 9, 2010

Related U.S. Application Data

(60) Provisional application No. 61/207,900, filed on Feb. 18, 2009.

(51) Int. Cl.
*C07H 21/02* (2006.01)
*C07H 21/04* (2006.01)
*C12N 5/00* (2006.01)
*C12N 5/02* (2006.01)

(52) U.S. Cl. .............. 536/23.1; 536/24.1; 536/24.5; 435/375

(58) Field of Classification Search ............... 536/23.1, 536/24.1, 24.5; 435/375
See application file for complete search history.

(56) References Cited

U.S. PATENT DOCUMENTS

| | | | |
|---|---|---|---|
| 4,235,871 A | 11/1980 | Papahadjopoulos et al. |
| 4,426,330 A | 1/1984 | Sears |
| 4,501,728 A | 2/1985 | Geho et al. |
| 4,534,899 A | 8/1985 | Sears |
| 4,737,323 A | 4/1988 | Martin et al. |
| 4,837,028 A | 6/1989 | Allen |
| 4,897,355 A | 1/1990 | Eppstein et al. |
| 5,013,556 A | 5/1991 | Woodle |
| 5,013,830 A | 5/1991 | Ohtsuka et al. |
| 5,093,246 A | 3/1992 | Cech |
| 5,108,921 A | 4/1992 | Low |
| 5,176,996 A | 1/1993 | Hogan |
| 5,213,804 A | 5/1993 | Martin |
| 5,214,135 A | 5/1993 | Srivastava et al. |
| 5,227,170 A | 7/1993 | Sullivan |
| 5,256,775 A | 10/1993 | Froehler |
| 5,264,221 A | 11/1993 | Tagawa |
| 5,264,423 A | 11/1993 | Cohen et al. |
| 5,264,564 A | 11/1993 | Matteucci |
| 5,270,163 A | 12/1993 | Gold |
| 5,276,019 A | 1/1994 | Cohen et al. |
| 5,354,844 A | 10/1994 | Beug |
| 5,356,633 A | 10/1994 | Woodle |
| 5,395,619 A | 3/1995 | Zalipsky |
| 5,416,016 A | 5/1995 | Low |
| 5,417,978 A | 5/1995 | Tari |
| 5,459,127 A | 10/1995 | Felgner |
| 5,462,854 A | 10/1995 | Coassin |
| 5,469,854 A | 11/1995 | Unger |
| 5,512,295 A | 4/1996 | Kornberg |
| 5,521,291 A | 5/1996 | Curiel |
| 5,525,719 A | 6/1996 | Srivastava et al. |
| 5,527,528 A | 6/1996 | Allen |
| 5,534,259 A | 7/1996 | Zalipsky |
| 5,543,152 A | 8/1996 | Webb |
| 5,543,158 A | 8/1996 | Gref |
| 5,547,932 A | 8/1996 | Curiel |
| 5,556,948 A | 9/1996 | Tagawa |
| 5,580,575 A | 12/1996 | Unger |
| 5,582,981 A | 12/1996 | Toole |
| 5,583,020 A | 12/1996 | Sullivan |
| 5,591,721 A | 1/1997 | Agrawal |
| 5,595,756 A | 1/1997 | Bally |
| 5,736,392 A | 4/1998 | Hawley-Nelson et al. |
| 5,756,291 A | 5/1998 | Griffin |
| 5,767,099 A | 6/1998 | Harris et al. |
| 5,777,153 A | 7/1998 | Lin et al. |

(Continued)

FOREIGN PATENT DOCUMENTS

| | | |
|---|---|---|
| AU | 2004206255 B2 | 8/2008 |
| WO | WO 88/04300 | 6/1988 |
| WO | WO 88/09810 | 12/1988 |
| WO | WO 89/10134 | 11/1989 |
| WO | WO 90/11364 | 10/1990 |
| WO | WO 90/14074 A1 | 11/1990 |
| WO | WO 91/16024 A1 | 10/1991 |
| WO | WO 91/17424 A1 | 11/1991 |
| WO | WO 92/03568 A1 | 3/1992 |
| WO | WO 97/42317 | 11/1997 |

(Continued)

OTHER PUBLICATIONS

Win et al. RNA as a Versatile and Powerful Platform for Engineering Genetic Regulatory Tools, Biotechnology and Genetic Engineering Reviews 24: 311-346, 2007.*

(Continued)

*Primary Examiner* — Wu-Cheng Winston Shen
(74) *Attorney, Agent, or Firm* — McCarter & English, LLP; Elizabeth A. Hanley; Yu Lu

(57) ABSTRACT

The present application relates to nucleic acids that encode a RNA switch responsive to a ligand that can control the expression of a gene product that affects the cell fate determination of a mammalian cell are provided. In some embodiments, the system can be used to control the proliferation or activation of mammalian cells in response to a ligand that can be provided exogenously to the mammalian cell or can be produced by the mammalian cell. The system can be used to promote the growth or proliferation of human T cells in response to an exogenous ligand applied to the cells. In one embodiment, the system detects the ligand through a RNA aptamer that modulates expression of a gene product through activation or inactivation of a ribozyme that modulates expression of the gene product.

21 Claims, 20 Drawing Sheets

U.S. PATENT DOCUMENTS

| | | | |
|---|---|---|---|
| 5,780,053 | A | 7/1998 | Ashley et al. |
| 5,830,430 | A | 11/1998 | Unger et al. |
| 5,830,653 | A | 11/1998 | Froehler et al. |
| 5,851,548 | A | 12/1998 | Dattagupta et al. |
| 5,855,910 | A | 1/1999 | Ashley et al. |
| 6,458,559 | B1 | 10/2002 | Shi et al. |
| 2002/0106648 | A1 | 8/2002 | Lizardi et al. |
| 2002/0150996 | A1 | 10/2002 | Nilsen-Hamilton |
| 2002/0166132 | A1 | 11/2002 | Scherman et al. |
| 2003/0105051 | A1 | 6/2003 | McSwiggen |
| 2003/0124595 | A1 | 7/2003 | Lizardi |
| 2003/0157030 | A1 | 8/2003 | Davis et al. |
| 2004/0063654 | A1 | 4/2004 | Davis |
| 2004/0072785 | A1 | 4/2004 | Wolff et al. |
| 2004/0086884 | A1 | 5/2004 | Beach |
| 2004/0162235 | A1 | 8/2004 | Trubetskoy et al. |
| 2004/0204377 | A1 | 10/2004 | Rana et al. |
| 2005/0003362 | A1 | 1/2005 | Crylov et al. |
| 2005/0026286 | A1 | 2/2005 | Chi et al. |
| 2005/0037496 | A1 | 2/2005 | Rozema et al. |
| 2005/0042227 | A1 | 2/2005 | Zankel et al. |
| 2005/0048647 | A1 | 3/2005 | Taira et al. |
| 2005/0064595 | A1 | 3/2005 | MacLachlan et al. |
| 2005/0256071 | A1 | 11/2005 | Davis |
| 2005/0265957 | A1 | 12/2005 | Monahan et al. |
| 2006/0008910 | A1 | 1/2006 | MacLachlan et al. |
| 2006/0088864 | A1 | 4/2006 | Smolke et al. |
| 2006/0105975 | A1 | 5/2006 | Pendergrast et al. |
| 2006/0172925 | A1 | 8/2006 | Gorenstein et al. |
| 2006/0178327 | A1 | 8/2006 | Yeung et al. |
| 2006/0240093 | A1 | 10/2006 | MacLachlan et al. |
| 2007/0077571 | A1 | 4/2007 | Ellington |
| 2007/0083947 | A1 | 4/2007 | Huang et al. |
| 2007/0231392 | A1 | 10/2007 | Wagner et al. |
| 2008/0038296 | A1 | 2/2008 | Brahmbhatt et al. |
| 2008/0107694 | A1 | 5/2008 | Trogden et al. |
| 2008/0112916 | A1 | 5/2008 | Wagner et al. |
| 2008/0152661 | A1 | 6/2008 | Rozema et al. |
| 2009/0082217 | A1 | 3/2009 | Smolke et al. |
| 2009/0098561 | A1 | 4/2009 | Smolke et al. |
| 2009/0143327 | A1 | 6/2009 | Smolke et al. |
| 2009/0234109 | A1 | 9/2009 | Han et al. |
| 2010/0255545 | A1 | 10/2010 | Smolke et al. |
| 2011/0002892 | A1 | 1/2011 | Galloway et al. |

FOREIGN PATENT DOCUMENTS

| | | |
|---|---|---|
| WO | WO 98/13526 A1 | 4/1998 |
| WO | WO 9904800 | 2/1999 |
| WO | WO 99/27133 | 6/1999 |
| WO | WO 99/54506 | 10/1999 |
| WO | WO 00/20040 | 4/2000 |
| WO | WO 2004033653 A2 | 4/2004 |
| WO | WO 2004/048545 A2 | 6/2004 |
| WO | WO 2004/065601 A2 | 8/2004 |
| WO | WO 2005001039 A2 | 1/2005 |
| WO | WO 2005111238 A2 | 11/2005 |
| WO | WO 2006086669 | 8/2006 |
| WO | WO 2007/089607 A2 | 8/2007 |
| WO | WO 2008/036825 A2 | 3/2008 |

OTHER PUBLICATIONS

U.S. Appl. No. 12/218,628, filed Mar. 26, 2009, Christina D. Smolke.
Buskirk et al., "Engineering a Ligand-Dependent RNA Transcriptional Activator." 2004 Chemistry & Biology 11:1157-1163.
Buskirk et al., "In Vivo Evolution of an RNA-Based Transcriptional Activator." 2003 Chemistry & Biology 10:533-540.
Famulok, "Bringing Picomolar Protein Detection Into Proximity." 2002 Nature Biotechnology 20:448-449.
Fredriksson et al., "Protein Detection Using Proximity-Dependent DNA Litagation Assays." 2002 Nature Biotechnology 20:473-477.
Hesselberth et al., "Simultaneous Detection of Diverse Analytes with an Aptazyme Ligase Array." 2003 Analytical Biochemistry 312:106-112.
Luzi et al., "New Trends in Affinity Sensing: Aptamers for Ligand Binding." 2003 Trends in Analytical Chemistry 22:810-818.
Nutiu et al., "Structure-Switching Signaling Aptamers: Transducing Molecular Recognition Into Fluorescence Signaling." 2004 Chem. Eur. J. 10:1868-1876.
Nutiu et al., "Structure-Switching Signaling Aptamers." 2003 J. Am. Chem. Soc. 125:4771-4778.
Silverman, "Rube Goldberg Goes (RIBO)Nuclear? Molecular Switches and Sensors Made From RNA." 2003 RNA 9:377-383.
Winkler et al., "An mRNA Structure That Controls Gene Expression by Binding FMN." 2002 PNAS 99:15908-15913.
Winkler et al., "Genetic Control by Metabolite-Binding Riboswitches." 2003 ChemBioChem 4:1024-1032.
Al-Douahji et al., "The cyclin kinase inhibitor p21WAF1/C1P1 is required for glomerular hypertrophy in experimental diabetic nephropathy." 1999 Kidney Int 56:1691-1699.
Banerjee et al., "Control of developmental timing by small temporal RNAs: a paradigm for RNA-mediated reaulation of gene expression." 2002 Bioessays 24:119-129.
Barrick et al., "New RNA motifs suggest an expanded scope for riboswitches in bacterial genetic control." 2004 Proc Natl Acad Sci USA 101:6421-6426.
Bartel, "MicroRNAs: genomics, biogenesis, mechanism, and function." 2004 Cell 116:281-297.
Batzer et al., "Enhanced evolutionary PCR using oligonucleotides with inosine at the 3'-terminus." 1991 Nucleic Acids Res 19:5081.
Bayer et al., "Programmable ligand-controlled riboregulators of eukaryotic gene expression." 2005 Nat Biotechnol 23:337-343.
Been and Cech, "One binding site determines sequence specificity of Tetrahymena pre-rRNA self-splicing, trans-splicing, and RNA enzyme activity." 1986 Cell 47:207-216.
Benoist et al., "In vivo sequence requirements of the SV40 early promotor region." 1981 Nature 290:304-310.
Berens et al., "A tetracycline-binding RNA aptamer." 2001 Bioorg Med Chem 9:2549-2556.
Blind et al., "Cytoplasmic RNA modulators of an inside-out signal-transduction cascade." 1999 Proc Natl Acad Sci USA 96:3606-3610.
Brennecke et al., "Towards a complete description of the microRNA complement of animal genomes." 2003 Genome Biol 4:228.1-228.3.
Brinster et al., "Regulation of metallothionein-thymidine kinase fusion plasmids injected into mouse eggs." 1982 Nature 296:39-42.
Brummelkamp et al., "A system for stable expression of short interfering RNAs in mammalian cells." 2002 Science 296:550-553.
Buskirk et al., "Engineering a ligand-dependent RNA transcriptional activator." 2004 Chem Biol 11:1157-1163.
Caplen et al., "Specific inhibition of gene expression by small double-stranded RNAs in invertebrate and vertebrate systems." 2001 Proc Natl Acad Sci USA 98:9742-9747.
Caponigro et al., "A small segment of the MATa1 transcript promotes mRNA decay in *Saccharomyces cerevisiae*: a stimulatory role for rare codons." 1993 Mol Cell Biol 13:5141-5148.
Chen et al., "Synthesis of oligodeoxyribonucleotide N3' ->P5' phosphoramidates". 1995 Nucleic Acids Res 23:2661-2668.
Cox et al., "Automated selection of aptamers against protein targets translated in vitro: from gene to aptamer." 2002 Nucleic Acids Res 30:e108.
Dragun et al., "Inhibition of intercellular adhesion molecule-1 with antisense deoxynucleotides prolonos renal isograft survival in the rat." 1998 Kidney Int 54:2113-2122.
Dragun et al., "ICAM-1 antisense oligodesoxynucleotides prevent reperfusion injury and enhance immediate graft function in renal transplantation." 1998 Kidney Int 54:590-602.
Egholm et al., "PNA hybridizes to complementary oligonucleotides obeying the Watson-Crick hydrogen-bonding rules." 1993 Nature 365:566-568.
Elbashir et al., "Duplexes of 21-nucleotide RNAs mediate RNA interference in cultured mammalian cells." 2001 Nature 411:494-498.
Ellington et al., "In vitro selection of RNA molecules that bind specific ligands." 1990 Nature 346:818-822.
Famulok, "Oligonucleotide aptamers that recognize small molecules." 1999 Curr Opin Struct Biol 9:324-329.
Gardner et al., "Inferring genetic networks and identifying compound mode of action via expression profiling." 2003 Science 301:102-105.

Gautier et al., "α-DNA. IV: α-anomeric and β-anomeric tetrathymidylates covalently linked to intercalating oxazolopyridocarbazole. Synthesis, physicochemical properties and poly (rA) Binding." 1987 Nucleic Acids Res 15:6625-6641.

Gil et al., "Induction of apoptosis by the dsRNA-dependent protein kinase (PKR): mechanism of action." 2000 Apoptosis 5:107-114.

Good, "Diverse antisense mechanisms and applications." 2003 Cell Mol Life Sci 60:823-824.

Good, "Translation repression by antisense sequences." 2003 Cell Mol Life Sci 60:854-861.

Gouda et al., "Free energy calculations for theophylline binding to an RNA aptamer: Comparison of MM-PBSA and thermodynamic integration methods." 2003 Biopolymers 68:16-34.

Haller et al., "Antisense oligonucleotides for ICAM-1 attenuate reperfusion injury and renal failure in the rat." 1996 Kidney Int 50:473-480.

Hamm et al., "Anti-idiotype RNA selected with an anti-nuclear export signal antibody is actively transported in oocytes and inhibits Rev- and cap-dependent RNA export." 1997 Proc Natl Acad Sci USA 94:12839-12844.

Haseloff et al., "Simple RNA enzymes with new and highly specific endoribonuclease activities." 1988 Nature 334:585-591.

Heidenreich et al., "RNase H-independent antisense activity of oligonucleotide N3' -> P5 ' phosphoramidates." 1997 Nucleic Acids Res 25:776-780.

Hermann et al., "Adaptive recognition by nucleic acid aptamers." 2000 Science 287:820-825.

Hesselberth et al., "Simultaneous detection of diverse analytes with an aptazyme ligase array." 2003 Anal Biochem 312:106-112.

Hirschbein et al., "31P NMR spectroscopy in oligonucleotide research and development." 1997 Antisense Nucleic Acid Drug Dev 7:55-61.

Huizenga et al., "A DNA aptamer that binds adenosine and ATP." 1995 Biochemistry 34:656-665.

Inoue et al., "Sequence-dependent hydrolysis of RNA using modified oligonucleotide splints and RNase H." 1987 FEBS Lett 215:327-330.

Inoue et al., "Synthesis and hybridization studies on two complementary nona(2'-O-methyl) ribonucleotides." 1987 Nucleic Acids Res 15:6131-6148.

Isaacs et al., "Engineered riboregulators enable post-transcriptional control of gene expression." 2004 Nat Biotechnol 22:841-847.

Jhaveri et al., "In vitro selection of signaling aptamers." 2000 Nat Biotechnol 18:1293-1297.

Jose et al., "Cooperative binding of effectors by an allosteric ribozyme." 2001 Nucleic Acids Res 29:1631-1637.

Kertsburg et al., "A versatile communication module for controlling RNA folding and catalysis." 2002 Nucleic Acids Res 30:4599-4606.

Khosla et al., "Metabolic engineering for drug discovery and development." 2003 Nat Rev Drug Discov 2:1019-1025.

Kim, "Small RNAs: classification, biogenesis, and function." 2005 Mol Cells 19:1-15.

Kipshidze et al., "local delivery of c-myc neutrally charged antisense oligonucleotides with transport catheter inhibits myointimal hyperplasia and positively affects vascular remodeling in the rabbit balloon injury model." 2001 Catheter Cardiovasc Intery 54:247-256.

Kipshidze et al., "Intramural coronary delivery of advanced antisense oligonucleotides reduces neointimal formation in the porcine stent restenosis model." 2002 JAm Coli Cardiol 39:1686-1691.

Kobayashi et al., "Programmable cells: interfacing natural and engineered gene networks." 2004 Proc Natl Acad Sci USA 101 :8414-8419.

Koch, "The metabolism of methylpurines by *Escherichia coli*. I. Tracer studies." 1956 J Bioi Chem 219:181-188.

Koizumi et al., "Allosteric selection of ribozymes that respond to the second messengers cGMP and cAMP." 1999 Nat Struct Biol 6:1062-1071.

Kramer et al., "Role for antisense RNA in regulating circadian clock function in Neurospora crassa." 2003 Nature 421:948-952.

Kutryk et al., "local intracoronary administration of antisense oligonucleotide against c-myc for the prevention of in-stent restenosis: results of the randomized investigation by the Thoraxcenter of antisense DNA using local delivery and IVUS after coronary stenting (ITALICS) trial." 2002 J Am Coll Cardiol 39:281-287.

Kuwabara et al., "Allosterically controllable ribozymes with biosensor functions." 2000 Curr Opin Chem Biol 4:669-677.

Kuwabara et al., "Allosterically controllable maxizyme-mediated suppression of progression of leukemia in mice." 2001 Biomacromolecules 2:1220-1228.

Kuwabara et al., "Allosterically controlled single-chained maxizymes with extremely high and specific activity." 2001 Biomacromolecules 2:788-799.

Lavorana et al., "In search of antisense." 2004 Trends Biochem Sci 29:88-94.

Lemaitre et al., "Specific antiviral activity of a pOly(L-lysine)-conjugated oligodeoxyribonucleotide sequence complementary to vesicular stomatitis virus N protein mRNA initiation site." 1987 Proc Natl Acad Sci USA 84:648-652.

Letsinger et al., "Cholesteryl-conjugated oligonucleotides: synthesis, properties, and activity as inhibitors of replication of human immunodeficiency virus in cell culture." 1989 Proc Natl Acad Sci USA 86:6553-6556.

Lilley, "The origins of RNA catalysis in ribozymes." 2003 Trends Biochem Sci 28:495-501.

Lorsch et al., "In vitro selection of RNA aptamers specific for cyanocobalamin." 1994 Biochemistry 33:973-982.

Mandal et al., "Adenine riboswitches and gene activation by disruption of a transcription terminator." 2004 Nat Struct Mol Biol 11:29-35.

Mannironi et al., "In vitro selection of dopamine RNA ligands." 1997 Biochemistry 36:9726-9734.

Mateus et al., "Destabilized green fluorescent protein for monitoring dynamic changes in yeast gene expression with flow cytometry." 2000 Yeast 16:1313-1323.

Mathews et al., "Incorporating chemical modification constraints into a dynamic programming algorithm for prediction of RNA secondary structure." 2004 Proc Natl Acad Sci USA 101:7287-7292.

McCaffrey et al., "RNA interference in adult mice." 2002 Nature 418:38-39.

McManus et al., "Gene silencing using micro-RNA desianed hairpins." 2002 RNA 8:842-850.

Nagai et al., "A variant of yellow fluorescent protein with fast and efficient maturation for cellbiological applications." 2002 Nat Biotechnol 20:87-90.

Nutiu et al., "Structure-switching signaling aptamers." 2003 J Am Chem Soc 125:4771-4778.

Ohtsuka et al., "An alternative approach to deoxyoligonucleotides as hybridization probes by insertion of deoxyinosine at ambiauous codon positions." 1985 J Biol Chem 260:2605-2608.

Paddison et al., "Stable suppression of gene expression by RNAi in mammalian cells." 2002 Proc Natl Acad Sci USA 99:1443-1448.

Paddison et al., "Short hairpin RNAs (shRNAs) induce sequence-specific silencing in mammalian cells." 2002 Genes Dev 16:948-958.

Perry-O'Keefe et al., "Peptide nucleic acid pre-gel hybridization: an alternative to Southern hybridization." 1996 Proc Natl Acad Sci USA 93:14670-14675.

Piganeau et al., "In vitro selection of allosteric ribozymes: theory and experimental validation." 2001 J Mol Biol 312:1177-1190.

Robertson et al., "Design and optimization of effector-activated ribozyme ligases." 2000 Nucleic Acids Res 28:1751-1759.

Rossolini et al., "Use of deoxyinosine-containing primers vs degenerate primers for polymerase chain reaction based on ambiguous sequence information." 1994 Moll Cell Probes 8:91-98.

Roth et al., "Selection in vitro of allosteric ribozymes." 2004 Methods Mol Biol 252:145-164.

Samarsky et al., "A small nucleolar RNA:ribozyme hybrid cleaves a nucleolar RNA target in vivo with near-perfect efficiency." 1999 Proc Natl Acad Sci USA 96:6609-6614.

Sarver et al., "Ribozymes as potential anti-HIV-1 therapeutic agents." 1990 Science 247:1222-1225.

Scherer et al., "Recent applications of RNAi in mammalian systems." 2004 Curr Pharm Biotechnol 5:355-360.

Scherer et al., "Approaches for the sequence-specific knockdown of mRNA." 2003 Nat Biotechnol 21:1457-1465.

Smolke et al., "Coordinated, differential expression of two genes through directed mRNA cleavage and stabilization by secondary structures." 2000 Appl Environ Microbiol 66:5399-5405.

Soukup et al., "Altering molecular recognition of RNA aptamers by allosteric selection." 2000 J Mol Biol 298:623-632.

Soukup et al., "Generating new ligand-binding RNAs by affinity maturation and disintegration of allosteric ribozymes." 2001 RNA 7:524-536.

Soukup et al., "Design of allosteric hammerhead ribozymes activated by ligand-induced structure stabilization." 1999 Structure 7:783-791.

Stein et al., "Oligodeoxynucleotides as inhibitors of gene expression: a review." 1988 Cancer Res 48:2659-2668.

Stojanovic et al., "Modular aptameric sensors." 2004 J Am Chem Soc 126:9266-9270.

Sui et al., "A DNA vector-based RNAi technology to suppress gene expression in mammalian cells." 2002 Proc Natl Acad Sci USA 99:5515-5520.

Taira et al., "Construction of a novel RNA-transcript-trimming plasmid which can be used both in vitro in place of run-off and (G)-free transcriptions and in vivo as multi-sequences transcription vectors." 1991 Nucleic Acids Res 19:5125-5130.

Tang et al., "Rational design of allosteric ribozymes." 1997 Chem Biol 4:453-459.

Tuerk et al., "Systematic evolution of ligands by exponential enrichment: RNA ligands to bacteriophage T4 DNA polymerase." 1990 Science 249:505-510.

Vacek et al., "Antisense-mediated redirection of mRNA splicing." 2003 Cell Mol Life Sci 60:825-833.

van der Krol et al., "Modulation of eukaryotic gene expression by complementary RNA or DNA sequences." 1988 Biotechniques 6:958-976.

Wagner et al., "Nucleotide sequence of the thymidine kinase gene of herpes simplex virus type 1." 1981 Proc Natl Acad Sci USA 78:1441-1445.

Wagner, "Gene inhibition using antisense oligodeoxynucleotides." 1994 Nature 372:333-335.

Wang et al., "A general approach for the use of oligonucleotide effectors to regulate the catalysis of RNA-cleaving ribozymes and DNAzymes." 2002 Nucleic Acids Res 30:1735-1742.

Wang et al., "A general strategy for effector-mediated control of RNA-cleaving ribozymes and Dna enzymes." 2002 J Mol Biol 318:33-43.

Watkins et al., "Metabolomics and biochemical profiling in drug discovery and development." 2002 Curr Opin Mol Ther 4:224-228.

Weiss et al., "Antisense RNA gene therapy for studying and modulating biological processes." 1999 Cell Mol Life Sci 55:334-358.

Werstuck et al., "Controlling gene expression in living cells through small molecule-RNA interactions." 1998 Science 282:296-298.

Wilda et al., "Killing of leukemic cells with a BCRIABL fusion gene by RNA interference I (RNAi)." 2002 Oncogene 21:5716-5724.

Wilson et al., "The interaction of intercalators and groove-binding agents with DNA triplehelical structures: the influence of ligand structure, DNA backbone modifications and sequence." 1994 J Mol Recognit 7:89-98.

Winkler et al., "Control of gene expression by a natural metabolite-responsive ribozyme." 2004 Nature 428:281-286.

Winkler et al., "Thiamine derivatives bind messenger RNAs directly to regulate bacterial gene expression." 2002 Nature 419:952-956.

Yamamoto et al., "Identification of a functional promoter in the long terminal repeat of Rous sarcoma virus." 1980 Cell 22:787-797.

Yelin et al., "Widespread occurrence of antisense transcription in the human genome." 2003 Nat Biotechnol 21:379-386.

Yen et al., "Exogenous control of mammalian gene expression through modulation of RNA self-cleavage." 2004 Nature 431:471-476.

Yu et al., "RNA interference by expression of short-interfering RNAs and hairpin RNAs in mammalian cells." 2002 Proc Natl Acad Sci USA 99:6047-6052.

Zaug et al., "A labile phosphodiester bond at the ligation junction in a circular intervening sequence RNA." 1984 Science 224:574-578.

Zaug et al., "The intervening sequence RNA of Tetrahymena is an enzyme." 1986 Science 231:470-475.

Zaug et al., "The Tetrahymena ribozyme acts like an RNA restriction endonuclease." 1986 Nature 324:429-433.

Zimmermann et al., "Interlocking structural motifs mediate molecular discrimination by a theophylline-binding RNA." 1997 Nat Struct Biol 4:644-649.

Zimmermann et al., "Molecular interactions and metal binding in the theophylline-binding core of an RNA aptamer." 2000 RNA 6:659-667.

Zon, "Oligonucleotide analogues as potential chemotherapeutic agents." 1988 Pharm Res 5:539-549.

Vuyisich et al., "Controlling protein activity with ligand-regulated RNA aptamers." 2002 Chemistry & Biology, 9:907-913.

Agrawal et al., "RNA interference: biology, mechanism, and applications." 2003 Microbiology and Molecular Biology Reviews, 67:657-685.

Soukup et al., "Nucleic acid molecular switches." 1999 Trends in Biotechnology 17:469-476.

Carmell et al., "RNase III enzymes and the initiation of gene silencing." 2004 Nature Structural & Molecular Biology, 11:214-218.

An et al., "Artificial control of gene expression in mammalian cells by modulating RNA interference through aptamer-small molecule interaction." 2006, RNA 12(5):710-716.

Bauer G. et al., "Engineered riboswitches as novel tools in molecular biology." 2006, Journal of Biotechnology 124(1):4-11.

Berezovski et al., "Nonequilibrium Capillary Electrophoresis of Equilibrium Mixtures: A Universal Tool for Development of Aptamers." 2005, J. Am. Chem. Soc. 127:3165-3171.

Davidson et al., "Synthetic RNA circuits." 2007, Nature Chemical Biology 3(1):23-28.

Desai et al., "Genetic screens and selections for small molecules based on a synthetic riboswitch that activates protein translation." 2004, Journal of the American Chemical Society 126:13247-13254.

Drabovich et al., "Selection of Smart Aptamers by Equilibrium Capillary Electrophoresis of Eauilibrium Mixtures (ECEEM)." 2005 J. Am. Chem. Soc. 127:11224-11225.

Isaacs et al., "RNA synthetic biology." 2006 Nature Biotechnology 24(5):545-554.

John J. Rossi, "Targeted cleavage: Tuneable cis-cleaving ribozymes." 2007 PNAS 104(38):14881-14882.

Mendonsa et al., "In Vitro Evolution of Functional DNA Using Capillary Electrophoresis." 2004 J. Am. Chem. Soc. 126:20-21.

Mendonsa et al., "In Vitro Selection of Aptamers with Affinity for Neuropeptide Y Using D Capillary Electrophoresis." 2005 J. Am. Chem. Soc. 127:9382-9383.

Mendonsa et al., "In Vitro Selection of High-Affinity DNA Ligands for Human IgE Using Capillary Electrophoresis." 2004 Anal. Chern. 76:5387-5392.

Smolke et al., "Molecular Switches for Cellular Sensors." 2005 Engineering & Science 67(4):28-37.

Sudarsan et al., "Tandem riboswitch architectures exhibit complex gene control functions." 2006 Science 314(5797):300-304.

Suess et al., "A theophylline responsive riboswitch based on helix slipping controls gene expression in vivo." 2004 Nucleic Acids Research. 32(4):1610-1614.

Yokobayashi et al., "Directed evolution of a genetic circuit." 2002 Proc Natl Acad Sci USA 99:16587-16591.

Basu et al., "Spatiotemporal control of gene expression with pulse-generatinq networks." 2004 Proc Natl Acad Sci USA 101:6355-6360.

Levine et al., "Quantitative Characteristics of Gene Regulation by Small RNA." 2007 PLoS Biol 5(e229):1998-2010.

Hebert et al., "Loss of microRNA cluster miR-29a/b-1 in sporadic Alzheimer's disease correlates with increased BACE1-β-secretase expression." 2008 Proc Natl Acad Sci USA 105:6415-6420.

Calin et al., "MiR-15a and miR-16-1 cluster functions in human leukemia." 2008 Proc Natl Acad Sci USA 105:5166-5171.

Ventura et al., "Targeted Deletion Reveals Essential and Overlapping Functions of the miR-17~92 Family of miRNA Clusters." 2008 Cell 132:875-886.

Welz et al., "Ligand binding and gene control characteristics of tandem riboswitches in *Bacillus anthracis*." 2007 RNA 13:573.

Rodionov et al., "Reconstruction of regulatory and metabolic pathways in metal-reducing δ-proteobacteria." 2004 Genome Biol 5

Rinaudo et al., "A universal RNAi-based logic evaluator that operates in mammalian cells." 2007 Nat Biotechnol 25:795-801.
Deans et al., "A Tunable Genetic Switch Based on RNAi and Repressor Proteins for Regulating Gene Expression in Mammalian Cells." 2007 Cell 130:363-372.
Berge et al., "Pharmaceutical Salts." 1977 J. of Pharm Sci. 66:1-19.
Guet et al., "Combinatorial synthesis of genetic networks." 2002 Science 296:1466-1470.
Kramer et al.," BioLogic gates enable logical transcription control in mammalian cells." 2004 Biotechnol Bioeng 87:478-484.
Cox et al., "Programming gene expression with combinatorial promoters." 2007 Mol Syst Biol 3:145.
Anderson et al., "Environmental signal integration by a modular AND gate." 2007 Mol Syst Biol 3:133.
Seelig et al.,"Enzyme-Free Nucleic Acid Logic Circuits." 2006 Science 314:1585-1588.
Benenson et al., "An autonomous molecular computer for logical control of gene expression." 2004 Nature 429:423-429.
Dirks et al., "Triggered amplification by hybridization chain reaction." 2004 Proc Natl Acad Sci USA 101:15275-15278.
Stojanovic et al., "A deoxyribozyme-based molecular automaton." 2003 Nat Biotechnol 21:1069-1074.
Penchovsky et al., "Computational design and experimental validation of oligonucleotide-sensing allosteric ribozymes." 2005 Nat Biotechnol 23:1424-1433.
Breaker, "Engineered allosteric ribozymes as biosensor components." 2002 Curr Opin Biotechnol 13:31-39.
Robertson et al., "In vitro selection of an allosteric ribozyme that transduces analytes to amplicons." 1999 Nat Biotechnol 17:62-66.
Suess et al., "Engineered riboswitches: overview, problems and trends." 2008 RNA Biol 5(1):1-6.
Brown et al., "Endogenous microRNA can be broadly exploited to regulate transgene expression according to tissue, lineage and differentiation state." 2007 Nat Biotechnol 25:1457-1467.
Parisien et al., "The MC-Fold and MC-Sym pipeline infers RNA structure from sequence data." 2008 Nature 452:51-55
Mathews et al., "Prediction of RNA secondary structure by free energy minimization." 2006 Curr Opin Struct Biol 16:270-278.
Khvorova et al., "Sequence elements outside the hammerhead ribozyme catalytic core enable intracellular activity." 2003 Nat Struct Bioi 10:708-872.
Mandal et al., "A glycine-dependent riboswitch that uses cooperative binding to control gene expression." 2004 Science 306:275-279.
Woodside et al., "Nanomechanical measurements of the sequence-dependent folding landscapes of single nucleic acid hairpins." 2006 Proc Natl Acad Sci USA 103:6190-6195.
Stein et al., "Physicochemical properties of phosphorothioate oligodeoxynucleotides." 1988 Nucl. Acids Res. 16:3209-3221.
Sarin et al., "Inhibition of acquired immunodeficiency syndrome virus by oligodeoxynucleoside methylphosphonates." 1988 Proc. Natl. Acad. Sci. USA 85:7448-7451.
MacRae et al., "Structural Basis for Double-Stranded RNA Processing by Dicer." 2006 Science 311( 5758):195-198.
Zeng and Cullen, "Structural requirements for pre-microRNA binding and nuclear export by Exportin 5." 2004 Nucleic Acids Res. 32(16):4776-85.
Griffiths-Jones, "The microRNA Registry." 2004 Nucleic Acids Res. 32:D109-111.
Griffiths-Jones et al., "miRBase: microRNA sequences, targets and gene nomenclature." 2006 Nucleic Acids Res. 34:D140-144.
Soukup and Breaker, "Relationship between internucleotide linkage geometry and the stability of RNA." 1999 RNA 5:1308-1325.
Abbas-Terki et al., "Lentiviral-mediated RNA interference." 2002 Hum Gene Ther 13: 2197-2201.
Hutvagner et al., "Sequence-specific inhibition of small RNA function." 2004 PLoS Biol 2: E98.
Meister, "Sequence-specific inhibition of microRNA- and siRNA-induced RNA silencing." 2004 RNA 10:544-550.
Bartlett and Davis, "Insights into the kinetics of siRNA-mediated gene silencing from live-cell and live-animal bioluminescent imaging." 2006 Nucleic Acids Res 34:322-333.
Malphettes and Fussenegger, "Impact of RNA interference on gene networks." 2006 Metab Eng 8:672-683.
Raab and Stephanopoulos, "Dynamics of gene silencing by RNA interference." 2004 Biotechnol Bioeng 88:121-132.
Kiga et al., "An RNA aptamer to the xanthine-guanine base with a distinctive mode of purine recognition." 1998 Nucleic Acids Res 26:1755-1760.
Thompson et al., "Group I aptazymes as genetic regulatory switches." 2002 BMC Biotechnol 2:21.
Suel et al., "Tunability and noise dependence in differentiation dynamics." 2007 Science 315:1716-1719.
Gardner et al., "Construction of a genetic toggle switch in *Escherichia coli*." 2000 Nature 403:339-342.
Yi et al., "Exportin-5 mediates the nuclear export of premicroRNAs and short hairpin RNAs." 2003 Genes Dev 17:3011-3016.
Ketting et al., "Dicer functions in RNA interference and in synthesis of small RNA involved in developmental timing in *C. elegans*." 2001 Genes Dev 15:2654-2659.
Gregory et al., "Human RISC couples microRNA biogenesis and posttranscriptional gene silencing." 2005 Cell 123:631-640.
Kok et al., "Human TRBP and PACT directly interact with each other and associate with dicer to facilitate the production of small interfering RNA." 2007 J Biol Chem 282:17649-17657.
Lee et al., "The role of PACT in the RNA silencing pathway." 2006 EMBO J 25:522-532.
Matranga et al., "Passenger-strand cleavage facilitates assembly of siRNA into Ag02-containing RNAi enzyme complexes." 2005 Cell 123:607-620.
Rand et al., "Argonaute2 cleaves the anti-guide strand of siRNA during RISC activation." 2005 Cell 123:621-629.
Westerhout and Berkhout, "A systematic analysis of the effect of target RNA structure on RNA interference." 2007 Nucleic Acids Res. 35(13):4322-4330.
Grimm et al., "Fatality in mice due to oversaturation of cellular microRNNshort hairpin RNA pathways." 2006 Nature 441:537-541.
Yi et al., "Overexpression of exportin 5 enhances RNA interference mediated by short hairpin RNAs and microRNAs." 2005 RNA 11:220-226.
Danilova et al., "RNAKinetics: a web server that models secondary structure kinetics of an elongating RNA." 2006 J Bioinform Comput Biol 4:589-596.
Croft et al., "Is prokaryotic complexity limited by accelerated growth in regulatory overhead?" 2003 Genome Biology 5:P2.
Dueber et al., "Engineering synthetic signaling proteins with ultrasensitive input-output control." 2007 Nat Biotechnol 25:660-662.
Elowitz and Leibler, "A synthetic oscillatory network of transcriptional regulators." 2000 Nature 403:335-338.
Flotte, "Size does matter: overcoming the adeno-associated virus packaging limit." 2000 Respir Res 1:16-18.
Grate and Wilson, "Inducible regulation of the *S. cerevisiae* cell cycle mediated by an RNA aptamer-ligand complex." 2001 Bioorg Med Chem 9:2565-2570.
Grieger and Samulski, "Packaging capacity of adeno-associated virus serotypes: impact of larger genomes on infectivity and postentry steps." 2005 J Virol 79:9933-9944.
Grundy and Henkin, "From ribosome to riboswitch: control of gene expression in bacteria by RNA structural rearrangements." 2006 Crit Rev Biochem Mol Biol 41:329-338.
Hall et al., "Computational selection of nucleic acid biosensors via a slip structure model." 2007 Biosens Bioelectron 22:1939-1947.
Hooshangi et al., "Ultrasensitivity and noise propagation in a synthetic transcriptional cascade." 2005 Proc Natl Acad Sci USA 102: 3581-3586.
Huang and Ferrell, "Ultrasensitivity in the mitogen-activated protein kinase cascade." 1996 Proc Natl Acad Sci USA 93: 10078-10083.
Jenison et al., "High-resolution molecular discrimination by RNA" 1994 Science 263:1425-1429.
Lee et al., "Aptamer database." 2004 ucleic Acids Res 32:D95-100.
Lynch et al., "A high-throughput screen for synthetic riboswitches reveals mechanistic insights into their function." 2007 Chem Biol 14:173-184.
Ogawa and Maeda, "An artificial aptazyme-based riboswitch and its cascading system in *E. coli*." 2008 Chembiochem 9:206-209.

Shalgi et al., "Global and Local Architecture of the Mammalian microRNA-Transcription Factor Regulatory Network." 2007 PLoS Comput Biol 3:e131.

Sudarsan et al., "Metabolite-binding RNA domains are present in the genes of eukaryotes." 2003 RNA 9:644-647.

Suess et al., "Conditional gene expression by controlling translation with tetracycline-binding aptamers." 2003 Nucleic Acids Res 31:1853-1858.

Weigand and Suess, "Tetracycline aptamer-controlled regulation of pre-mRNA splicing in yeast." 2007 Nucleic Acids Res 35:4179-4185.

Wieland and Hartig, "Improved aptazyme design and in vivo screening enable riboswitching in bacteria." 2008 Angew Chern Int Ed Eng147:2604-2607.

Javaherian et al., "Selection of aptamers for a protein target in cell lysate and their application to protein purification." 2009 Nucleic Acids Res. 37(8):e62.

Yunusov et al., "Kinetic capillary electrophoresis-based affinity screening of aptamer clones." 2009 Anal Chim Acta. 631(1):102-7.

Amarzguioui et. al., "Tolerance for mutations and chemical modifications in a siRNA." Nucleic Acid Research 31: 589-595, 2003.

Chiu & Rana, "RNAi in Human Cells: Basic Structural and Functional Features of Small Interfering RNA." Mol. Cell 10: 549-561,2002.

Chiu & Rana, "siRNA function in RNAi: A chemical modification analysis." RNA 9: 1034-1048,2003.

Geiger, Burgstaller et al., "RNA aptamers that bind L-arginine with sub-micromolar dissociation constants and high enantioselectivity." Nucleic Acids Research vol. 24, Issue 6, 1029-1036, 1996.

Hamada et al., "Effects on RNA Interference in Gene Expression (RNAi) in Cultured Mammalian Cells of Mismatches and the Introduction of Chemical Modifications at the 3'-Ends of siRNAs." *Antisense Nucleic Acid Drug Dev*. 12(5): 301-309,2002.

Harborth et aL, "Sequence, Chemical, and Structural Variation of Small Interfering RNAs and Short Hairpin RNAs and the Effect on Mammalian Gene Silencing." *Antisense Nucleic Acid Drug Dev*. 13(2): 83-105,2003.

Hwang et aL, "A Hexanucleotide Element Directs MicroRNA Nuclear Import." *Science* 315: 97-100, 2007.

Kim et al, "Synthetic dsRNA Dicer substrates enhance RNAi potency and efficacy." *Nature Biotech*. 23: 222-226, 2008.

Lescoute and Westhof, "Topology of three-way junctions in folded RNAs." *RNA* 12: 83-93, 2006.

Li and Breaker, "Kinetics of RNA Degradation by Specific Base Catalysis of Transesterification Involving the 2'-Hydroxyl Group." *J Am. Chem. Soc*. 121: 5364-5372, 1999.

McBride et al., "Artificial miRNAs mitigate shRNA-mediated toxicity in the brain: Implications for the therapeutic development of RNAi."*PNAS* 105: 5868, 2008.

Nickols et al., "Suppression of androgen receptor-mediated gene expression by a sequence-specific DNA-binding polyamide." *Proc. Natl. Acad. Sci. USA* 104: 10418-10423,2007.

Ohrt et al., "Fluorescence correlation spectroscopy and fluorescence cross-correlation spectroscopy reveal the cytoplasmic origination of loaded nuclear RISC in vivo in human cells." *Nucleic Acids Res*. 36(20): 6439-6449, 2008.

Schwarz et. al., "Evidence that siRNAs Function as Guides, Not Primers, in the *Drosophila* and Human RNAi Pathways." Mol. Cell 10: 537-548, 2002.

Soukup and Soukup, "Riboswitches exert genetic control through metabolite-induced conformational change." Current Opinions in Structural Biology 14: 344, 2004.

Zhou et al., "Novel Dual Inhibitory Function Aptamer-siRNA Delivery System for HIV-1 Therapy." *Molecular Therapy* 16: 1481-1489,2008.

Beisel et al., "Model-guided design of ligand-regulated RNAi for programmable control of gene expression." 2008, Molecular Systems Biology 4:224.

Win et al., "A modular and extensible RNA-based gene-regulartory platform for engineering cellular function." 2007 PNAS 104(36):14283-14288.

Win et al., "RNA as a Versatile and Powerful Platform for Engineering Genetic Regulartory Tools." 2007 Biotechnoloay and Genetic Engineering Reviews 24:311-346.

Berens et a., "Synthetic riboregulators—an alternative means to control gene expression" 2005 Gene Therapy and Molecular Biology 9:417-422.

Chen et al., "Genetic control of mammalian T-cell proliferation with synthetic RNA regulatory systems." 2010 Proc. Natl. Acad. Sci. USA. 107: 8531-6.

Culler et al., "Functional selection and systematic analysis of intronic splicing elements identifies active sequence motifs and associated splicing factors." 2010 Nuc. Acids Res. 38: 5152-65.

Hoff et al., "In vivo fluorescent detection of Fe-S clusters coordinated by human GRX2." 2009 Chem. Biol. 16: 1299-308.

Smolke, "Building outside of the box: iGEM and the BioBricks Foundation." 2009 Nat. Biotech. 27:1099-102.

Smolke, "It's the DNA that counts." 2009 Science. 324: 1156-7.

Beisel et al., "Design principles for riboswitch function." 2009 PLoS Comp. Biol. 5: e1000363.

Win et al., "Frameworks for programming biological function through RNA parts and devices." 2009 Chem. Biol. 16: 298-310.

Bayer et al., "Synthetic control of a fitness tradeoff in yeast nitrogen metabolism." 2009 J. Biol. Eng. 3: 1.

Hoff et al., "Fluorescence detection of a protein-bound 2Fe2S cluster." 2009 Chembiochem. 10: 667-70.

Hawkins et al., "Production of benzylisoquinoline alkaloids in *Saccharomyces cerevisiae*." 2008 Nat. Chem. Biol. 4: 564-73.

Benenson, "Small hairpin RNA as a small molecule sensor." 2008 Mol. Sys. Biol. 4: 227.

Keasling, "From yeast to alkaloids." 2008 Nat. Chem. Biol. 4: 524-5.

Win et al., "Higher-order cellular information processing with synthetic RNA devices." 2008 Science. 322: 456-60.

Shapiro et al., "RNA computing in a living cell." 2008 Science. 322: 387-8.

Baker et al., "Engineering life: building a Fab for biology." 2006 Scientific American. 294: 44-51.

Win et al., "Codeine-binding RNA aptamers and rapid determination of their binding constants using a direct coupling surface plasmon resonance assay." 2006 Nuc. Acids Res. 34: 5670-82.

Pfleger et al., "Combinatorial engineering of intergenic regions in operons tunes expression of multiple genes." 2006 Nat. Biotech. 24: 1027-32.

Hawkins et al., "The regulatory roles of the galactose permease and kinase in the induction response of the GAL network in *Saccharomyces cerevisiae*." 2006 J. Biol. Chem. 281: 13485-92.

Isaacs et al., "Plug and play with RNA." 2005 Nat. Biotech. 23: 306-7.

Martin et al., "Redesigning cells for the production of complex organic molecules." 2002 ASM News 68: 336-43.

Smolke et al., "Effect of gene location, mRNA secondary structures, and RNase sites on expression of two genes in an engineered operon." 2002 Biotech. Bioeng. 80: 762-76.

Smolke et al., "Effect of copy number and mRNA processing and stabilization on transcript and protein levels from an engineered dual-gene operon." 2002 Biotech. Bioeng. 78: 412-24.

Smolke et al., "Effects of transcription induction homogeneity and transcript stability on expression of two genes in a constructed operon." 2001 Appl. Micro. Biotech. 57: 689-96.

Smolke et al., "Controlling the metabolic flux through the carotenoid pathway using directed mRNA processing and stabilization." 2001 Met. Eng. 3: 313-21.

Duconge and Toulme, "In vitro selection identifies key determinants for loop-loop interactions: RNA aptamers selective for the TAR RNA element of HIV-1." 1999 RNA 5: 1605-1614.

Aagaard et al., "Engineering and optimization of the miR-1 06b cluster for ectopic expression of multiplexed anti-HIV RNAs." Gene Ther (2008); 15: 1536-1549.

Bauer et al., "Prevention of interferon-stimulated gene expression using microRNA-designed hairpins." Gene Ther. (2009); 16: 142-147.

Baulcombe, "Diced defence." Nature.Jan. 18, 2001; 409(6818):295-6.

Biesecker et al, "Derivation of RNA aptamer inhibitors of human complement C5." Immunopharmacology (1999) vol. 42, Issue 1-3, pp. 219-30.

Boiziau et al. "DNA Aptamers Selected Against the HIV-1 trans-Activationresponsive Rna Element Form RNA-DNA Kissing Complexes." Journal of biological chemistry (1999); 274(18): 12730-12737.

Boiziau et al., "Identification of Aptamers Against the DNA Template for in Vitro Transcription of the HIV-1 TAR Element." Antisense Nucleic Acid Drug Dev. (1997); 7(4): 369-80.

Boudreau et al., "Artificial microRNAs as siRNA shuttles: improved safety as compared to shRNAs in vitro and in vivo." Mol. Ther. (2009); 17(1): 169-175.

Brockstedt et al., "In vitro evolution of RNA aptamers recognizing carcinogenic aromatic amines." Biochem. Biophys. Res. Commun. (2004) vol. 313, Issue 4, pp. 1004-1008.

Burke et al., "RNA aptamers to the adenosine moiety of S-adenosyl methionine: structural inferences from variations on a theme and the reproducibility of SELEX." Nucleic Acids Research (1997); 25(10): 2020-2024.

Cai et al., "Human microRNAs are processed from capped, polyadenylated transcripts that can also function as mRNAs." RNA (2004); 10: 1957-1966.

Daniels, "A tenascin-C aptamer identified by tumor cell SELEX: Systematic evolution of ligands by exponential enrichment." PNAS (2003); 100(26): 15416-15421.

Eulberg et al., "Development of an automated in vitro selection protocol to obtain RNA-based aptamers: identification of a biostable substance P antagonist." Nucleic Acids Res. (2005); 33(4): e45.

Flinders et al., "Recognition of planar and nonplanar ligands in the malachite green-RNA aptamer complex." Chembiochem (2004) vol. 5, Issue I, pp. 62-72.

Friedman et al., "Most mammalian mRNAs are conserved targets of microRNAs." Genome Res. (2009); 19: 92-105.

Fukusaki et al., "DNA aptamers that bind to chitin." Bioorg. Med. Chem. Lett. (2000) vol. 10, Issue 5, pp. 423-425.

Gebhardt, "RNA aptamers to s-adenosylhomocysteine: kinetic properties, divalent cation dependency, and comparison with anti-s-adenosylhomocysteine antibody." Biochemistry (2000) vol. 39, Issue 24, pp. 7255-7265.

Gilbert et al., "RNA aptamers that specifically bind to a K Ras-derived farnesylated peptide." Bioorg. Med. Chem. (1997) vol. 5, Issue 6, pp. 1115-1122.

Gopinath et al., "An efficient RNA aptamer against human influenza B virus hemagglutinin." J Biochem (Tokyo) (2006) vol. 139, Issue 5, pp. 837-846.

Gregory et al., "The Microprocessor complex mediates the genesis of microRNAs." Nature (2004). 432, 235-240.

Guil et al., "The multifunctional RNA-binding protein hnRNP A1 is required for processing of miR-18a." Nat Struct Mol Biol (2007). 14: 591-596.

Haller et al., "In vitro selection of a 7-methyl-guanosine binding RNA that inhibits translation of capped mRNA molecules." PNAS (1997); 94: 8521-8526.

Hammond et al., "Argonaute2, a Link Between Genetic and Biochemical Analyses of RNAi." Science. Aug. 10, 2001; 293(5532): 1146-1150.

Han et al., "Molecular basis for the recognition of primary microRNAs by the Drosha-DGCR8 complex." Cell (2006); 125: 887-901.

Han et al., "The Drosha-DGCR8 complex in primary microRNA processing." Genes Dev (2004); 18: 3016-3027.

Han et al., "Posttranscriptional crossregulation between Drosha and DGCR8." Cell (2009); 136: 75-84.

Hesselberth et al., "In Vitro Selection of RNA Molecules That Inhibit the Activity of Ricin A-chain." Journal of Biological Chemistry (2000); 275(7): 4937-4942.

Hicke et al., "Tenascin-C Aptamers Are Generated Using Tumor Cells and Purified Protein." J. Biol. Chem. (2001); 276(52): 48644-4854.

Hirao et al., "RNA Aptamers That Bind to and Inhibit the Ribosome-inactivating Protein, Pepocin." Journal of Biological Chemistry (2000); 275(7): 4943-4948.

Hornung et al., "In vitro selected RNA molecules that bind to elongation factor tu." Biochemistry (1998) vol. 37, Issue, pp. 7260-7267.

Jeong et al., "In vitro selection of the RNA aptamer against the sialyl lewis x and its inhibition of the cell adhesion." Biochemical and Biophysical Research Communications (2001) vol. 281, Issue I, pp. 237-243.

Kato et al., "In vitro selection of DNA aptamers which bind to cholic acid." Biochim. Biophys. Acta (2000) vol. 1493, Issue 1-2, pp. 12-18.

Kedde et al., "RNA-binding protein Dnd1 inhibits microRNA access to target mRNA." Cell (2007); 131: 1273-1286.

Kimoto et al., "Anti-(Raf-1) RNA aptamers that inhibit Ras-induced Raf-1 activation." Eur. J. Biochem. (2002); 269(2): 697-704.

Kimoto et al., "RNA aptamers that specifically bind to the Ras-binding domain of Raf-1." FEBS Lett. (1998); 441(2): 322-326.

Koizumi et al., "Molecular recognition of cAMP by an RNA aptamer." Biochemistry (2000) vol. 39, Issue 30, pp. 8983-8992.

Zeng et al., "Recognition and cleavage of primary microRNA precursors by the nuclear processing enzyme Drosha." EMBO J. (2005); 24: 138-148.

Kraus et al, "Cutting Edge: Novel RNA Ligands Able to Bind CD4 Antigen and Inhibit CD4+T Lymphocyte Function." J. Immunol. (1998); 160(II): 5209-5212.

Lee et al., "The nuclear RNase III Drosha initiates microRNA processing." Nature (2003) 425:415-419.

Lee et al., "In vitro and in vivo assays for the activity of Drosha complex." Methods Enzymol (2007).427: 89-106.

Lee et al., "MicroRNA maturation: stepwise processing and subcellular localization." EMBO J. (2002); 21(17): 4663-4670.

Legiewicz et al., "A More Complex Isoleucine Aptamer with a Cognate Triplet." J. Biol. Chem. (2005); 280(20): 19815-19822.

Liu, et al., "RNA aptamers specific for bovine thrombin." Journal of Molecular Recognition (2003) vol. 16, Issue 1, pp. 23-27.

Lozupone et al., "Selection of the simplest RNA that binds isoleucine." RNA (2003); 9(II): 1315-22.

Misono et al. "Selection of RNA aptamers against human influenza virus hemagglutinin using surface plasmon resonance." Anal. Biochem. (2005) vol. 342, Issue 2, pp. 312-317.

Muller et al., "Thermodynamic characterization of an engineered tetracycline-binding riboswitch." Nucleic Acids Res (2006); 34(9): 2607-2617.

Osborne et al., "Nucleic Acid Selection and the Challenge of Combinatorial Chemistry." Chem. Rev (1997). 97: 349-370.

Roychowdhury-Saha et al., "Flavin recognition by an RNA aptamer targeted toward FAD." Biochemistry (2002) vol. 41, Issue 8, pp. 2492-2499.

Ruckman, et al., "2'-Fluoropyrimidine RNA-based Aptamers to the 165-Amino Acid Form of Vascular Endothelial Growth Factor (VEGF165)." J. Biol. Chem. (1998); 273(32): 20556-20567.

Saran et al., "The tyranny of adenosine recognition among RNA aptamers to coenzyme A." BMC Evol. Biol. (2003); 3(I): 26.

Schneider et al, "Selective enrichment of RNA species for tight binding to *Escherichia coli* rho factor." FASEB J. (1993) 7(I): 201-207.

Sontheimer, "Assembly and Function of Rna Silencing Complexes." Nat Rev Mol Cell Biol. Feb. 2005; 6(2):127-38.

Stern et al., "A system for Cre regulated RNA interference in vivo." Proc Natl Acad Sci USA (2008); 105,13895-13900.

Sun et al., "Multi-miRNA hairpin method that improves gene knockdown efficiency and provides linked multi-gene knockdown." Biotechniques (2006); 41: 59-63.

Tahiri-Alaoui et al., "High affinity nucleic acid aptamers for strptavidin incorporated into bi-specific capture ligands." Nucleic Acids Res. (2002); 30(10): e45.

Takeno et al., "Selection of an RNA Molecual That Specifically Inhibits the Protease Activity of Subtilisin." Journal of Biochemistry (1999); 125(6): 1115-1119.

Tao et al., "Arginine-binding RNAs resembling tar identified by in vitro selection." Biochemistry (1996) vol. 35, Issue 7, pp. 2229-2238.

Rusconi et al., "Blocking the initiation of coagulation by RNA aptamers to factor VIIa." Thromb Haemost. (2000) vol. 84, Issue 5, pp. 841-848.

Tuerk et al., "RNA pseudoknots that inhibit human immunodeficiency virus type 1 reverse transcriptase." Proc Natl Acad Sci USA (1992); 89:6988-6992.
Tuleuova et al., "Modulating endogenous gene expression of mammalian cells via RNA-small molecule interaction." Biochem Biophys Res Commun (2008); 376: 169-173.
Ulrich et al., "In vitro selection of RNA molecules that displace cocaine from the membrane-bound nicotinic acetylcholine receptor." Proc. Natl. Acad. Sci. USA (1998); 95(24): 14051-14056.
Urvil et al., "Selection of RNA aptamers that bind specifically to the NS3 protease of hepatitis C virus." European Journal of Biochemistry (1997); 248(I): 130-138.
Vaish et al., "A novel, modification-dependent ATP-binding aptamer selected from an RNA library incorporating a cationic functionality." Biochemistry (2003) vol. 42, Issue 29, pp. 8842-8851.
Wallace et al., "In vitro selection and characterization of streptomycin-binding RNAs: Recognition discrimination between antibiotics." RNA (1998); 4(I): 112-123.
Wang et al., "RNA molecules that specifically and stoichiometrically bind aminoglycoside anitibiotics with high affinities." Biochemistry (1996) vol. 35, Issue 38, pp. 12338-12346.
Wang et al., "Recent patents on the identification and clinical application of microRNAs and target genes." Recent Pat DNA Gene Seq (2007). 1: 116-124.
Wang et al., "MicroRNA-based therapeutics for cancer." BioDrugs (2009). 23:15-23.
Weigand et al., "Screening for engineered neomycin riboswitches that control translation initiation." RNA (2008); 14: 89-97.
Wieland et al., "Artificial ribozyme switches containing natural riboswitch aptamer domains." Angew Chem Int Ed Eng (2009). 148: 2715-2718.
Wilson et al., "Functional requirements for specific ligand recognition by a biotin-binding RNA pseudoknot." Biochemistry (1998); 37: 14410-14419.
Xia et al., "Multiple shRNAs expressed by an inducible pot II promoter can knock down the expression of multiple target genes." Biotechniques (2006); 41: 64-68.
Yang et al., "DNA ligands that bind tightly and selectively to cellobiose." PNAS (1998); 95(10): 5462-5467.
Yeom et al., "Characterization of DGCR8/Pasha, the essential cofactor for Drosha in primary miRNA processing." Nucleic Acids Res. 2006; 34(16):4622-4629. Epub Sep. 8, 2006.
Zeng et al., "Sequence requirements for micro RNA processing and function in human cells." RNA (2003); 9: 112-123.
Zeng et al., "Efficient processing of primary microRNA hairpins by Drosha requires flanking nonstructured RNA sequences." J Biol Chem (2005); 280: 27595-27603.
Zeng et al., "Both natural and designed micro RNAs can inhibit the expression of cognate mRNAs when expressed in human cells." Mol Cell (2002); 9: 1327-1333.
Wieland M., et al., "Artificial riboswitches: synthetic mRNA-based regulators of gene expression." Chembiochem. 2008; 9:1873-1878.
Novina CD, et al., "The RNAi revolution." Nature. 2004; 430(6996):161-164.
Fedor MJ, et al., "The catalytic diversity of RNAs." Nat Rev Mol Cell Biol. 2005; 6:399-412.
Breaker RR. "Complex riboswitches." Science. 2008; 319:1795-1797.
Wilson DS, et al., "In vitro selection of functional nucleic acids." Annu Rev Biochem. 1999; 68:611-647.
Blattman JN, et al., "Cancer immunotherapy: a treatment for the masses." Science 2004; 305:200-205.
Shankaran V, et al., "IFNgamma and lymphocytes prevent primary tumour development and shape tumour immunogenicity." Nature. 2001; 410:1107-1111.
Morgan RA, et al., "Cancer regression in patients after transfer of genetically engineered lymphocytes." Science. 2006; 314:126-129.
Robbins PR, et al., "Cutting edge: persistence of transferred lymphocyte clonotypes correlates with cancer regression in patients receiving cell transfer therapy." J. Immunol. 2004; 173:7125-7130.
Leen AM, et al., "Improving T cell therapy for cancer." Annu Rev Immunol. 2007; 25:243-265.

Riddell SR, et al., "Restoration of viral immunity in immunodeficient humans by the adoptive transfer of T cell clones." Science. 1992; 257:238-241.
Comoli P, et al., "T cell therapy of Epstein-Barr virus and adenovirus infections after hemopoietic stem cell transplant." Blood Cells Mol Dis. 2008; 40:68-70.
June CH. "Principles of adoptive T cell cancer therapy." J Clin Invest. 2007; 117:1204-1212.
Rosenberg SA, et al., "Gene transfer into humans-immunotherapy of patients with advanced melanoma, using tumor-infiltrating lymphocytes modified by retroviral gene transduction." N Engl J Med. 1990; 323:570-578.
Kahlon KS, et al., "Specific recognition and killing of glioblastoma multiforme by interleukin 13-zetakine redirected cytolytic T cells." Cancer Res. 2004; 64:9160-9166.
Huang J, et al., "Survival, persistence, and progressive differentiation of adoptively transferred tumor-reactive T cells associated with tumor regression." J Immunother. 2005; 28:258-267.
Dudley ME, et al., "Adoptive transfer of cloned melanoma-reactive T lymphocytes for the treatment of patients with metastatic melanoma." J Immunother. 2001; 24:363-373.
Yee C, et al.., "Adoptive T cell therapy using antigen-specific CD8+ T cell clones for the treatment of patients with metastatic melanoma: in vivo persistence, migration, and antitumor effect of transferred T cells." Proc Natl Acad Sci USA. 2002; 99:16168-16173.
Mackensen A., et al., "Phase I study of adoptive T-cell therapy using antigen-specific CD8+ T cells for the treatment of patients with metastatic melanoma." J Clin Oncol. 2006; 24:5060-5069.
Johnston JA, et al., "Tyrosine phosphorylation and activation of STATS, STAT3, and Janus kinases by interleukins 2 and 15." Proc Natl Acad Sci USA. 1995; 92:8705-8709.
Gattinoni L, et al., "Adoptive immunotherapy for cancer: building on success." Nat Rev Immunol. 2006; 6:383-393.
Hsu C, et al., "Primary human T lymphocytes engineered with a codon-optimized IL-15 gene resist cytokine withdrawal-induced apoptosis and persist long-term in the absence of exogenous cytokine." J Immunol. 2005; 175:7226-7234.
Waldmann T, et al., "Contrasting roles of IL-2 and IL-15 in the life and death of lymphocytes: implications for immunotherapy." Immunity. 2001; 14:105-110.
Berger C, et al., "Adoptive transfer of effector CD8+ T cells derived from central memory cells establishes persistent T cell memory in primates." J Clin Invest. 2008; 118:294-305.
Falkenburg JH, et al., "Cytotoxic T-lymphocyte (CTL) responses against acute or chronic myeloid leukemia." Immunol Rev. 1997; 157:223-230.
Walter EA, et al., "Reconstitution of cellular immunity against cytomegalovirus in recipients of allogeneic bone marrow by transfer of T-cell clones from the donor." N Engl J Med. 1995; 333:1038-1044.
Gonzalez S, et al., "Genetic engineering of cytolytic T lymphocytes for adoptive T-cell therapy of neuroblastoma." J Gene Med. 2004; 6:704-711.
Giepmans, et al., "The fluorescent toolbox for assessing protein location and function." Science. 2006; 312:217-224.
Introna M, et al., "Genetic modification of human T cells with CD19: A strategy to purify and lyse transduced cells with anti-CD20 antibodies." Human Gene Therapy. 2004; 11(4):611-620.
Gillis S, et al., "Long term culture of tumour-specific cytotoxic T cells." Nature. 1977; 268:154-156.
Blau CA, et al., "A proliferation switch for genetically modified cells." Proc Natl Acad Sci USA 1997; 94:3076-3081.
Neff T, et al., "Pharmacologically regulated in vivo selection in a large animal." Blood 2002; 100:2026-2031.
Kim et al., "An artificial riboswitch for controlling pre-mRNA splicing." RNA (2005) 11:1667-1677.
Wang et al., "General and Specific Functions of Exonic Splicing Silencers in Splicing Control." Molecular Cell (2006) 23: 61-70.
Villemaire et al., "Reprogramming Alternative Pre-messenger RNA Splicing through the Use of Protein-binding Antisense Oligonucleotides." Biol. Chem. (2003). 278(50): 50031-50039.

* cited by examiner

SEQUENCE LISTING

<160> NUMBER OF SEQ ID NOS: 30

<210> SEQ ID NO 1
<211> LENGTH: 47
<212> TYPE: DNA
<213> ORGANISM: Artificial Sequence
<220> FEATURE:
<223> OTHER INFORMATION: Primer

<400> SEQUENCE: 1
atcggatccg ccgccaccat ggaggatgcc aagaatatta agaaagg         47

<210> SEQ ID NO 2
<211> LENGTH: 37
<212> TYPE: DNA
<213> ORGANISM: Artificial Sequence
<220> FEATURE:
<223> OTHER INFORMATION: Primer

<400> SEQUENCE: 2
tattctagat cagtcctgct cctctgccac aaagtgc                    37

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
attgctgagc ctagagctga ag                                    22

<210> SEQ ID NO 4
<211> LENGTH: 40
<212> TYPE: DNA
<213> ORGANISM: Artificial Sequence
<220> FEATURE:
<223> OTHER INFORMATION: Primer

<400> SEQUENCE: 4
cccgcagtag cgtgggcatt cttttcctcc tcaggaccag                 40

<210> SEQ ID NO 5
<211> LENGTH: 40
<212> TYPE: DNA
<213> ORGANISM: Artificial Sequence
<220> FEATURE:
<223> OTHER INFORMATION: Primer

<400> SEQUENCE: 5
ctggtcctga ggaggaaaag aatgcccacg ctactgcggg                 40

<210> SEQ ID NO 6
<211> LENGTH: 39
<212> TYPE: DNA
<213> ORGANISM: Artificial Sequence
<220> FEATURE:
<223> OTHER INFORMATION: Primer

<400> SEQUENCE: 6
cctctccgcc gccagatctg ttagcctccc ccatctccc                  39

```
<210> SEQ ID NO 7
<211> LENGTH: 39
<212> TYPE: DNA
<213> ORGANISM: Artificial Sequence
<220> FEATURE:
<223> OTHER INFORMATION: Primer

<400> SEQUENCE: 7
gggagatggg ggaggctaac agatctggcg gcggagagg                    39

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tctcggtgta cagggtggcg                                         20

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
cttggtaccc gccaccatgg tgagcaag                                28

<210> SEQ ID NO 10
<211> LENGTH: 67
<212> TYPE: DNA
<213> ORGANISM: Artificial Sequence
<220> FEATURE:
<223> OTHER INFORMATION: Primer

<400> SEQUENCE: 10
ccacgtcacc gcatgttaga agacttcctc tgccctctcc gctgcccttg tacagctcgt    60
ccatgcc                                                             67

<210> SEQ ID NO 11
<211> LENGTH: 62
<212> TYPE: DNA
<213> ORGANISM: Artificial Sequence
<220> FEATURE:
<223> OTHER INFORMATION: Primer

<400> SEQUENCE: 11
cttctaacat gcggtgacgt ggaggagaat cccggcccta tgtacaggat gcaactcctg    60
tc                                                                  62

<210> SEQ ID NO 12
<211> LENGTH: 32
<212> TYPE: DNA
<213> ORGANISM: Artificial Sequence
<220> FEATURE:
<223> OTHER INFORMATION: Primer

<400> SEQUENCE: 12
agactcgagt caagttagtg ttgagatgat gc                           32
```

```
<210> SEQ ID NO 13
<211> LENGTH: 49
<212> TYPE: DNA
<213> ORGANISM: Artificial Sequence
<220> FEATURE:
<223> OTHER INFORMATION: Primer

<400> SEQUENCE: 13
aatagttaac gttgacattg attattgact agttattaat agtaatcaa        49

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
aataccgcgg ccatagagcc caccgc                                 26

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
aatagatatc tgcttcgcga ggatctgc                               28

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
aataggtacc ggtggcggcg ctag                                   24

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
aatactcgag gcgatcgcaa acaaacaaa                              29

<210> SEQ ID NO 18
<211> LENGTH: 53
<212> TYPE: DNA
<213> ORGANISM: Artificial Sequence
<220> FEATURE:
<223> OTHER INFORMATION: Primer

<400> SEQUENCE: 18
aatagggccc aagattaatt aaaaaaaaaa tttttatttt tcttttgct gtt    53

<210> SEQ ID NO 19
<211> LENGTH: 18
<212> TYPE: DNA
<213> ORGANISM: Artificial Sequence
<220> FEATURE:
<223> OTHER INFORMATION: Primer
```

-continued

```
<400> SEQUENCE: 19
tgctgccatt gtcgaaca                                                    18

<210> SEQ ID NO 20
<211> LENGTH: 16
<212> TYPE: DNA
<213> ORGANISM: Artificial Sequence
<220> FEATURE:
<223> OTHER INFORMATION: Primer

<400> SEQUENCE: 20
ggtgtcgtgg atgctg                                                      16

<210> SEQ ID NO 21
<211> LENGTH: 15
<212> TYPE: DNA
<213> ORGANISM: Artificial Sequence
<220> FEATURE:
<223> OTHER INFORMATION: Primer

<400> SEQUENCE: 21
agccagcgaa gccac                                                       15

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
caactgggtg aacgtgat                                                    18

<210> SEQ ID NO 23
<211> LENGTH: 59
<212> TYPE: DNA
<213> ORGANISM: Artificial Sequence
<220> FEATURE:
<223> OTHER INFORMATION: T2A DNA

<400> SEQUENCE: 23
ggcagcggag agggcagagg aagtcttcta acatgcggtg acgtggagga gaatcccgg       59

<210> SEQ ID NO 24
<211> LENGTH: 20
<212> TYPE: PRT
<213> ORGANISM: Artificial Sequence
<220> FEATURE:
<223> OTHER INFORMATION: T2A Peptide

<400> SEQUENCE: 24

Gly Ser Gly Glu Gly Arg Gly Ser Leu Leu Thr Cys Gly Asp Val Glu
  1               5                  10                  15

Glu Asn Pro Gly
            20

<210> SEQ ID NO 25
<211> LENGTH: 102
<212> TYPE: DNA
<213> ORGANISM: Artificial Sequence
<220> FEATURE:
<223> OTHER INFORMATION: sTRSV hammerhead ribozyme
```

```
<400> SEQUENCE: 25
ctcgagaaac aaacaaagct gtcaccggat gtgctttccg gtctgatgag tccgtgagga    60
cgaaacagca aaagaaaaa taaaaatttt ttggaatcta ga                       102

<210> SEQ ID NO 26
<211> LENGTH: 162
<212> TYPE: DNA
<213> ORGANISM: Artificial Sequence
<220> FEATURE:
<223> OTHER INFORMATION: L2bulge1

<400> SEQUENCE: 26
ctcgaggcga tcgcaaacaa acaaagctgt caccggatgt gctttccggt ctgatgagtc    60
cgtgtccata ccagcatcgt cttgatgccc ttggcaggga cgggacgagg acgaaacagc   120
aaaaagaaaa ataaaaattt ttttttaat taatcttggg cc                       162

<210> SEQ ID NO 27
<211> LENGTH: 165
<212> TYPE: DNA
<213> ORGANISM: Artificial Sequence
<220> FEATURE:
<223> OTHER INFORMATION: L2bulge8

<400> SEQUENCE: 27
ctcgaggcga tcgcaaacaa acaaagctgt caccggatgt gctttccggt ctgatgagtc    60
cgttgtccat accagcatcg tcttgatgcc cttggcaggg acgggacgga ggacgaaaca   120
gcaaaaagaa aataaaaat tttttttta attaatcttg ggccc                     165

<210> SEQ ID NO 28
<211> LENGTH: 168
<212> TYPE: DNA
<213> ORGANISM: Artificial Sequence
<220> FEATURE:
<223> OTHER INFORMATION: L2bulge9

<400> SEQUENCE: 28
ctcgaggcga tcgcaaacaa acaaagctgt caccggatgt gctttccggt ctgatgagtc    60
cgttgtccaa taccagcatc gtcttgatgc ccttggcagt ggatggggac ggaggacgaa   120
acagcaaaaa gaaaaataaa aattttttttt ttaattaatc ttgggccc               168

<210> SEQ ID NO 29
<211> LENGTH: 175
<212> TYPE: DNA
<213> ORGANISM: Artificial Sequence
<220> FEATURE:
<223> OTHER INFORMATION: L2bulge18tc

<400> SEQUENCE: 29
ctcgaggcga tcgcaaacaa acaaagctgt caccggatgt gctttccggt ctgatgagtc    60
cgttgtccaa aacataccag atttcgatct ggagaggtga agaattcgac cacctggacg   120
aggacggagg acgaaacagc aaaaagaaaa ataaaaatta attaatcttg ggccc        175

<210> SEQ ID NO 30
<211> LENGTH: 120
<212> TYPE: DNA
<213> ORGANISM: Artificial Sequence
<220> FEATURE:
<223> OTHER INFORMATION: Inactive ribozyme
```

```
<400> SEQUENCE: 30
ctcgaggcga tcgcaaacaa acaaagctgt caccggatgt gctttccggt acgtgaggtc    60
cgtgaggaca gaacagcaaa aagaaaaata aaattttttt ttttaattaa tcttgggccc   120
```

GENETIC CONTROL OF MAMMALIAN CELLS WITH SYNTHETIC RNA REGULATORY SYSTEMS

CROSS-REFERENCE TO RELATED APPLICATIONS

This application claims priority from U.S. Provisional No. 61/207,900, filed Feb. 18, 2009, the contents of which application is incorporated herein by reference in its entirety.

REFERENCE TO SEQUENCE LISTING, TABLE, OR COMPUTER PROGRAM LISTING

The present application is being filed along with a Sequence Listing in electronic format. The Sequence Listing is provided as a file entitled 2010-02-18_SEQ_LIST_CALTE-057A.txt, created Feb. 18, 2010, which is 6308 bytes in size. The information in the electronic format of the Sequence Listing is incorporated herein by reference in its entirety.

BACKGROUND OF THE INVENTION

1. Field of the Invention

The present application relates to a system for controlling gene expression of gene products that affect cell fate determination in mammalian cells in response to an endogenous or exogenous ligand.

2. Background

The control of expression of genes introduced into mammalian cells is of great interest for a variety of applications including gene therapy and cellular immunotherapeutics.

Cellular immunotherapeutics is an active area of research seeking to harness and improve the capabilities of the immune system to combat various diseases, most prominently cancer. Research in the last decade has demonstrated that the natural immune system is central to the defense against tumorigenic malignancies in immunocompetent individuals (Blattman, J. N. & Greenberg, P. D. Cancer immunotherapy: a treatment for the masses. Science 305, 200-205 (2004); Shankaran, V. et al. IFNgamma and lymphocytes prevent primary tumour development and shape tumour immunogenicity. Nature 410, 1107-1111 (2001)). T cells with both natural and synthetic receptors for tumor-associated antigens have been shown to have tumor specific targeting and cytolytic activities (Morgan, R. A. et al. Cancer regression in patients after transfer of genetically engineered lymphocytes. Science 314, 126-129 (2006); Robbins, P. F. et al. Cutting edge: persistence of transferred lymphocyte clonotypes correlates with cancer regression in patients receiving cell transfer therapy. J. Immunol. 173, 7125-7130 (2004); Leen, A. M., Rooney, C. M. & Foster, A. E. Improving T cell therapy for cancer. Annu Rev Immunol 25, 243-265 (2007)). Compared to conventional cancer treatments such as radiation and chemotherapy, cellular immunotherapeutics significantly reduces off-target effects and the associated non-specific toxicity to healthy tissues. The promise of a new treatment paradigm with improved safety and efficacy has driven the development of various cellular immunotherapeutic strategies.

As an example, the adoptive transfer of antigen-specific T cells can reconstitute immunity to viruses and virus-induced malignancy and be therapeutically effective in humans (Riddell, S. R. et al. Restoration of viral immunity in immunodeficient humans by the adoptive transfer of T cell clones. Science 257, 238-241 (1992); Comoli, P. et al. T cell therapy of Epstein-Barr virus and adenovirus infections after hemopoietic stem cell transplant. Blood Cells Mol Dis 40, 68-70 (2008); June, C. H. Principles of adoptive T cell cancer therapy. *J Clin Invest* 117, 1204-1212 (2007)). The identification of tumor antigens and improvements in gene transfer methodology has made it feasible to isolate tumor-reactive T cells or to engineer T cells to express receptors that target transformed cells (Rosenberg, S. A. et al. Gene transfer into humans—immunotherapy of patients with advanced melanoma, using tumor-infiltrating lymphocytes modified by retroviral gene transduction. N Engl J Med 323, 570-578 (1990); Kahlon, K. S. et al. Specific recognition and killing of glioblastoma multiforme by interleukin 13-zetakine redirected cytolytic T cells. Cancer Res 64, 9160-9166 (2004)). Regression of advanced tumors has been observed in a subset of melanoma patients treated with T cells specific for melanocyte differentiation antigens (Morgan (2006); Huang, J. et al. Survival, persistence, and progressive differentiation of adoptively transferred tumor-reactive T cells associated with tumor regression. J Immunother (1997) 28, 258-267 (2005)), but therapy often fails or induces only a temporary response. Limitations in T-cell therapy include the inability of transferred tumor-specific T cells to persist in the tumor-bearing host (Rosenberg (1990); Dudley, M. E. et al. Adoptive transfer of cloned melanoma-reactive T lymphocytes for the treatment of patients with metastatic melanoma. J Immunother 24, 363-373 (2001); Yee, C. et al. Adoptive T cell therapy using antigen-specific CD8+ T cell clones for the treatment of patients with metastatic melanoma: in vivo persistence, migration, and antitumor effect of transferred T cells. Proc Natl Acad Sci USA 99, 16168-16173 (2002); Mackensen, A. et al. Phase I study of adoptive T-cell therapy using antigen-specific CD8+ T cells for the treatment of patients with metastatic melanoma. J Clin Oncol 24, 5060-5069 (2006).). Therefore, genetic systems that allow for tight, tunable, and regulatable control over the proliferation and activation of T cells are critical to the practical application of therapies based on engineering of immune system function.

SUMMARY OF THE INVENTION

In some aspects, a system for controlling the expression of a gene product in a mammalian cell is provided.

In one aspect, the system includes a nucleic acid encoding a gene product that affects a cell fate decision of a mammalian cell, and a RNA switch nucleic acid domain comprising a sensor domain and an actuator domain. The sensor domain is configured to bind to a ligand and the actuator domain modulates expression of the gene product. Binding of the ligand to the sensor domain modulates the functional activity of the actuator domain modulating the expression of the gene product.

In one embodiment, the system has more than one RNA switch nucleic acid domain. The sensor domains of each RNA switch nucleic acid domain bind to the same ligand or to different ligands. Multiple copies of the same switch domain can be used to enhance the stringency of the system.

In yet another aspect of the invention, the cell fate decision of the cell that is modulated by the gene product is activation, proliferation, apoptosis or differentiation of the mammalian cell.

In another aspect of the invention, the actuator domain is a ribozyme. The ribozyme can be any ribozyme, including a hammerhead ribozyme. The ribozyme can influence translation of the nucleic acid encoding a gene product, by for example, cleaving the 3' untranslated region of a RNA of a transcribed nucleic acid. A ribozyme actuator can be coupled to a sensor domain such that the ribozyme cleaves a RNA molecule in the presence of the ligand, or can be designed so that the ribozyme cleaves in the absence of the ligand and the ligand inhibits cleavage.

In yet another aspect of the invention, various ligands can be used that bind to the sensor domain. The ligand can be a molecule endogenous to the cell or one exogenous. In one embodiment, the ligand is an endogenous polypeptide, peptide, nucleic acid, carbohydrate, fatty acid, lipid, non-peptide hormone, or metabolic precursor or product thereof. In yet another embodiment, the ligand is an exogenous small organic molecule having a molecular weight less than about 2.5 kDa. In yet another embodiment, the ligand has a molecular weight of less than about 1 kDa. In yet another embodiment, the ligand is a cell permeable molecule. In various embodiments, the ligand can be theophylline, tetracycline, phenobarbital, tamoxifen, folinic acid or vitamin B12.

In one aspect of the invention, the gene product encoded by the nucleic acid encodes a RNA or protein that modulates a cell fate decision of a mammalian cell. When the gene product is a RNA, it can encode any RNA that can modulate the cell fate decision, including a small interfering RNA (siRNA), a micro RNA (miRNA) or a ribozyme.

In another aspect, the gene product is a protein. The protein can be any protein that modulates the cell fate decision in the mammalian cell. In one embodiment, the protein is a growth factor. In another embodiment, the system encodes a gene product that is a cytokine. In various embodiments, the cytokine is IL-2, IL-4, IL-7, IL-9 or IL-15. In other embodiments, the gene product can include a cytokine receptor or cytokine-cytokine receptor fusion.

In yet another aspect, the system can include nucleic acids that encode a marker protein that enables detection of the marker protein. In one embodiment the nucleic acid encodes a fluorescent protein.

In yet another aspect, the system also includes a safety protein. The safety protein allows killing of a cell harboring the system of the invention. In one embodiment, the safety protein can be thymidylate kinase, which allows killing of cells expressing it, by treating the cells with ganciclovir.

In yet another aspect, the system includes a nucleic acid that encodes a T-cell receptor protein. In one embodiment, the T-cell receptor nucleic acid is the same nucleic acid encoding the gene product. In another embodiment, the T-cell receptor nucleic acid is a different nucleic acid from the nucleic acid encoding the gene product.

The system can be used with a variety of mammalian cells, both in vitro and in vivo. In one aspect of the invention, the system is used with lymphocytes. In one embodiment, the system is used with T cells.

In yet another aspect, a cell includes a nucleic acid encoding a gene product that affects a cell fate decision of a mammalian cell, and a RNA switch nucleic acid domain comprising a sensor domain and an actuator domain. The sensor domain is configured to bind to a ligand and the actuator domain modulates expression of the gene product. Binding of the ligand to the sensor domain modulates the functional activity of the actuator domain modulating the expression of the gene product. In one embodiment, the cell is a bacterial cell. Bacterial cells with such nucleic acids are useful, among other uses, for making, modifying and transporting a nucleic acid. In another embodiment, the cell is a eukaryotic cell. In yet another embodiment, the cell is a mammalian cell. In yet another embodiment, the cell is a mammalian T cell. In yet another embodiment, the cell is a human T cell. When the cell is a human T cell, the cell may also include a nucleic acid encoding a T-cell receptor. In one such embodiment, the T-cell receptor binds a tumor-associated antigen.

In yet another aspect of the invention, a method of affecting a cell fate decision of a mammalian cell is provided. In one embodiment, a method includes affecting the proliferation of a T cell in a mammal, by providing to a mammal, a mammalian cell including a nucleic acid regulatory system encoding a gene product that affects proliferation or activation of a mammalian cell; and a RNA switch nucleic acid domain comprising a sensor domain and an actuator domain. The sensor domain is configured to bind to a ligand and the actuator domain modulates expression of the gene product. Binding of the ligand to the sensor domain modulates the functional activity of the actuator domain thereby modulating the expression of the gene product. In one embodiment, method includes a ligand that is an endogenous ligand. In another aspect, the ligand is provided to the mammal. In yet another aspect of the invention, the mammal is a human. In one embodiment, the ligand is provided orally, intravenously, or intramuscularly to a human, in an amount effective to affect a cell fate decision of a cell having a nucleic acid regulatory system.

BRIEF DESCRIPTION OF THE DRAWINGS

FIG. 2a shows a schematic view of a modular RNA switch with one or two RNA switches per nucleic acid.

FIG. 2b shows a graph of cell viability levels for nucleic acid constructs encoding theophylline-responsive switches (L2bulge 1, 8, 9) in one (1×), two (2×), three (3×), and four (4×) copies through transient transfections in CTLL-2 cells grown in 0 and 1 mM theophylline. No IL-2 Control, construct not encoding a proliferative cytokine; sTRSV Ribozyme, construct encoding a non-switch hammerhead ribozyme.

FIG. 2c shows a graph of cell viability levels for the L2bulge9 regulatory systems at various theophylline concentrations.

FIG. 2d shows a schematic of a nucleic acid construct having a target transgene or gene product (cd19-tk-t2a-il15) encoding a fusion of a membrane-bound reporter protein (CD19), selection marker (TK), and growth cytokine (IL-15) that was tested in the L2bulge9 regulatory systems.

FIG. 2e shows a graph of cell viability based on the cd19-tk-t2a-il15 target transgene exhibiting an enhanced survival response with increasing ligand concentrations.

FIG. 2f shows a schematic of a nucleic acid construct having a tetracycline-responsive ribozyme switch in place of the theophylline-responsive switch shown in FIG. 1a.

FIG. 2g shows a graph of gene product expression in cells having a tetracycline-dependent RNA switch over various concentrations of tetracycline.

DETAILED DESCRIPTION

Figure 1:
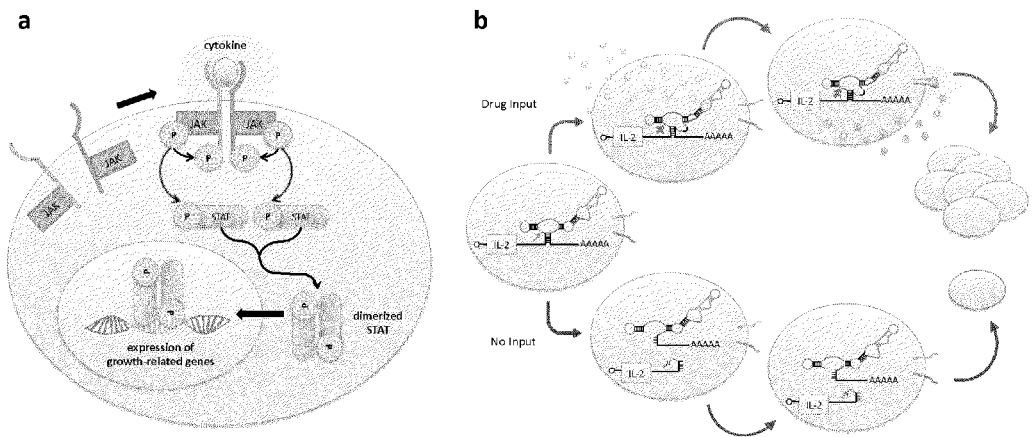
FIG. 1a shows a schematic view of the cytokine mediated cell signaling.
FIG. 1b shows a schematic of IL-2 expression under the control of a RNA switch.

The present disclosure provides a variety of systems for controlling expression of a gene product that affects cell fate decisions in a mammalian cell, and methods for using such systems. The systems are synthetic, RNA-based systems. The systems can exhibit titratable control, and do not rely on immunogenic protein-based regulatory components.

The systems have a modular framework. This property allows for rapid and effective tailoring of the regulatory system to clinically applicable pharmaceutical inputs and diverse applications through the direct replacement of sensor and target gene product components. Further, the systems can be rationally tuned. This property allows for efficient tuning of the regulatory stringency of the control system.

DEFINITIONS

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques of described herein are those well known and commonly used in the art.

As utilized in accordance with the embodiments provided herein, the following terms, unless otherwise indicated, shall be understood to have the following meanings:

The term "nucleic acid" refers to natural nucleic acids, artificial nucleic acids, non-natural nucleic acid, orthogonal nucleotides, analogs thereof, or combinations thereof. Nucleic acids may also include analogs of DNA or RNA having modifications to either the bases or the backbone.

RNA Switch Domains

The RNA switch domain has a sensor domain and an actuator domain. RNA switch domains can be designed according to the methods developed by the inventors (Win, M. N. & Smolke, C. D. From the Cover: A modular and extensible RNA-based gene regulatory platform for engineering cellular function. Proc Natl Acad Sci USA 104, 14283-14288 (2007); Win, M. N. & Smolke, C. D. Higher-order cellular information processing with synthetic RNA devices. Science 322, 456-460 (2008); Isaacs, F. J., Dwyer, D. J. & Collins, J. J. RNA synthetic biology. Nat Biotechnol 24, 545-554 (2006); Wieland, M. & Hartig, J. S. Artificial riboswitches: synthetic mRNA-based regulators of gene expression. Chembiochem 9, 1873-1878 (2008); US Patent Applications: 20090143327 (General composition framework for ligand-controlled regulatory systems), 20090098561 (Higher-order cellular information processing devices), 20090082217 (Selection of nucleic acid-based sensor domains within nucleic acid switch platform), and 20060088864 (Aptamer regulated nucleic acids and uses thereof)), each of which is incorporated by reference in its entirety. Design of the RNA domains used in the invention can make use of the relative ease by which RNA can be modeled and designed (Mathews, D. H. & Turner, D. H. Prediction of RNA secondary structure by free energy minimization. Curr Opin Struct Biol 16, 270-278 (2006)), and can mimic natural RNA regulatory RNAs (Novina, C. D. & Sharp, P. A. The RNAi revolution. Nature 430, 161-164 (2004); Fedor, M. J. & Williamson, J. R. The catalytic diversity of RNAs. Nat Rev Mol Cell Biol 6, 399-412 (2005); Breaker, R. R. Complex riboswitches. Science 319, 1795-1797 (2008)).

In general, a RNA switch (or aptamer-regulated nucleic acid), typically comprises two primary domains: first, a sensor domain that can bind a ligand, and second, an actuator or functional domain. In one embodiment, the RNA switch used is a ribozyme ON switch, which are RNA devices that convert a small molecule input to an increased gene expression output, to develop a cell-intrinsic control system for cytokine production. In such an embodiment, the system design ensures suppression of cell growth as a default state and induction of cell proliferation only in the presence of an administered ligand (small-molecule drug) input. In this embodiment, the RNA switch is placed in the 3' untranslated region (UTR) of a target gene product, where self-cleavage by the ribozyme results in rapid degradation of the gene product transcript and decreased production of the gene product protein. The RNA switch is designed to adopt at least two conformations (input-unbound and input-bound) associated with either a ribozyme-active or a ribozyme-inactive state. The presence of the small molecule input stabilizes the input-bound, ribozyme-inactive conformation of the switch, thereby preserving transcript integrity and upregulating cytokine production, resulting in autocrine cell growth. The absence or removal of the input ligand stabilizes the ribozyme-active conformation, resulting in transcript degradation and reduced gene product production. When the gene product is a cytokine, transcript degradation in the absence of the ligand is enhanced and cell growth is diminished.

For example, FIG. 1b shows an engineered T-cell proliferation regulatory system based on the programmable drug-mediated regulation of cytokine expression from a synthetic ribozyme switch. In the absence of exogenous small molecule input, the ribozyme-active conformation of the switch is stabilized, resulting in rapid degradation of the target transcript and inhibition of cell growth. The presence of input molecules stabilizes the ribozyme-inactive conformation of the switch, thereby preserving transcript integrity and upregulating autocrine growth cytokine production, resulting in elevated cell growth.

Stringent control of the gene product expression may be desirable for a number of embodiments. In some embodiments, the gene product being controlled may be highly potent, such that the regulatory system requires stringent control over basal expression levels. For example, in one embodiment, when the gene product is a cytokine that stimulates T-cell proliferation, the RNA switch can be designed such that in the absence of input ligand the engineered T cells exhibit proliferation levels similar to cells growing in the absence of cytokine. In one such embodiment, stringency of expression of the gene product in response to the ligand is provided by incorporating multiple RNA switches within the nucleic acid. Such RNA switches can have sensor domains that detect the same ligand, or can detect different ligands. In one embodiment, two or more copies of the same RNA switch are used. In yet another embodiment, three or more copies of the same RNA switch are used. When multiple RNA switches are used, they can be separated by spacer nucleic acids.

Sensor Domains

The sensor domain can be an aptamer nucleic acid sequence that binds to a specific molecular ligand including small molecules, proteins and nucleic acids. The switch molecule can adopt two different conformations or states that are typically in equilibrium or approaching equilibrium through, for example, an allosteric or conformational change. One of the switch states has the correctly formed aptamer that can bind the ligand, together with a (first) conformation of the sensor domain. This state may be called the "ligand-binding state/conformation." Once a ligand binds to the ligand-binding state/conformation of the switch, the switch and the aptamer is "ligand-bound." The other switch state does not have the correctly formed aptamer and thus cannot bind the ligand. Consequently, this state may be called the "ligand-free state/conformation." The ligand-free state may be associated with a different (second) conformation of the sensor domain. When the ligand is present, it binds to one of those states (the ligand-binding state) and therefore shifts the equilibrium to favor that conformation of the switch and the sensor domain. The sensor domain can be part of the same nucleic acid sequence as the actuator domain, including having overlapping nucleic acid sequences. The two conformations of the sensor domain can modulate the activity of the actuator or functional domain.

At the macro-level, it appears that the ligand binding to the switch (with two conformations or states) "induces" a conformational change in the switch to favor the ligand-binding state (and its associated functional domain conformation), although mechanistically, the ligand may not bind the ligand-free switch state (and its associated functional domain conformation). Therefore, "induce a conformational change (of the switch)" or similar terms as used herein refers to this macro-level equilibrium shift between the switch states, and does not necessarily imply that the ligand actually binds to the ligand-free switch state and induces a conformation change of this state to become the ligand-binding switch state.

Suitable aptamer or sensor sequences can be designed or selected by any technique known to one of skill in the art. Methods are available that involve iterative cycles of selection and amplification, known as in vitro selection, or SELEX (Systematic Evolution of Ligands by Exponential enrichment) (see Ellington et al., Nature 346: 818-822, 1990; Tuerk et al., Science 249: 505-510, 1990; and Wilson & Szostak. In vitro selection of functional nucleic acids. *Annu Rev Biochem* 68, 611-647 (1999)). Initially, a starting pool of nucleic acids is generated and screened in a rapid and parallel manner, using for example, high-throughput methods and laboratory automation (Cox et al., Nucleic Acids Res 30: e108, 2002). Aptamers also can be selected by the methods disclosed in U.S. patent application 20090082217.

Sensors can also be designed to detect other molecular inputs, such as cellular transcripts through Watson-Crick base-pairing rules.

Actuator Domains

The actuator component can be a RNA regulatory sequence that acts through any of a variety of gene regulatory mechanisms, including ribozyme-based cleavage and transcript inactivation and RNA interference-based gene silencing. Standard strategies to those familiar with the art can be used to design the actuator components. Such strategies include those disclosed in the U.S. patent applications by Smolke disclosed above.

In one embodiment, the actuator domain is a hammerhead ribozyme that cleaves the 3' untranslated region of the gene product mRNA. The ribozyme can be coupled to a sensor domain that binds a ligand so that the ribozyme cleaves the mRNA either in the presence or absence of the ligand. Binding of the ligand can either induce ribozyme cleavage or inhibit ribozyme cleavage depending on the design of the RNA switch.

The nucleic acid system can have multiple RNA switch domains. When multiple RNA switch domains are used, the RNA switch domains can be repeat copies of identical RNA switch domains, or can be unique RNA switch domains. For example, a nucleic acid can include multiple copies of a RNA switch domain to increase the stringency of the response to the ligand. In one embodiment, the nucleic acid includes two or more copies of a RNA switch domain responsive to the same ligand. In another embodiment, the nucleic acid includes three or more copies of a RNA switch domain responsive to the same ligand. In another embodiment, two or more RNA switch domains can be used that are responsive to different ligands.

Ligands

A ligand may be an endogenous (produced by the organism or cell) or an exogenous molecule. Endogenous molecules include, for example, polypeptides, peptides, nucleic acids, carbohydrates, fatty acids, lipids, non-peptide hormones, and metabolic precursors or products thereof. When the ligand is an exogenous molecule, it can be a small organic molecule, a polypeptide, peptide, nucleic acid, carbohydrate, fatty acid, lipid, non-peptide hormone, or metabolic precursor or product thereof. In one embodiment, the ligand has a molecular weight of less than about 2.5 kD. In yet another embodiment, the ligand has a molecular weight of less than about 1 kD, less than about 0.8 kD, less than about 0.6 kD, less than about 0.4 kD, or even less than about 0.2 kD. In one embodiment, the small molecule is a cell permeable agent that is contacted with the cell, e.g., either by ectopic addition or by diffusion from a neighboring cell. If the exogenous ligand itself is not cell permeable, it can be formulated using drug delivery formulations or modifications (e.g., esterification) to achieve cell permeability. In some such cases, a precursor ligand can be delivered to the cell or organism that is modified in the cell to release an active ligand (e.g., by ester cleavage). In one embodiment, the exogenous ligand does not have a substantial effect on the target cell other than regulation of the gene product. In one embodiment, the ligand will have minimal off-target toxicities, meaning that it specifically binds the sensor domain or aptamer over other cellular targets.

Gene Products

The gene products encoded by the nucleic acid are selected to affect cell fate decisions of mammalian cells. Cell fate decisions include activation, proliferation, apoptosis or differentiation of the mammalian cell. The gene product can be a coding sequence for a protein, or can encode a non-coding RNA, such as an siRNA or miRNA.

In one embodiment, the gene product encodes a cytokine. The cytokine is selected to affect the cell fate of the mammalian cell. Suitable cytokines include, for example, IL-2, IL-4, IL-7, IL-9 or IL-15. Cytokines such as IL-2, IL-4, IL-7, IL-9 and IL-15 are potent growth-stimulatory molecules whose effects on cell growth are amplified through the JAK-STAT signaling pathway (FIG. 1a). Such cytokines are advantageous because expression of such a molecule will result in signal amplification through the cascade toward downstream functional responses.

Clonal expansion of T cells is an important component of T-cell activation mediated by cytokines such as interleukin-2 (IL-2) and interleukin-15 (IL-15), which activate JAK-STAT signaling pathways and lead to the expression of genes involved in growth modulation (Johnston, J. A. et al. Tyrosine phosphorylation and activation of STAT5, STAT3, and Janus kinases by interleukins 2 and 15. Proc Natl Acad Sci USA 92, 8705-8709 (1995)) (FIG. 1a). Sustaining the survival and proliferation of T cells following adoptive transfer is challenging due to the limited availability of homeostatic cytokines (IL-15/IL-7) and stimulatory antigen presenting cells. The persistence of adoptively transferred melanoma-specific tumor infiltrating lymphocytes has been shown to improve significantly with prior lymphodepletion and subsequent administration of high-dose IL-2 (Gattinoni, L., Powell, D. J., Jr., Rosenberg, S. A. & Restifo, N. P. Adoptive immunotherapy for cancer: building on success. Nat Rev Immunol 6, 383-393 (2006)). However, such treatments require that the patients be subjected to myeloablative total body irradiation/chemotherapy and toxic levels of IL-2. Alternative strategies based on the unregulated expression of growth-related genes have been developed to prolong T-cell survival, including expression of the antiapoptotic genes bcl-2 and bcl-$x_L$, overexpression of the human telomerase reverse transcriptase (hTERT) gene, and expression of genes encoding the growth factors IL-2 and IL-15 (Leen (2007)). While capable of sustaining T-cell survival, these strategies also pose the risk of uncontrolled lymphoproliferation and leukemic transformation. The ability to integrate growth stimulatory gene expression with tightly controlled genetic regulatory systems has the potential to greatly improve the safety and efficacy of adoptive T-cell therapy.

IL-15, provides potent homeostatic T-cell survival/proliferative signals, inhibits IL-2-mediated AICD, and may be superior to IL-2 in immunotherapy applications (Hsu, C. et al. Primary human T lymphocytes engineered with a codon-optimized IL-15 gene resist cytokine withdrawal-induced apoptosis and persist long-term in the absence of exogenous cytokine. J Immunol 175, 7226-7234 (2005); Waldmann, T. A., Dubois, S. & Tagaya, Y. Contrasting roles of IL-2 and IL-15 in the life and death of lymphocytes: implications for immunotherapy. Immunity 14, 105-110 (2001)). Recently, IL-15 has been shown to function in establishing the long-term persistence of adoptively transferred central memory T ($T_{CM}$) cells in primates, suggesting significant potential in T-cell therapy for cancer (Berger, C. et al. Adoptive transfer of effector CD8+ T cells derived from central memory cells establishes persistent T cell memory in primates. J Clin Invest 118, 294-305 (2008)).

Other gene products can be used that induce other cell fates. For example, the

Immunotherapy

The system of the invention also can include a nucleic acid encoding a receptor targeting an antigen. For example, T cells can be engineered to express T-cell receptors. The receptors can target an antigen, including, for example, a viral or a tumor antigen. Such receptors may be patient-derived, natural or synthetic (whether selected or designed) (Blattman, J. N. & Greenberg, P. D. Cancer immunotherapy: a treatment for the masses. Science 305, 200-205 (2004) and June, C. H. Principles of adoptive T cell cancer therapy. *J Clin Invest* 117, 1204-1212 (2007); June, C. H. Principles of adoptive T cell cancer therapy. J Clin Invest 117, 1204-1212 (2007); Falkenburg, J. H., Smit, W. M. & Willemze, R. Cytotoxic T-lymphocyte (CTL) responses against acute or chronic myeloid leukemia. Immunol Rev 157, 223-230 (1997); Walter, E. A. et al. Reconstitution of cellular immunity against cytomegalovirus in recipients of allogeneic bone marrow by transfer of T-cell clones from the donor. N Engl J Med 333, 1038-1044 (1995); Morgan, R. A. et al. Cancer regression in patients after transfer of genetically engineered lymphocytes. Science 314, 126-129 (2006); Gonzalez, S. et al. Genetic engineering of cytolytic T lymphocytes for adoptive T-cell therapy of neuroblastoma. J Gene Med 6, 704-711 (2004); Kahlon, K. S. et al. Specific recognition and killing of glioblastoma multiforme by interleukin 13-zetakine redirected cytolytic T cells. Cancer Res 64, 9160-9166 (2004)). The efficacy of adoptive immunotherapy in humans is often limited by the failure of transferred T-cells to persist in the host. Dudley, M. E. et al. Adoptive transfer of cloned melanoma-reactive T lymphocytes for the treatment of patients with metastatic melanoma. J Immunother 24, 363-373 (2001); Yee, C. et al. Adoptive T cell therapy using antigen-specific CD8+ T cell clones for the treatment of patients with metastatic melanoma: in vivo persistence, migration, and antitumor effect of transferred T cells. Proc Natl Acad Sci USA 99, 16168-16173 (2002); Mackensen, A. et al. Phase I study of adoptive T-cell therapy using antigen-specific CD8+ T cells for the treatment of patients with metastatic melanoma. J Clin Oncol 24, 5060-5069 (2006)). Such shortcomings can be addressed by inducing proliferation of the T-cells using the instant invention.

Marker Proteins

In certain embodiments, it is useful to include a marker protein to allow monitoring of the expression of the nucleic acid system. The system can include a nucleic acid encoding a marker protein that can be used to monitor transfection of the system into a mammalian cell or expression of the gene product. The marker protein can be any protein detectable by methods known to one of skill in the art. In one embodiment, the protein is luciferase. In another embodiment, the protein is a fluorescent protein. The nucleic acid encoding such a fluorescent protein also can be linked to the RNA switch so that regulation by the ligand can be directly monitored by measuring fluorescence of the protein. Suitable proteins include those described in Ben N. G. Giepmans et al., The fluorescent toolbox for assessing protein location and function. *Science* 312: 217-224 (2006).

Safety Proteins

The system also may include a gene encoding a safety protein that encodes an enzyme that can kill the host cell in the presence of a drug or prodrug. For example, the thymidylate synthase gene or a mutant thereof can be included in the system. For example, Cells expressing thymidylate synthase are sensitive to certain prodrugs including ganciclovir. Expression of thymidylate synthase within the cell renders the cell sensitive to the prodrug ganciclovir. In another embodiment, the CD20 gene is included. Cells that are CD20+ can be killed through treatment with an anti-CD20 antibody (e.g., Rituxumab from Roche). Introna, M. et al., Genetic modification of human T cells with CD19: A strategy to purify and lyse transduced cells with anti-CD20 antibodies, Human Gene Therapy 11:611-620. In another embodiment, a separate RNA switch controlling expression of a second gene product and responding to a different ligand than is used for control of the main gene product can be included. In such an embodiment, the second RNA switch can be triggered by a separate small molecule ligand. The second gene product can include a protein for killing the cell. For example, the second gene product can encode an apoptosis inducing protein or a toxin that would kill the cell in response to a ligand. In one such embodiment, the gene product would encode the apoptosis-inducing protein, PUMA.

Mammalian Cells

The nucleic acids of the invention can be designed to be used in any mammalian cell. Suitable cells include cultured mammalian cells in vitro and mammalian cells in vivo. Cultured cells include hybridomas. Particularly suitable mammalian cells are human mammalian cells. In a preferred embodiment, the mammalian cells are transfected with a nucleic acid of the invention in vitro. In another preferred embodiment, human cells are treated with a nucleic acid of the invention in vivo. The nucleic acids of the invention also can be delivered to a mammalian cell through a viral vector or delivery system.

Methods of Making Cells

The system of the invention can be introduced into a cell by a variety of methods known to one of skill in the art, either in vivo or in vitro. The nucleic acid can be transfected into a cultured human cell in vitro, using any suitable technique for the type of cell, including mechanical methods, chemical methods, lipophilic methods, and electroporation. Microinjection and use of a gene gun with, for example, a gold particle substrate for the DNA to be introduced is a representative, non-limiting exemplary mechanical method. Use of calcium phosphate or DEAE-Dextran is a representative, non-limiting exemplary chemical method. Non-limiting exemplary lipophilic methods include use of liposomes and other cationic agents for lipid-mediated transfection. For example, for certain cells, lipophilic reagents can be used to introduce a nucleic acid into the cell. Such reagents include LIPOFECTAMINE (Invitrogen) and FUGENE HD (Roche). Cells also can be transfected by electroporation, for example using AMAXA NUCLEOFECTOR (Lonza). Cells transfected with a nucleic acid can be reintroduced into an organism. For example, a lymphocyte including a RNA switch and a cytokine can be introduced into a patient by injection into the blood stream.

The nucleic acids also can be delivered directly to a mammal, or incorporated into a viral vector for introduction into cells within an organism. Suitable viral vectors include, for example, retroviruses, adenoviruses, adeno-associated viruses, as well as hybrid vectors, that all targeting of mammalian cells within an organism. In such embodiments, the nucleic acid can be introduced as a packaged viral particle capable of infecting a mammalian cell.

Making RNA Switches

A nucleic acid of the invention may be synthesized by standard methods known in the art, e.g., by use of an automated DNA synthesizer (such as are commercially available from Biosearch, Applied Biosystems, etc.). For example, methods of making aptamers are described in U.S. Pat. No. 5,582,981, PCT Publication No. WO 00/20040, U.S. Pat. No. 5,270,163, Lorsch and Szostak, Biochemistry 33: 973, 1994; Mannironi et al., Biochemistry 36: 9726, 1997; Blind, Proc. Nat'l. Acad. Sci. USA 96: 3606-3610, 1999; Huizenga and Szostak, Biochemistry 34: 656-665, 1995; PCT Publication Nos. WO 99/54506, WO 99/27133, WO 97/42317, and U.S. Pat. No. 5,756,291; (all incorporated by reference).

Another approach for generating nucleic acids utilizes standard recombinant DNA techniques using a construct in which the nucleic acid is placed under the control of a strong pol III or pol II promoter in an expression vector. This construct can be transformed or transfected into a prokaryotic or eukaryotic cell that transcribes the nucleic acid. Such a vector can remain episomal or become chromosomally integrated, as long as it can be transcribed to produce the desired nucleic acid. Expression vectors appropriate for producing a nucleic acid are well-known in the art. For example, the expression vector can be an episomal expression vector, an integrative expression vector, or a viral expression vector. A promoter may be operably linked to the sequence encoding the RNA switch and gene product. Expression of the sequence encoding the nucleic acid can be by any promoter known in the art to act in eukaryotic or prokaryotic cells. Such promoters can be inducible or constitutive. Examples of mammalian promoters include, but are not limited to the SV40 early promoter region (Bernoist and Chambon, Nature 290: 304-310, 1981), the promoter contained in the 3' long terminal repeat of Rous sarcoma virus (Yamamoto et al., Cell 22: 787-797, 1980), the herpes thymidine kinase promoter (Wagner et al., Proc. Natl. Acad. Sci. USA 78: 1441-1445, 1981), the regulatory sequences of the metallothionine gene (Brinster et al, Nature 296: 3942, 1982), etc.

EXAMPLES

Example 1

Controlled Expression of IL-2 in a Mammalian Cell

This example shows that a RNA switch can control the expression of a gene product using a small molecule applied to a mammalian cell. A fusion transgene encoding both a proliferative cytokine (IL-2) and a quantifiable protein marker (EGFP) was tested as a regulatory target to permit accurate quantification of the regulatory system's performance (FIG. 2a). The target transgene (egfp-t2a-il2) encodes a fusion of a reporter protein (GFP) and a growth cytokine (IL-2). Spacer sequences are placed between switches to provide structural insulation and maintain the integrity and functional independence of each switch. The cytokine and reporter protein were linked through a self-cleaving T2A peptide chain (SEQ ID NO: 24) to ensure that the ribozyme switch regulatory activity was equally effective on the linked target genes but that the proteins fold and function as independent molecules. Three theophylline-responsive ribozyme switches (L2bulge 1, 8, and 9; see Example 9), which had been tuned through sequence modifications to exhibit different regulatory response properties (Win (2007)), were inserted into the 3' UTR of the egfp-t2a-il2 fusion gene. Plasmids incorporating this regulatory system under the transcriptional control of an EF-1α promoter were transiently transfected into the CTLL-2 mouse T cell line which, like primary human T cells, is dependent on common γ-chain signaling for survival and proliferation (Gillis, S. & Smith, K. A. Long term culture of tumour-specific cytotoxic T cells. Nature 268, 154-156 (1977)). Each of the ribozyme switches resulted in input-responsive regulation over cell viability and fluorescence (FIG. 2b, FIG. 5a, see Example 9) confirming the prescribed function of these devices in mammalian cells. The ribozyme-based regulatory systems provided a titratable response over a range of input concentrations (FIG. 2c, FIG. 5b), indicating the ability to adjust gene expression levels based on input availability.

Example 2

Expression Using Multiple RNA Switches

This example demonstrates a higher stringency nucleic acid having multiple RNA switches. To engineer a more stringent regulatory system, we implemented a tuning strategy based on linking multiple copies of the ribozyme switches in the 3' UTR of the transgene. The ribozyme switches are expected to act independently in this design, where only one of the switches needs to be in a ribozyme-active state to cleave and inactivate the transcript. Multiple-copy switch devices increase the probability of ribozyme-mediated transcript cleavage, thereby lowering basal expression levels. We developed a construction strategy for sequentially inserting ribozyme switches in the 3' UTR of the transgene construct and insulated the switches through standardized spacer sequences designed to maintain the structural integrity and functional independence of each switch (FIG. 2a).

Characterization of the multiple-copy switch systems indicated that this tuning strategy effectively decreased basal expression levels (FIG. 2b, FIG. 5a) and that the titratable response of the system was maintained (FIG. 2c, FIG. 5b). Stringent knockdown was achieved with three and four copies of the tightest switch (L2bulge9; FIG. 2b), which resulted in viability levels comparable to cells transfected with no cytokine or with the fully active, non-switch ribozyme (No IL-2 Control and sTRSV Ribozyme, respectively). The multiple-copy switch systems lowered the basal expression level while maintaining or even increasing the absolute difference in expression levels in response to ligand input, in effect expanding the dynamic range of the system when calculated as a fold change. Given the potency of the cytokine output in modulating growth, we anticipated the titratable range of the most stringent switches to be sufficient for effective T-cell growth regulation.

Example 3

Expression of IL-15 Using RNA Switches

This example demonstrates expression of a different gene product (IL-15) using the system described in Example 2. To develop a more clinically relevant regulatory system, we utilized the modularity of the ribozyme switch platform and replaced the egfp-t2a-il2 transgene with a trifunctional fusion transgene (cd19-tk-t2a-il15) encoding IL-15, mutant HSV-1 thymidine kinase (ser39TK, a protein marker that acts as a PET reporter and a suicide protein in the presence of the drug ganciclovir), and CD 19 (a quantifiable protein marker amenable to fluorescence- and immunomagnetic-based selections). The alternative transgene was placed directly into the theophylline-responsive switch systems based on L2bulge9 (FIG. 2d). Ribozyme switch systems with the altered target transgene exhibited ON switch control over cell viability and proliferation in transient transfection experiments (FIG. 2e), confirming modular coupling between the target transgene and the regulatory device. Furthermore, samples expressing IL-15 showed higher viability levels compared to those expressing IL-2 with the corresponding number of ribozyme switches (FIGS. 2c, 2e), suggesting IL-15 may be a more potent survival/proliferative cytokine and can better amplify the signal response. Therefore, under a low basal expression level, a small increase in IL-15 expression has the potential to significantly elevate the T-cell proliferation level.

Example 4

Expression in Stable T Cell Lines

Figure 6:
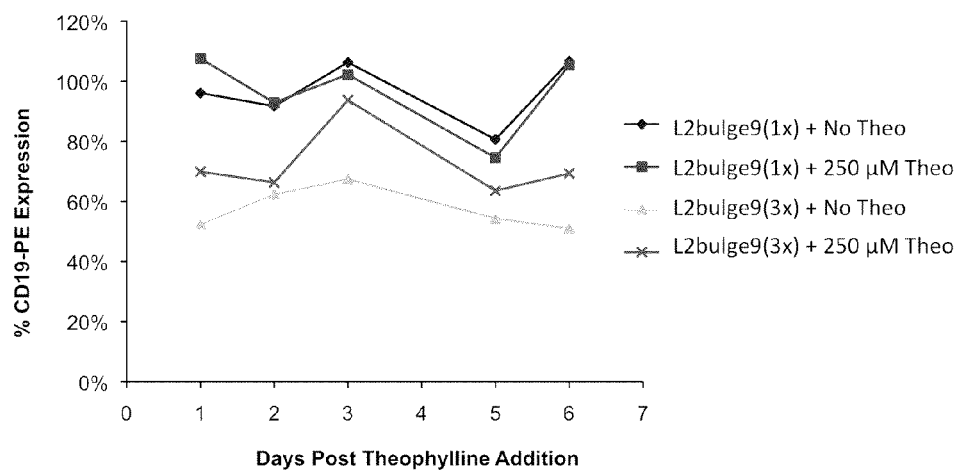
FIG. 6 shows the expression of the gene product CD19 in stable cell lines expressing one or multiple ribozyme switches.

This example demonstrates the stable expression of RNA switches in T cell lines. To characterize long-term behavior of the regulatory system in vitro and in vivo, we generated stable T cell lines expressing the theophylline-dependent ribozyme switch systems. To enable biophotonic imaging of cell populations in vivo, we generated a CTLL-2 cell line (CffLuc) that stably expressed the firefly luciferase (ffluc) gene via lentiviral transduction. We subsequently integrated T-cell proliferation regulatory systems based on one or three copies of L2bulge9 into CffLuc via transfection with linearized plasmids. Stable integrants were initially sorted based on CD 19 expression, and the sorted population was evaluated for switch activity. At the bulk population level, cells stably expressing three copies of the ribozyme switch had a lower basal level and larger switch dynamic range in response to theophylline addition compared to cells stably expressing one copy of the ribozyme switch, which is consistent with transient transfection results (FIG. 6). As seen in FIG. 6, stable integrants were selected by fluorescence-based cell sorting for CD 19+ populations. Bulk-sorted cells were cultured either with or without 250 µM theophylline for six days and CD19 expression levels were monitored by staining with PE-conjugated CD19 antibodies. Although bulk cell lines stably expressing the single-copy ribozyme switch system did not exhibit significant increases in gene expression in response to 250 µM theophylline, individual clones that exhibited low basal expression levels and significant theophylline-responsive increases in expression were successfully isolated from this bulk population (see FIG. 7).

Figure 3:
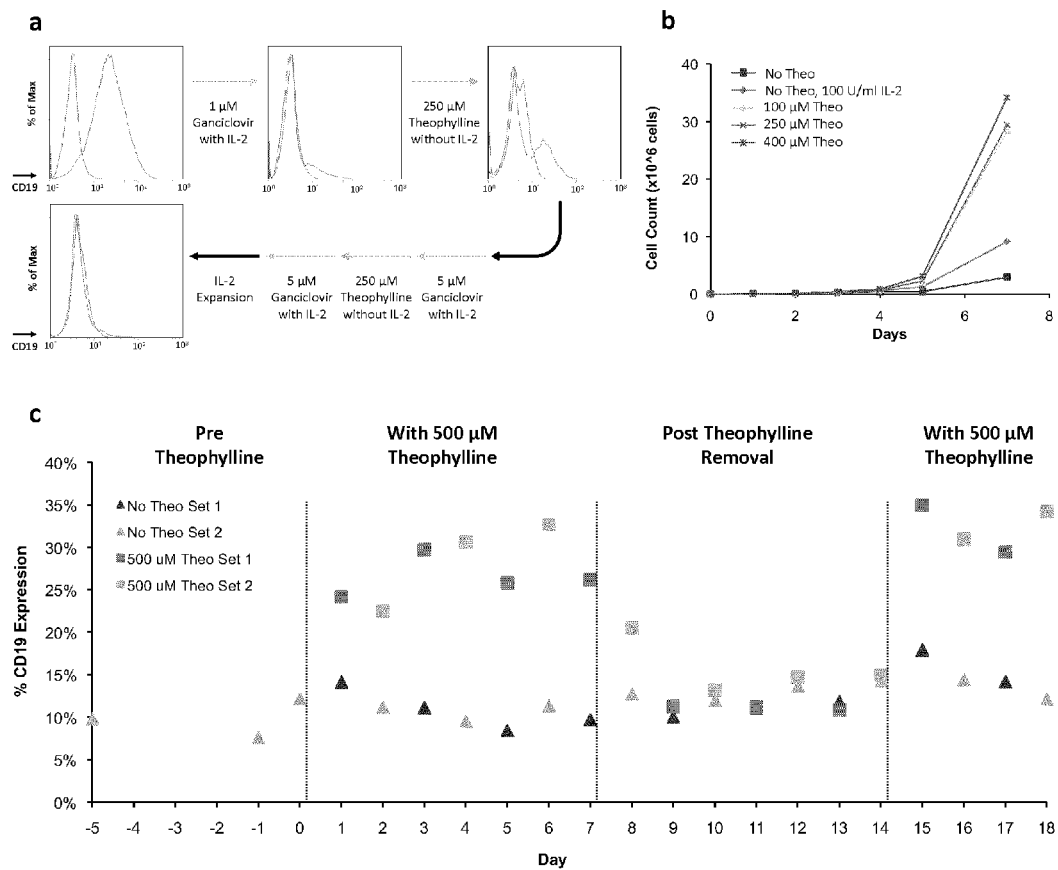
FIG. 3a shows a fluorescence measurement of gene expression levels in T cells selected to stably express a ribozyme switch system monitored by staining with PE-conjugated CD19 antibody of a bulk stable cd19-tk-t2a-il15-L2bulge9 (3×) cell line versus a CffLuc cell line.
FIG. 3b shows a graph of cell growth monitored by counting viable cells, and data for a representative clone (1264-48, expressing cd19-tk-t2a-il15-L2bulge9(3×)) grown under varying theophylline concentrations are shown.
FIG. 3c shows gene expression levels in duplicate cultures of the clonal cell line 1264-48 in the presence or absence of theophylline. A second set of duplicate cultures of the same clone was continuously cultured in the absence of theophylline for the duration of the 18-day trial (light and dark blue). Gene expression levels were monitored by staining with PE-conjugated CD19 antibody, and fluorescence values were normalized to those from the inactive ribozyme control.

We further refined the sorted population by alternating treatment with ganciclovir and IL-2 or with theophylline and no IL-2 (FIG. 3a) to enrich for clones with low basal expression levels and sufficiently high ON-state expression levels to sustain cell survival, respectively. FIG. 3a shows the generation of T cell lines stably expressing the ribozyme switch systems through growth-based selections. CTLL-2 cells stably expressing a luciferase reporter (CffLuc) were transfected with linearized plasmids encoding ribozyme switch systems based on L2bulge9. Stable integrants were sorted for CD19 expression and subsequently subjected to alternate negative and positive growth selections with ganciclovir and theophylline, respectively. We generated clonal cell lines by a final fluorescence-based sorting step for CD19 positive cells in the presence of theophylline.

Growth behavior of individual clones was characterized by culturing under various theophylline concentrations. Results indicate that the T-cell proliferation regulatory system retained functionality over long time periods when stably integrated, and that theophylline effectively replaced IL-2 as the trigger for cell proliferation in culture (FIG. 3b). T cells stably expressing ribozyme switch systems exhibit drug-mediated regulation of growth over extended time periods in vitro. Fifteen of the sixteen clones examined showed substantial theophylline-responsive increase in cell growth (FIG. 7), supporting that the growth modulation effect is specific to the introduced regulatory system. In the experiment shown in FIG. 7, the cell lines were cultured at various theophylline concentrations, and cell growth was monitored by counting viable cells. Clones indicated as 1261-xx stably expressed cd19-tk-il15-L2bulge9(1x). Clone 1264-xx stably expressed cd19-tk-il15-L2bulge9(3x). Growth behaviors differ from clone to clone, as would be expected from non-site-specific integration of the transgene into the host chromosomes. Theophylline-responsive increase in cell growth is evident in fifteen of the sixteen tested clones, and the growth elevation is statistically significant for the sample set (P=0.0150, 0.0011, 0.0013 for 100 µM, 250 µM, and 400 µM, respectively, by Whitney-Mann U test).

Example 5

Figure 8:
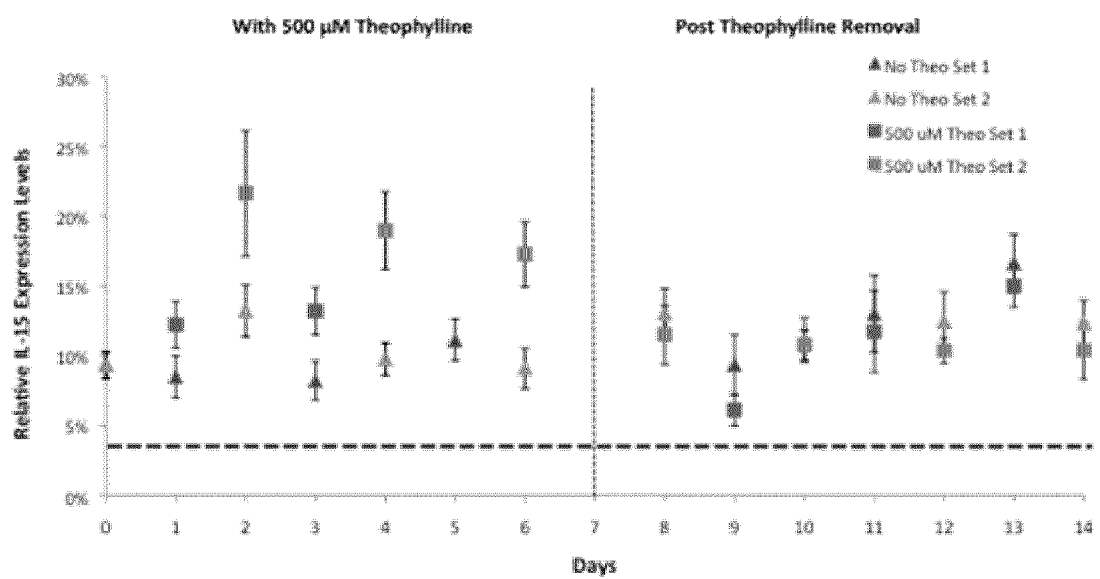
FIG. 8 shows relative IL-15 mRNA levels are elevated in the presence of theophylline and return to basal levels upon theophylline removal at day 7.
Figure 9:
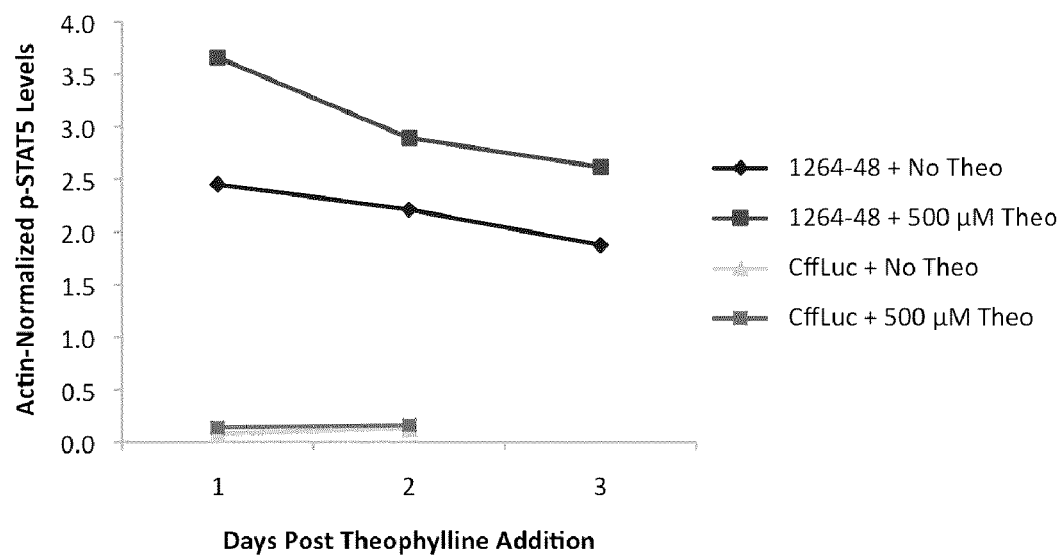
FIG. 9 shows a graph of pSTAT5 levels in cells with or without the theophylline-dependent ribozyme switch, in the presence and absence of theophylline.

Confirmation of Mechanism of Growth Regulation in T Cells Expressing Theophylline Regulated RNA Switches Additional assays on a clonal cell line harboring three copies of L2bulge9 (clone 1264-48) were performed to verify the mechanism of growth regulation and examine the dynamic behavior of the regulatory system to variations in theophylline availability. Cell cultures were grown for one week in the presence of 500 µM theophylline and continued for a second week in the absence of theophylline. Theophylline was reintroduced for another four days at the end of the study. Compared to the identical clone continuously cultured in the absence of theophylline, the cell population exhibited elevated CD19 protein levels within 24 hours of theophylline addition and levels remained elevated throughout the period of theophylline treatment (FIG. 3c). CD19 levels returned to basal levels within 48 hours of theophylline removal from the culture. The theophylline-responsive increase in CD19 expression was repeated upon reintroduction of theophylline to culture media. IL-15 expression patterns were verified at the transcript level through quantitative RT-PCR (Example 21, FIG. 8). In the experiment shown in FIG. 8, qRT-PCR was performed on mRNA extracted from a CTLL-2 cell line stably expressing cd19-tk-il15-L2bulge9(3×) (clone 1264-48). IL-15 expression levels were normalized to expression levels of the housekeeping gene hprt1, and relative IL-15 expression levels were obtained by normalizing to the inactive ribozyme control. Reported values are mean±s.d. from three replicate samples. Samples shown in this figure were collected from the same cultures as described in FIG. 3c. In addition, western blot analysis of phosphorylated STAT5 levels verified activation of the IL-15 receptor-signaling cascade in the presence of theophylline (FIG. 9). FIG. 9 illustrates that cells stably expressing the T-cell proliferation regulatory system exhibit increased signaling through the JAK-STAT pathway in the presence of theophylline. Western blot analysis was performed on protein extracts from the CffLuc and 1264-48 cell lines for phosphorylated STAT5 (p-STAT5), an intermediate in the IL-15 signaling cascade. The levels of p-STAT5 in each sample were normalized to that of 13-actin. The 1264-48 cell line, which stably expresses cd19-tk-il15-L2bulge9(3×), showed increased p-STAT levels in response to theophylline, indicating an increase in IL-15 signaling. The CffLuc cell line, which lacks the ribozyme switch system, served as a negative control and verified theophylline did not nonspecifically activate the JAK-STAT pathway. The CffLuc cell line could not survive beyond two days without exogenous IL-2, further demonstrating the autocrine growth cytokine production is necessary for sustaining CTLL-2 survival and proliferation in the absence of exogenous cytokine supplies. These results highlight the ability of the ribozyme switch regulatory system to quickly, effectively, and robustly switch gene expression on and off in response to the presence of input.

Example 6

Regulation of T-Cell Proliferation in Mice

Figure 4:
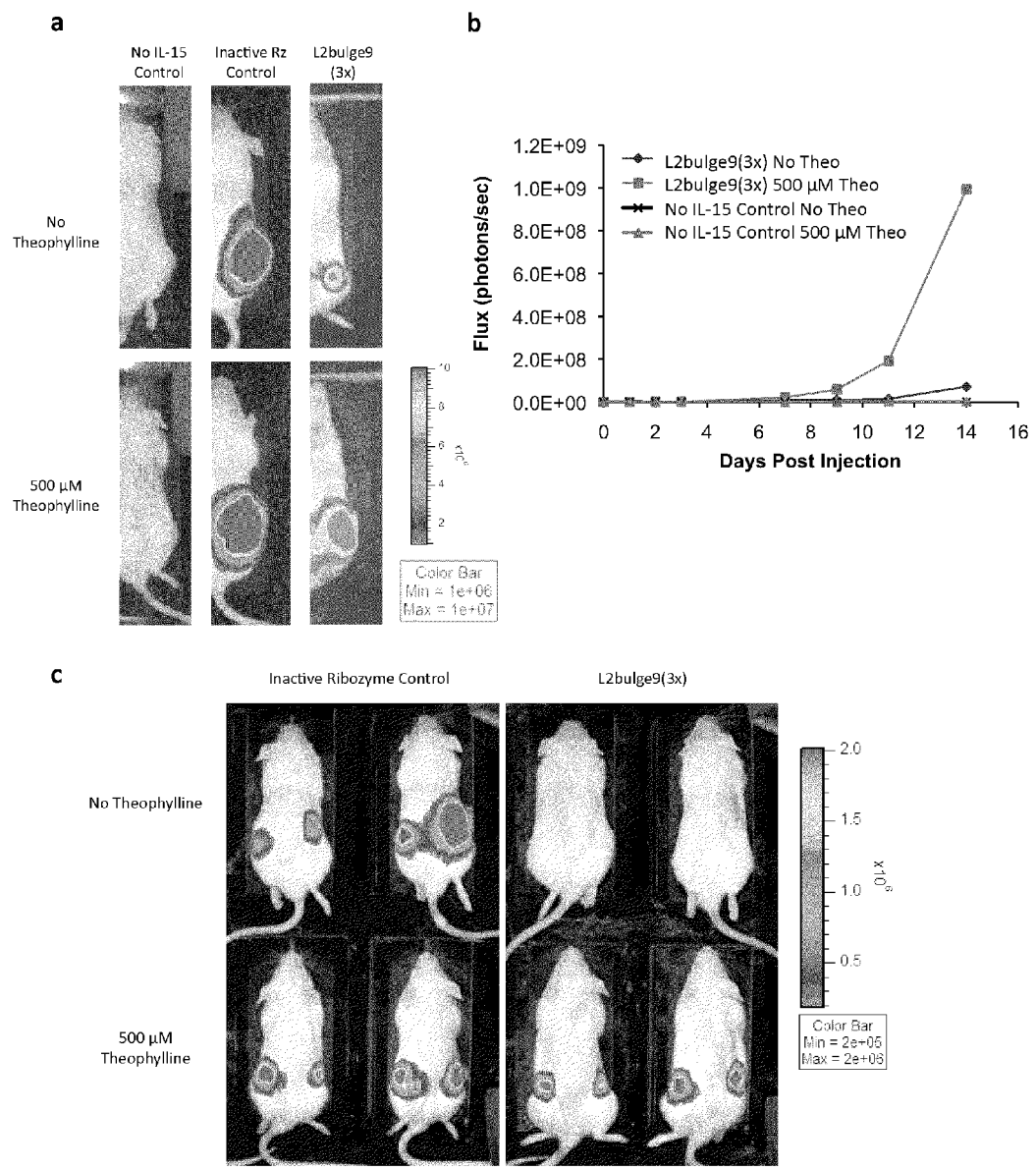
FIG. 4a shows images for mice at Day 14 post-injection of the negative control (No IL-15 Control, CffLuc), the positive control (Inactive Rz Control, stable cell line expressing inactive ribozyme), and a stable cell line expressing the ribozyme switch system (L2bulge9(3×), clone 1264-48) in the presence and absence of 500 µM theophylline.
FIG. 4b shows the total luciferase signal flux from the negative control (CffLuc) and clone 1264-48 (L2bulge9(3×)) over 14 days after injection of T cells.
FIG. 4c shows images at Day 4 post-injection of the positive control and clone 1264-48. Identical clones were injected into the two flanks of each mouse in the presence or absence of 500 µM theophylline.
Figure 10:
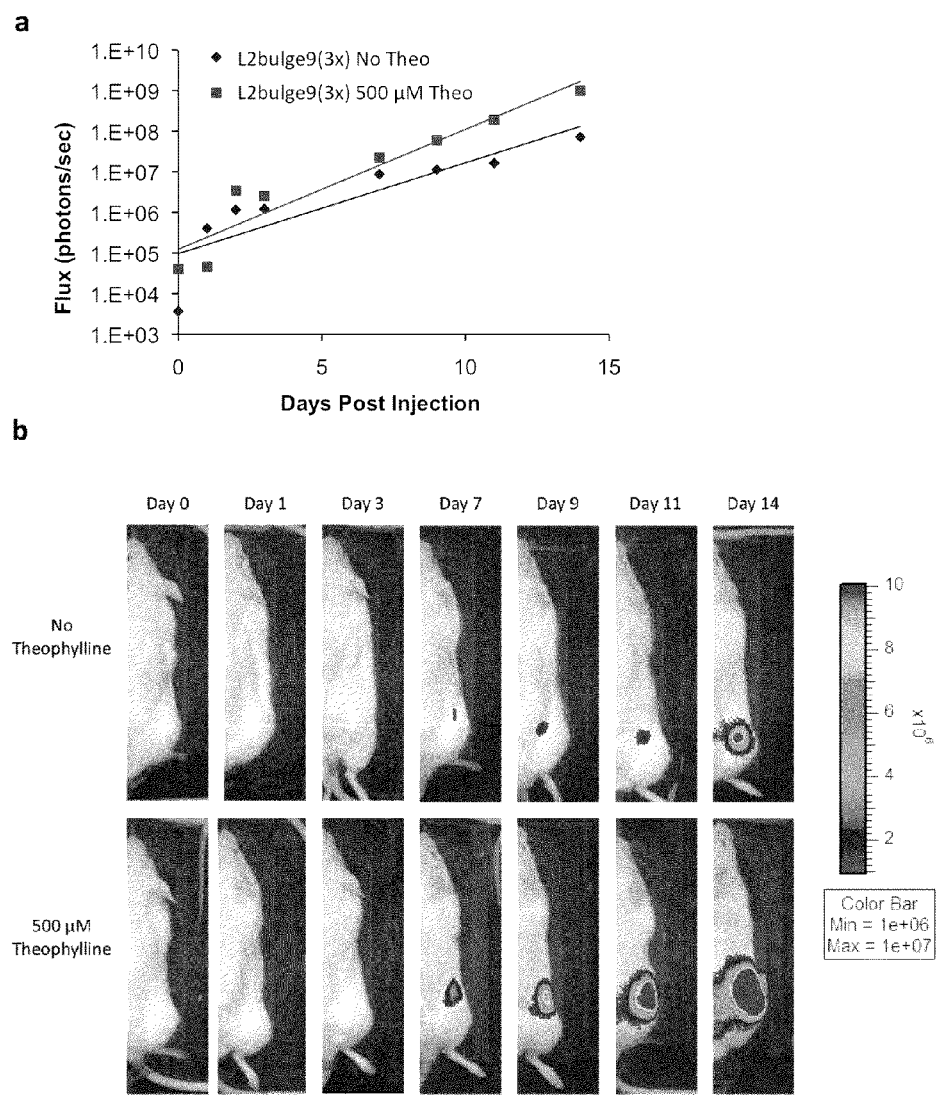
FIG. 10a shows total luciferase signal flux measurements collected over a 14-day period fitted to an exponential curve and used to calculate the in vivo growth rate of the injected cells.
FIG. 10b shows images of clone 1264-48 over time. The day of imaging post-injection of the stable cell line is indicated.
Figure 11:
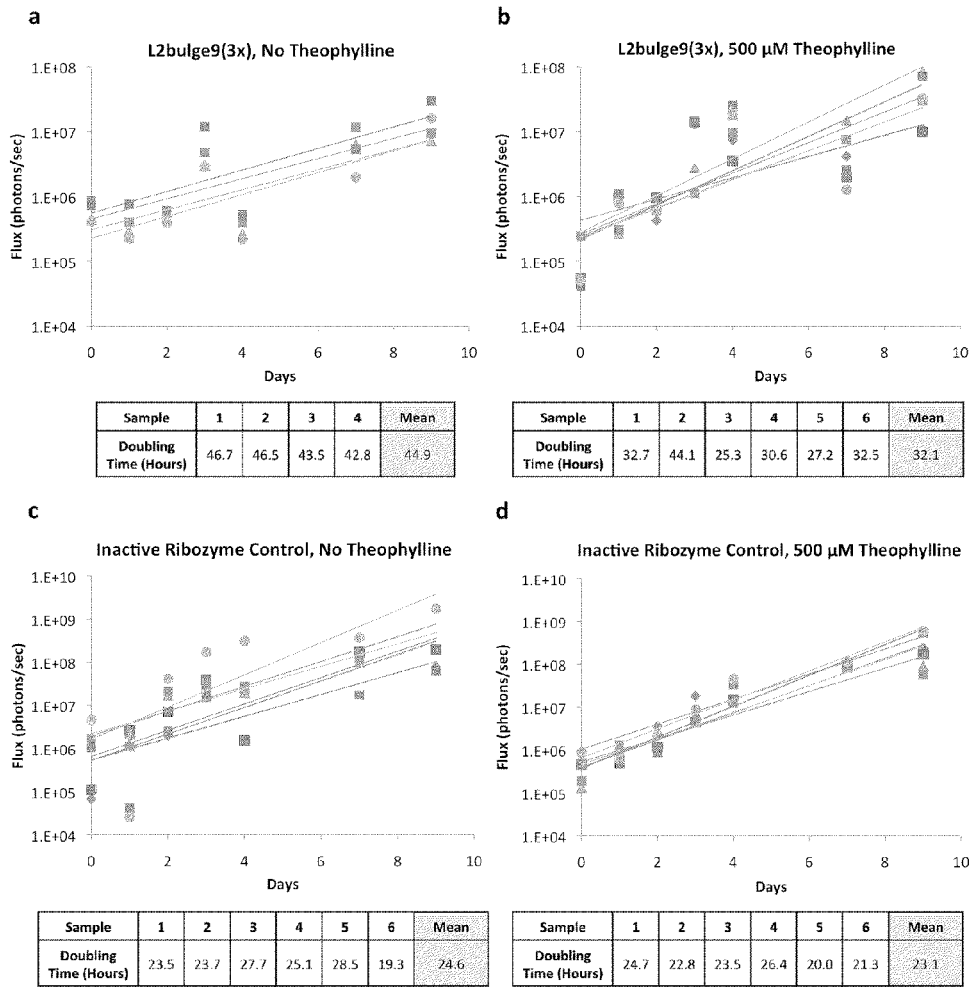
FIG. 11 shows total luciferase signal flux measurements collected over a 9-day period from replicate mice with various ribozyme switch clones. (a, b) Clone 1264-48 injected in the absence (a) or presence (b) of 500 µM theophylline. (c, d) Inactive ribozyme control cells injected in the absence (c) or presence (d) of 500 µM theophylline. Results indicate a 40% increase in the growth rate of clone 1264-48 in response to 500 µM theophylline and no statistically significant difference in the growth rate of the inactive ribozyme control in the presence and absence of theophylline.

This example demonstrates the regulation of T-cell proliferation of cells having a ribozyme regulatory system in mice. To verify in vivo functionality of the T-cell proliferation regulatory system, we examined several clonal cell lines for theophylline-dependent growth in mice over time. Select clones were encased in a hydrogel matrix that contained either 0 µM or 500 µM theophylline and injected into the flanks of NOD/SCID-$\gamma_c^{-/-}$ mice. Cell lines lacking the transgene regulatory system or stably expressing the inactive ribozyme construct served as negative and positive controls, respectively. In vivo T-cell expansion was not observed from clones lacking proliferative cytokine expression (No IL-15 control, FIG. 4a), demonstrating the need for cytokine expression in sustaining cell growth. Uncontrolled T-cell proliferation was observed in the absence of a functional ribozyme-based regulatory device regardless of theophylline availability (Inactive Rz control, FIG. 4a). In contrast, several clones expressing the functional ribozyme-based regulatory system exhibited theophylline-dependent growth behavior. The best clone, 1264-48, harbors three copies of L2bulge9 and showed a significantly stronger reporter signal at the conclusion of the 14-day study when injected with 500 µM theophylline compared to the same clone injected without theophylline (L2bulge9(3×), FIG. 4a). Growth rate calculations based on flux measurements over the 14-day period indicated a 32% increase in in vivo growth rate in the presence of 500 µM theophylline, leading to a 13.8-fold increase in luciferase signal by day 14 (FIG. 4b, FIG. 10). The in vivo study was repeated for clone 1264-48 with replicates, with the inactive ribozyme serving as the positive control. Flux measurements over a 9-day period indicate an average of 40% increase in the growth rate of clone 1264-48 in the presence of 500 theophylline ($n_1=4$, $n_2=6$, P=0.038 by Mann-Whitney U test). In contrast, the positive control did not show statistically significant changes in growth rate in response to theophylline addition ($n_1=6$, $n_2=6$, P=0.394; FIG. 4c, FIG. 11), indicating that the observed growth behavior was not due to nonspecific effects of theophylline.

Example 7

Generation of Human T Cells with IL-15 Regulated by a Theophylline RNA Switch

To demonstrate the portability of the regulatory system to human T lymphocytes and thus translatability to clinical applications, we generated primary human $T_{CM}$ cells transduced with lentiviral vectors encoding the cd19-tk-t2a-il15 transgene coupled to either three copies of the L2bulge9 ribozyme switch or an inactive ribozyme. Since short production timeline and streamlined processing may be important in clinical applications, characterization studies of $T_{CM}$ cells were performed on bulk transduced, unsorted populations to examine the robustness of the regulatory system in the scenario in which no population refinement was performed. Transduced cells were cultured in the presence and absence of 500 µM theophylline for five days, with daily monitoring of CD19 levels and cell viability by staining with CD19 antibody, annexin V, and SYTOX AAD dead cell stain. Compared to the inactive ribozyme control, cells expressing L2bulge9 showed up to 15% increase in CD19 expression levels (FIG. 12), up to 24% increase in the live cell population, and up to 54% reduction in the apoptotic cell population (FIG. 13) in the presence of theophylline, indicating ligand-responsive ON switch behavior in both gene expression and cell growth. As shown in FIG. 13, the ribozyme-based switch system effectively regulates the fate of primary human $T_{CM}$ cells. $T_{CM}$ cells stably expressing the cd19-t2a-il15-L2bulge9(3×) construct were cultured in the presence and absence of 500 µM theophylline. The population of cells that are (a) live and CD 19+ or (b) apoptotic and CD 19+ in the L2bulge9(3×) sample is normalized to that of the inactive ribozyme control cultured at the same theophylline concentration. Values reported represent mean±s.d. from triplicate samples. Results indicate an increase in live cells and decrease in apoptotic cells in response to theophylline addition, consistent with ligand-responsive upregulation of the growth cytokine IL-15.

Figure 12:
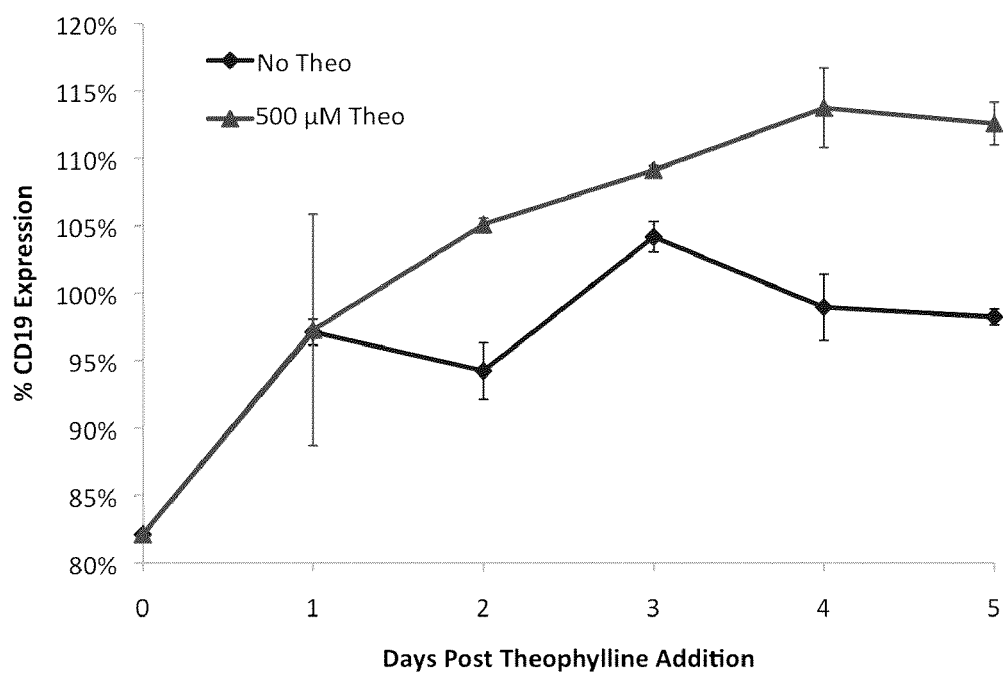
FIG. 12 shows the expression of the gene product CD19 in primary human $T_{CM}$ cells. $T_{CM}$ cells stably expressing the cd19-t2a-il15-L2bulge9(3×) construct cultured in the presence and absence of 500 µM theophylline.
Figure 13:
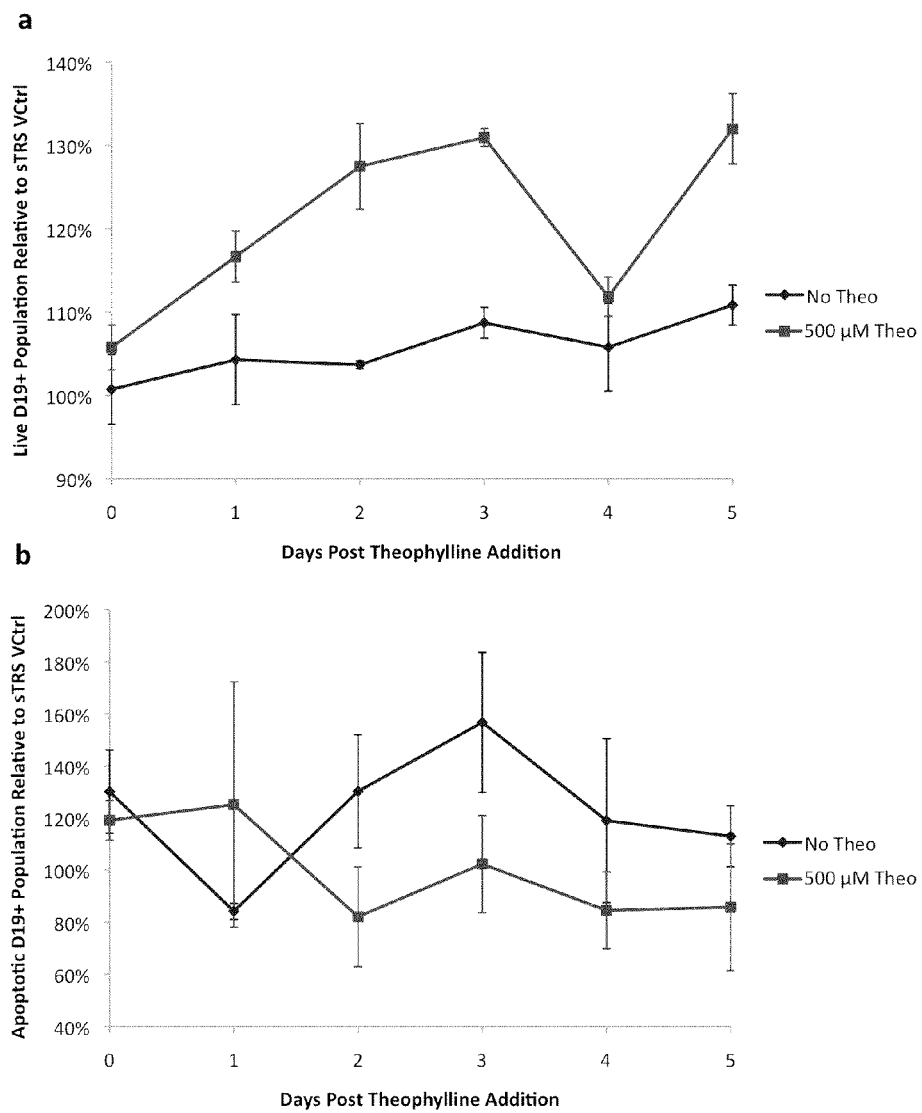
FIG. 13a shows the live CD 19+ population of primary human $T_{CM}$ cells stably expressing the cd19-t2a-il15-L2bulge9(3×) construct cultured in the presence and absence of 500 µM theophylline.
FIG. 13b shows the apoptotic CD19+ population of primary human $T_{CM}$ cells stably expressing the cd19-t2a-il15-L2bulge9(3×) construct cultured in the presence and absence of 500 µM theophylline.

FIG. 12 shows CD19 expression levels normalized to those of the inactive ribozyme control cultured at the same theophylline concentration and represent mean±s.d. from duplicate samples. The measured change in CD19 expression is comparable to that observed in CTLL-2 stable cell lines (FIG. 6), and the movement in population distribution between live and apoptotic cells supports the ribozyme-based regulatory system is effective in controlling the fate of primary human $T_{CM}$ cells.

Example 8

Demonstration of a Tetracycline-Responsive RNA Switch

Figure 2:
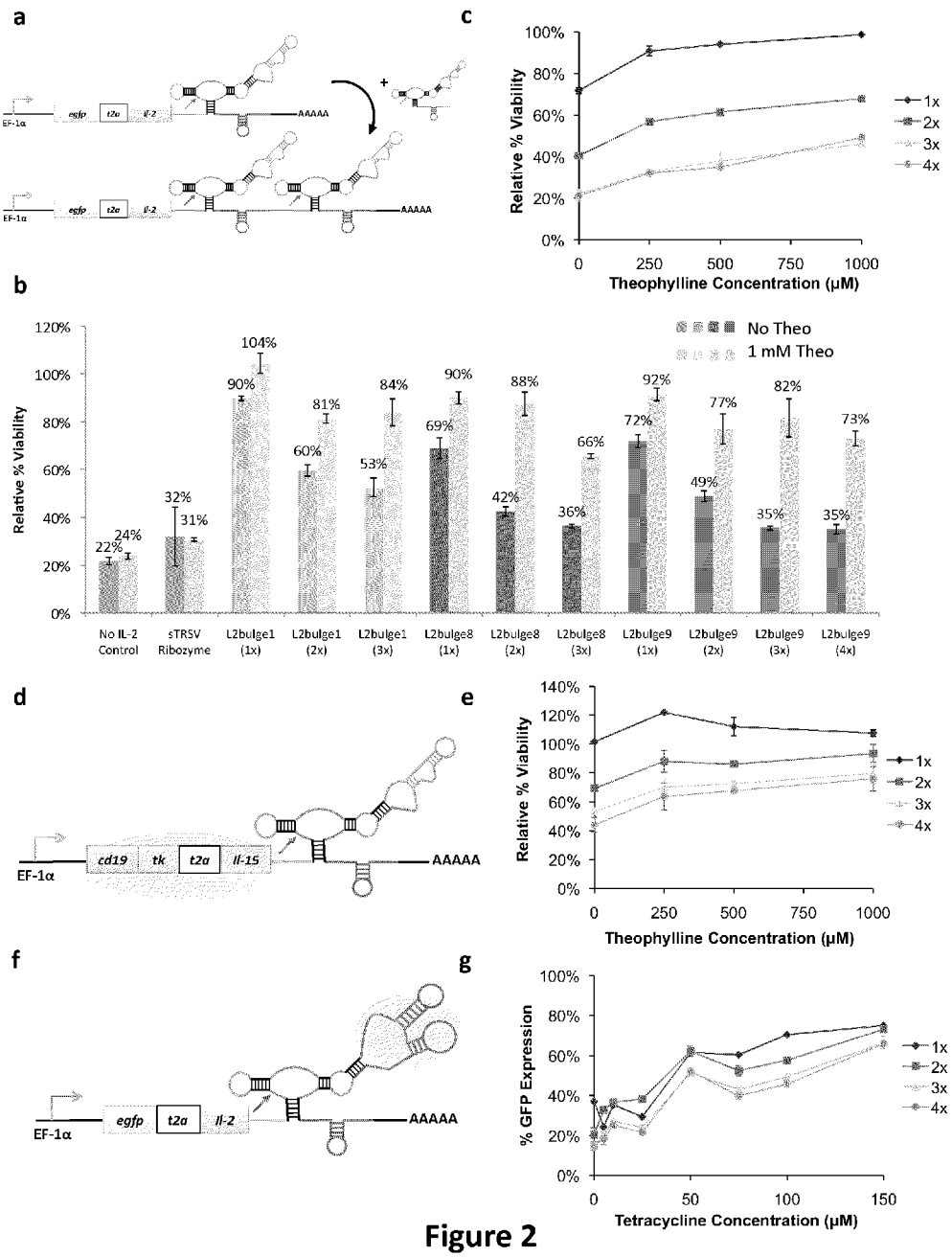

The dynamic range of the theophylline-responsive system is limited by the relatively high toxicity and low cell permeability of the input molecule. However, an important property of the ribozyme-based regulatory system is that its component functions are modular and thus amenable to changes that support customization for diverse applications, such as reprogramming input responsiveness toward clinically usable pharmaceuticals. To verify this critical property of our prototype T-cell proliferation control system, we replaced the theophylline aptamer (Denison, R. D., Gill, S. C., Pardi, A. & Polisky, B. High-resolution molecular discrimination by RNA. *Science* 263, 1425-1429 (1994)) with the tetracycline aptamer (Berens, C., Thain, A. & Schroeder, R. A tetracycline-binding RNA aptamer. *Bioorg Med Chem* 9, 2549-2556 (2001)) to construct a tetracycline-responsive switch (L2bulge18tc; FIG. 2*f*). In vitro culture assays demonstrated tetracycline-responsive ON switch activity in CTLL-2 cells from single- and multiple-copy switch systems (FIG. 2*g*). The tetracycline-responsive systems demonstrated lower basal expression levels and increased dynamic ranges in response to lower input concentrations relative to the theophylline-responsive systems. The tetracycline switch system demonstrates the ability to improve regulatory stringency and increase the switch dynamic range by using aptamers with higher binding affinities and input molecules that can be administered to higher intracellular concentrations. Fluorescence measurements in FIG. 2 are reported for the output of the tetracycline-responsive switch systems, as the toxicity of tetracycline to CTLL-2 cells did not allow for accurate viability measurements. All viability and fluorescence values were normalized to those obtained from CTLL-2 cells transfected with a construct encoding the appropriate transgene regulated by an inactive hammerhead ribozyme cultured at corresponding theophylline concentrations. Reported values are mean±s.d. from at least two replicate samples.

Example 9

Mammalian Cell Culture Maintenance

The mouse T cell line CTLL-2 was obtained from ATCC (Manassas, Va.) and maintained in RPMI-1640 media (Lonza; Basel, Switzerland) supplemented with 10% heat-inactivated fetal bovine serum (Hyclone; Logan, Utah), 2 mM sodium pyruvate (Gibco; Carlsbad, Calif.), and 4.5 g/L D-(−)-glucose (Sigma; St. Louis, Mo.). IL-2 was added to the media every 48 hours to a concentration of 100 U/ml, and cell density was maintained between $0.05 \times 10^6$ cells/ml and $0.50 \times 10^6$ cells/ml. Zeocin (Invivogen; San Diego, Calif.) was added to the media of all CTLL-2 cell lines stably expressing the ffLuc:zeocin fusion gene to a concentration of 0.20 mg/ml. Primary human central memory T ($T_{CM}$) cells were derived from PBMCs (see below for details) and maintained in RPMI-1640 media supplemented with 10% heat-inactivated fetal bovine serum. 50 U/ml IL-2 and 0.5 ng/ml IL-15 were added to the media every 48 hours, and cell density was maintained between $0.2 \times 10^6$ cells/ml and $1.0 \times 10^6$ cells/ml.

Example 10

Primer Sequences

This example provides sequences of nucleic acid primers used in the examples.

TABLE 1

Primer sequences

| Primer Name | DNA Sequence (5' to 3') |
| --- | --- |
| Kozak BamHI5' | SEQ ID NO: 1<br>ATCGGATCCGCCGCCACCATGGAGGATGCCAA<br>GAATATTAAGAAAGG |
| zeocin XbaI3' | SEQ ID NO: 2<br>TATTCTAGATCAGTCCTGCTCCTCTGCCACAA<br>AGTGC |
| CD19t BlpI5' | SEQ ID NO: 3<br>ATTGCTGAGCCTAGAGCTGAAG |
| CD19t-mutsr39TK FR | SEQ ID NO: 4<br>CCCGCAGTAGCGTGGGCATTCTTTTCCTCCTC<br>AGGACCAG |
| CD19t-mutsr39TK FF | SEQ ID NO: 5<br>CTGGTCCTGAGGAGGAAAAGAATGCCCACGCT<br>ACTGCGGG |
| mutsr39TK-T2A FR | SEQ ID NO: 6<br>CCTCTCCGCCGCCAGATCTGTTAGCCTCCCCC<br>ATCTCCC |
| mutsr39TK FF | SEQ ID NO: 7:<br>GGGAGATGGGGAGGCTAACAGATCTGGCGGC<br>GGAGAGG |
| IL15op BsrGI3' | SEQ ID NO: 8:<br>TCTCGGTGTACAGGGTGGCG |
| eGFP KpnI5' | SEQ ID NO: 9:<br>CTTGGTACCCGCCACCATGGTGAGCAAG |
| T2A-IL2 FR | SEQ ID NO: 10:<br>CCACGTCACCGCATGTTAGAAGACTTCCTCTG<br>CCCTCTCCGCTGCCCTTGTACAGCTCGTCCAT<br>GCC |
| T2A-IL2 FF | SEQ ID NO: 11:<br>CTTCTAACATGCGGTGACGTGGAGGAGAATCC<br>CGGCCCTATGTACAGGATGCAACTCCTGTC |
| IL2 XhoI3' | SEQ ID NO: 12:<br>AGACTCGAGTCAAGTTAGTGTTGAGATGATGC |
| CMV HpaI5' | SEQ ID NO: 13:<br>AATAGTTAACGTTGACATTGATTATTGACTAG<br>TTATTAATAGTAATCAA |
| bGHpA SacII3' | SEQ ID NO: 14:<br>AATACCGCGGCCATAGAGCCCACCGC |
| EF1α BglII5' | SEQ ID NO: 15:<br>AATAGATATCTGCTTCGCGAGGATCTGC |
| EF1 α KpnI3' | SEQ ID NO: 16:<br>AATAGGTACCGGTGGCGGCGCTAG |
| Rz XhoI-AsiSI5' | SEQ ID NO: 17:<br>AATACTCGAGGCGATCGCAAACAAACAAA |
| Rz ApaI-PacI3' | SEQ ID NO: 18:<br>AATAGGGCCCAAGATTAATTAAAAAAAAAATT<br>TTTATTTTTCTTTTTGCTGTT |
| Hprt1 reverse | SEQ ID NO: 19:<br>TGCTGCCATTGTCGAACA |

TABLE 1-continued

Primer sequences

| Primer Name | DNA Sequence (5' to 3') |
|---|---|
| IL-15 reverse | SEQ ID NO: 20:<br>GGTGTCGTGGATGCTG |
| Hprt1 forward | SEQ ID NO: 21:<br>AGCCAGCGAAGCCAC |
| IL-15 forward | SEQ ID NO: 22:<br>CAACTGGGTGAACGTGAT |

Example 11

T2A Sequences

SEQ ID NO. 23: T2A DNA sequence
GGCAGCGGAGAGGGCAGAGGAAGTCTTCTAACATGCGGTGACGTGGAGGA

GAATCCCGG

SEQ ID NO. 24: T2A peptide sequence
GSGEGRGSLLTCGDVEENPG

Example 12

Ribozyme Switch Sequences

Scheme: Single underline, catalytic core of the ribozyme or actuator component; double underline, aptamer or sensor component; italicized, spacer sequences.

SEQ ID NO: 25: sTRSV hammerhead ribozyme
5'CTCGAGAAACAAACAAAGCTGTCACCGGATGTGCTTTCCGGTCTGATG

AGTCCGTGAGGACGAAACAGCAAAAAGAAAAATAAAAATTTTTTGGAATC

TAGA

SEQ ID NO: 26: L2bulge1
5'CTCGAGGCGATCGCAAACAAACAAAGCTGTCACCGGATGTGCTTTCCG

GTCTGATGAGTCCGTGTCCATACCAGCATCGTCTTGATGCCCTTGGCAGG

GACGGGACGAGGACGAAACAGCAAAAAGAAAAATAAAAATTTTTTTTTA

ATTAATCTTGGGCCC

SEQ ID NO: 27: L2bulge8
5'CTCGAGGCGATCGCAAACAAACAAAGCTGTCACCGGATGTGCTTTCCG

GTCTGATGAGTCCGTTGTCCATACCAGCATCGTCTTGATGCCCTTGGCAG

GGACGGGACGGAGGACGAAACAGCAAAAAGAAAAATAAAAATTTTTTTT

TAATTAATCTTGGGCCC

SEQ ID NO: 28: L2bulge9
5'CTCGAGGCGATCGCAAACAAACAAAGCTGTCACCGGATGTGCTTTCCG

GTCTGATGAGTCCGTTGTCCAATACCAGCATCGTCTTGATGCCCTTGGCA

GTGGATGGGACGGAGGACGAAACAGCAAAAAGAAAAATAAAAATTTTTT

TTTTAATTAATCTTGGGCCC

SEQ ID NO: 29: L2bulge18tc
5'CTCGAGGCGATCGCAAACAAACAAAGCTGTCACCGGATGTGCTTTCCG

GTCTGATGAGTCCGTTGTCCAAAACATACCAGATTTCGATCTGGAGAGGT

GAAGAATTCGACCACCTGGACGAGGACGGAGGACGAAACAGCAAAAAGAA

AAATAAAAATTAATTAATCTTGGGCCC

SEQ ID NO: 30: Inactive ribozyme
5'CTCGAGGCGATCGCAAACAAACAAAGCTGTCACCGGATGTGCTTTCCG

GTACGTGAGGTCCGTGAGGACAGAACAGCAAAAAGAAAAATAAAAATTTT

TTTTTTAATTAATCTTGGGCCC

Example 13

Transient Transfection and Fluorescence Quantification

All transient transfections into CTLL-2 cells were performed with an Amaxa Nucleofector II and the Mouse T Cell Nucleofector Kit (Amaxa, Gaithersburg, Md.) following the manufacturer's protocols. Electroporations were performed with $2\times10^6$ cells and 3 μg of plasmid DNA. One hour after electroporation, samples were diluted 2 fold with supplemented RPMI media and split into 2 wells, one treated with small molecule input and one without input. In experiments testing a range of input concentrations, multiple aliquots of cells were electroporated as described. One hour after electroporation, samples were combined, diluted 2 fold, split into the appropriate number of wells, and each treated with the appropriate concentration of small molecule input. Fluorescence and cell viability data were obtained 24 and 48 hours after transfection, respectively, using a Quanta Cell Lab Flow Cytometer (Beckman Coulter; Fullerton, Calif.) equipped with a 488-nm laser. EGFP, PE, and dsRed-Express were measured through 525/30-nm band-pass, 575/30-nm band-pass, and 610-nm long-pass filters, respectively. Viability was gated based on side scatter and electronic volume, and only viable cells were included in fluorescence measurements. For samples expressing constructs based on pIL2, viable cells were further gated for dsRed-Express expression, which served as a transfection efficiency control, before EGFP intensity values were collected. All fluorescence measurements were reported as the geometric mean intensity observed in the gated population. To control for toxicity and other possible nonspecific effects of transfection and input ligand molecules, cells transfected with an inactive (scrambled) hammerhead ribozyme and treated with the corresponding concentration of ligand molecule served as positive controls to which values from cells transfected with active ribozyme switches were normalized (see Example 28 for detailed discussion on controls and normalization). The inactive ribozyme constructs provide controls for the maximum possible gene expression levels from the ribozyme-based regulatory systems. CD19 antibody staining was performed by washing $1\times10^6$ cells twice with 500 μl HBSS (Gibco), incubating with 10 μl PE-conjugated CD19 antibody (Beckman Coulter) in 50 μl HBSS for 15 min at 4° C. in the dark, washing twice with 500 μl HBSS, and analyzing on the flow cytometer. Transient transfection experiments were performed with at least two replicate samples, and reported error bars indicate 1 standard deviation from the averaged measured value normalized by the inactive ribozyme control.

Example 14

Stable CTLL-2 Cell Line Generation

To generate a CTLL-2 cell line for in vivo imaging, CTLL-2 cells were electroporated with the pffLuc:zeo plasmid, and stable integrants were selected based on resistance to 0.1 mg/ml zeocin. The stable cell line CffLuc was confirmed through a luciferase activity assay, in which $1 \times 10^4$ cells were resuspended in 100 µl media and aliquoted into 96-well black, clear-bottom plates. Each well was incubated with 20 µl of 1.4 mg/ml D-luciferin diluted in PBS (Xenogen; Palo Alto, Mass.) at 37° C. for 10 min, and luciferase signal was detected using a Victor3 1420 Multilabel Counter (Perkin Elmer; Waltham, Mass.). Signals from 6 replicates were averaged for each experiment, and CTLL-2 cells not expressing ffluc were used as negative controls.

To generate CTLL-2 cells stably expressing constructs encoding the T-cell proliferation regulatory system for in vivo imaging, CffLuc cells were electroporated with plasmids derived from the pIL15 plasmid and linearized at the unique NsiI site. Electroporations for stable cell lines were carried out in 7 cuvettes each containing $5 \times 10^6$ cells and 5 µg plasmid DNA. One hour after electroporation, all electroporated samples were combined, diluted to a total volume of 50 ml, and supplemented with IL-2 every 48 hours to a final concentration of 100 U/ml. Cells were stained with PE-conjugated CD19 antibodies 7 days after electroporation and sorted for PE+ cells by fluorescence-activated cell sorting (FACS) using a BD FACSAria cell sorter (BD Biosciences; San Jose, Calif.) equipped with a 488-nm laser. The sorted cells were grown for 13 days and then stained and further sorted via magnetism-automated cell sorting (MACS) using an autoMACS Separator (Miltenyi Biotec; Germany) for PE+ cells. Theophylline was added to cell cultures to a final concentration of 250 µM 2 days prior to each sort.

Following the FACS and MACS sorts a series of selection cycles were performed by alternating between growth in ganciclovir and theophylline. Cells were grown for 2 weeks following AutoMACS sorting in media supplemented with IL-2 every 48 hours to a final concentration of 100 U/ml. The cells were then grown for 7 days in the presence of 1 µM ganciclovir and supplemented with IL-2 every 48 hours to a final concentration of 100 U/ml. The cells were subsequently placed in fresh media supplemented with 250 µM theophylline and allowed to grow for 4 days in the absence of IL-2. Following termination of theophylline treatment, the cells were placed in fresh media supplemented with 100 U/ml IL-2 (added every 48 hours) and 5 µM ganciclovir for 4 days. The theophylline treatment regime then resumed for 8 days, followed by the ganciclovir treatment regime (at 5 µM) for 10 days, and a final theophylline regime for 5 days. Cell density was maintained between $0.05 \times 10^6$ cells/ml and $0.5 \times 10^6$ cells/ml throughout the cell culture procedure. Following the last theophylline treatment regime, cells were stained with PE-conjugated CD19 antibodies and sorted for single clones into 96-well plates by FACS for low, medium, and high PE levels. The sorted clones (CffLuc-pIL15) were grown in media supplemented with 250 µM theophylline, 50 U/ml penicillin:streptomycin, and no IL-2. Clones were expanded from the low PE fractions into larger culture volumes and finally maintained in T75 tissue culture flasks (BD Falcon; San Jose, Calif.).

Example 15

In vitro Growth Assay for Stable CTLL-2 Cell Lines

CffLuc-pIL15 clones were cultured under regular conditions (RPMI 1640 media supplemented with 100 U/ml IL-2 every 48 hours, 0.2 mg/ml zeocin, no theophylline), washed twice with HBSS, and split into 5 identical aliquots in 6-well plates at approximately $0.01 \times 10^6$ cells/ml (4 ml/well). Each well was supplemented with one of the following: 100 U/ml IL-2, 100 µM theophylline, 250 µM theophylline, 400 µM theophylline, or no IL-2 and no theophylline. Cells were split and passaged as necessary into new 6-well plates at approximately $0.03 \times 10^6$ cells/ml, and IL-2 was added to the appropriate wells to a final concentration of 100 U/ml every 48 hours. Cell count was obtained from 50 µl of each culture daily for 7 days on a Quanta Cell Lab Flow Cytometer by gating for viable cells based on side scatter and electronic volume. Cell density was calculated by dividing the number of detected live cells by the volume analyzed on the flow cytometer.

Example 16

In Vivo T-Cell Proliferation Studies in NOD/SCID-IL12(Ko) Mice

Various CffLuc-pIL15 cell lines, CffLuc, and a CffLuc-derived cell line stably expressing a cytokine fusion transgene with an inactive ribozyme in the 3' UTR of the transgene were expanded under regular culture conditions. Cells were harvested by centrifugation at 1200 rpm at 4° C. for 10 min, washed twice with PBS, resuspended in PBS at a concentration of $2 \times 10^6$ cells/ml, and split into two 50 µl aliquots. Each aliquot was mixed with 50 µl of either PBS or 2 mM theophylline dissolved in PBS. The 100 µl cell suspension was then mixed with 100 µl of Matrigel (BD Biosciences), for a total of $0.1 \times 10^6$ cells at a final concentration of 500 µM theophylline. The cell suspensions were injected subcutaneously (s.c.) into the right or left flank of NOD/scid-IL2(ko) mice. All mice were 8 to 10 weeks old and bred in the City of Hope lab animal breeding facility. In vivo growth of the injected cells was monitored by biophotonic imaging. Clone 1264-48 and the positive control cell line expressing an inactive ribozyme were tested in a second experiment following the procedure described above. Each cell line was injected into both flanks of 3 mice either with or without 500 µM theophylline, generating 6 replicates for each experimental condition. One of the mice injected with clone 1264-48 without theophylline exhibited abnormally large engraftments in both flanks. Additional subjects were studied to verify that cell growth in this mouse was aberrant in a statistically significant manner (P=0.044 based on comparison against 8 other replicates with the same experimental condition), and data from this mouse were excluded from statistical analyses of the ribozyme switch system.

Example 17

Biophotonic In Vivo Imaging

Animals received intraperitoneal (i.p.) injections of 4.29 mg per mouse of freshly prepared luciferin substrate (Caliper Life Sciences; Hopkinton, Mass.) suspended in 150 µl of PBS. Mice were then anesthetized with isoflurane (1.5 L oxygen+4% isoflurane per minute) in an induction chamber. After induction of deep anesthesia, mice were imaged using the IVIS Imaging System 100 Series (Xenogen) consisting of a CCD camera mounted on a light-tight specimen chamber (darkbox), a camera controller, a camera cooling system, and a Windows computer system for data acquisition and analysis. Images were acquired at 10-20 min after luciferin injection with the appropriate exposure time and binning mode to prevent signal saturation. Luciferase activity was analyzed through Living Image Software 3.1 from Xenogen to quantify tumor region flux (photons per second).

Example 18

Statistical Analysis

Statistical analysis was performed on growth rate data using the Mann-Whitney U test to calculate two-tailed P values. The doubling time of injected cells was calculated based on the total luciferase signal flux data collected over the course of each in vivo study. Signal flux data were fitted to an exponential curve, and the resulting equation was used to calculate cell-doubling time using the equation:

$$t_D = (t_2 - t_1)\frac{\log(2)}{\log(F_2 - F_1)},$$

where t is time, F is signal flux, and $t_D$ is doubling time.

Example 19

Plasmid Construction

Figure 14:
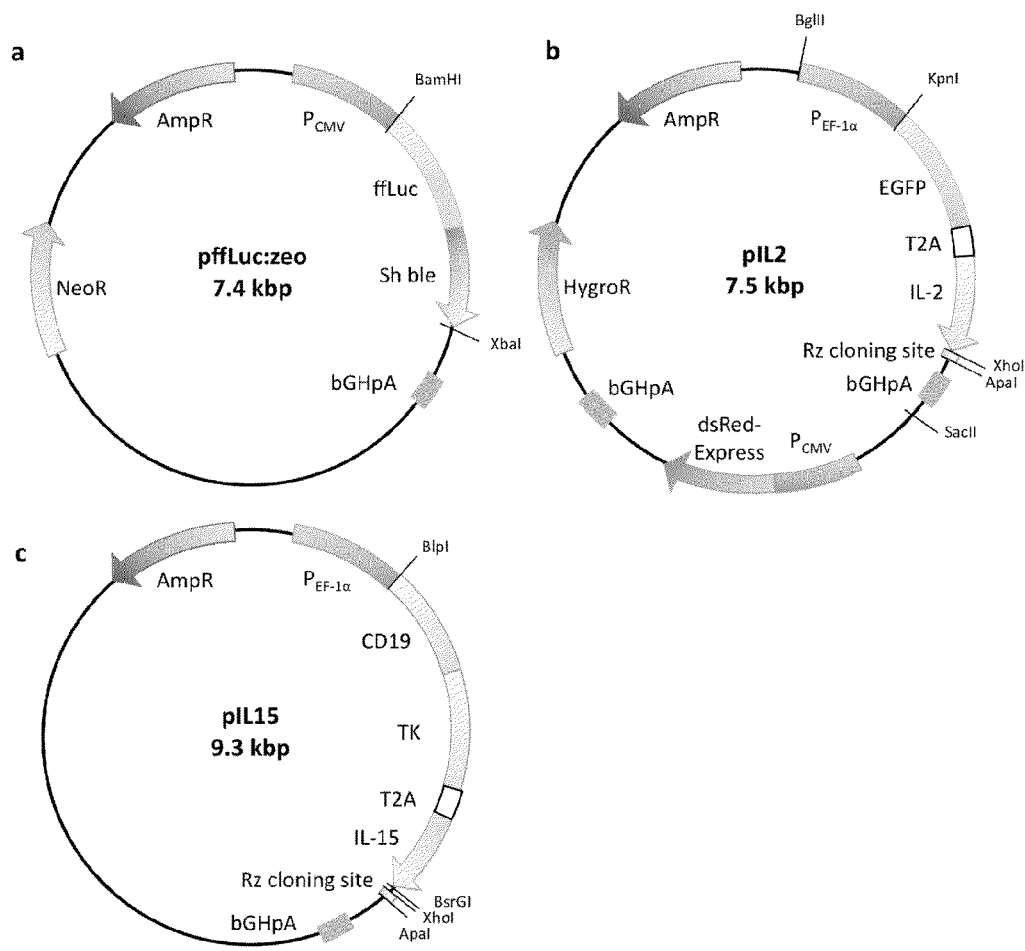
FIG. 14a shows the plasmid map of construct pffLuc:zeo used in generating T cell lines stably expressing firefly luciferase for in vivo imaging.
FIG. 14b shows the plasmid map of T-cell proliferation construct: pIL2.
FIG. 14c shows the plasmid map of T-cell proliferation construct: pIL15.

All plasmids were constructed using standard molecular biology techniques (Sambrook, J. & Russell, D. W. Molecular Cloning: A Laboratory Manual. 3 edn, (Cold Spring Harbor Press, 2001)). All primer sequences are provided in Example 10; plasmid maps are provided in FIG. 14. All oligonucleotides were synthesized by Integrated DNA Technologies (Coralville, Iowa) and all constructs were sequence verified (Laragen, Inc.; Los Angeles, Calif.). Cloning enzymes, including restriction enzymes and T4 DNA ligase, were obtained from New England Biolabs (Ipswich, Mass.) and DNA polymerases were obtained from Stratagene (La Jolla, Calif.).

A fusion of the firefly luciferase (ffluc) gene and the Sh ble gene encoding zeocin resistance was PCR amplified from pMOD-LucSh (Invivogen; San Diego, Calif.) using forward and reverse primers Kozak BamHI5' and zeocin XbaI3', respectively. The plasmid pffLuc:zeo was constructed by inserting the resulting PCR product into pcDNA3.1(+) (Invitrogen; Carlsbad, Calif.) via the unique restriction sites BamHI and XbaI located in the multi-cloning site behind the CMV promoter.

The cd19 gene was PCR amplified from CD19t-Tk-T2A-IL15op_epHIV7 using forward and reverse primers CD19t B1pI5' and CD19t-mutsr39TK FR, respectively. The thymidine kinase gene mutsr39tk was PCR amplified from mutsr39tk_pcDNA3.1(+) using forward and reverse primers CD19t-mutsr39TK FF and mutsr39TK-T2A FR, respectively. The cytokine gene il-15 was PCR amplified from CD19t-Tk-T2A-IL15op_epHIV7 using forward and reverse primers mutsr39TK FF and IL15op BsrGI3', respectively. PCR products for the three genes were assembled via a fourth PCR reaction using forward and reverse primers CD19t B1pI5' and IL15op BsrGI3', respectively. The plasmid pIL15 was constructed by inserting the assembled PCR product (cd19-mutsr39tk-t2a-il15) into CD19t-Tk-T2A-IL15op_epHIV7 via the unique restriction sites BlpI and BsrGI behind the EF1α promoter.

The fluorescence gene egfp was PCR amplified from eGFP_pcDNA3.1(+) using forward and reverse primers eGFP KpnI5' and T2A-IL2 FR, respectively. The cytokine gene il-2 was PCR amplified from IL2pSK using forward and reverse primers T2A-IL2 FF and IL2 XhoI3', respectively. PCR products for the two genes were assembled via a third PCR reaction using forward and reverse primers eGFP KpnI5' and IL2 XhoI3', respectively. The plasmid eGFP-T2A-IL2_pcDNA3.1(+) was constructed by inserting the assembled PCR product (egfp-t2a-il2) into pcDNA3.1(+) via the unique restriction sites KpnI and XhoI behind the CMV promoter. A DNA sequence including the CMV promoter, the egfp-t2a-il2 fusion gene, and the poly-A sequence was PCR amplified from eGFP-T2A-IL2_pcDNA3.1(+) using forward and reverse primers CMV HpaI5' and bGHpA SacII3', respectively. The PCR product was inserted into dsRed Express_pcDNA3.1(+) via the unique restriction sites HpaI and SacII. The CMV promoter regulating the egfp-t2a-il2 fusion gene was replaced by the EF1α promoter via the unique restriction sites BglII and KpnI to construct the plasmid pIL2. The EF1α promoter sequence was PCR amplified from pIL15 using forward and reverse primers EF1α BglII5' and EF1α KpnI3', respectively.

A standardized cloning method was developed to allow for the sequential insertion of engineered ribozyme switches and corresponding control constructs in the 3' UTR of the target transgenes. The engineered ribozyme switch constructs were generated by PCR amplification using the forward primer Rz XhoI-AsiSI5', where the underlined sequences indicate restriction sites for XhoI and AsiSI, respectively, and the reverse primer Rz ApaI-PacI3', where the underlined sequences indicate restriction sites for ApaI and PacI, respectively. The italicized sequences indicate spacers flanking each ribozyme switch, and the 3' spacer sequence forms a hairpin structure consisting of A-U pairs to provide insulation for each ribozyme switch. The first copy of an engineered ribozyme switch in each plasmid (using pIL2 or pIL15 as the plasmid backbone) was inserted via the unique restriction sites XbaI and ApaI. All subsequent copies of the engineered ribozyme switches were inserted behind the 3' end of the previous copy of ribozyme switch by digesting the plasmid with PacI and ApaI and the insert with AsiSI and ApaI, where digestion with PacI and AsiSI result in identical sticky ends. The resulting ligation product retained unique PacI and ApaI sites while eliminating the AsiSI site, thus allowing the cloning strategy to be repeated for each additional copy of the ribozyme switch inserted into the construct.

Example 20

CTLL-2 Time Course Study

CTLL-2 parental cells, clonal stable cell line 1264-48 (L2bulge9(3×)), and clonal stable cell line 1266-3 (inactive ribozyme) were cultured under regular conditions (see Example 9). On day 0, cells were counted for density and washed twice with HBSS. Each cell line was used to seed two 50-ml cultures at $0.15 \times 10^6$ cells/ml (Set 1) and two 50-ml cultures at $0.05 \times 10^6$ cells/ml (Set 2). 500 µM theophylline was added to one flask at each seeding density. 50 U/ml IL-2 was added to Set 1 flasks and 100 U/ml IL-2 was added to Set 2 flasks to keep IL-2 concentration consistent with seeding cell density and harvesting schedule. On day 1, Set 1 flasks were harvested for CD19 antibody staining ($1 \times 10^6$ cells per sample) and for cell pellet collection for qRT-PCR ($12.5 \times 10^6$ cells per sample, washed once with HBSS, and flash frozen with liquid nitrogen). Each culture was split to $0.05 \times 10^6$ cells/ml at 50 ml total and supplemented with 100 U/ml IL-2 and the appropriate concentration of theophylline (0 µM or 500 µM). On day 2, the same harvest and subculture procedures were repeated for Set 2 flasks. All cultures were treated in this manner every 48 hours until day 7. On day 7, cell count was obtained for all cultures. After harvesting from Set 1 flasks, all cultures were washed twice with HBSS and resuspended in fresh media without theophylline. Set 1 flasks were seeded at $0.05 \times 10^6$ cells/ml and supplemented with 100 U/ml IL-2. Set 2 flasks were seeded with all available cells and supplemented with 50 U/ml IL-2. On days 8 and 9, the same harvest and subculture procedures were performed on Set 2 and Set 1 flasks, respectively. All cultures were treated in this manner every 48 hours until day 14. On day 14, cell count was obtained for all cultures. After harvesting from Set 2 flasks, all cultures were washed twice with HBSS and resuspended in fresh media. 500 µM theophylline was added to all cultures that had been treated with theophylline on days 0-7. Set 2 flasks were seeded at $0.05 \times 10^6$ cells/ml and supplemented with 100 U/ml IL-2. Set 1 flasks were seeded with all available cells and supplemented with 50 U/ml IL-2. On days 15 and 16, samples were harvested for CD19 staining and subcultured as before for Set 2 and Set 1 flasks, respectively. All cultures were treated in this manner every 48 hours until day 18.

Example 21

Transcript Analysis through RT-PCR mRNA was purified from frozen cell pellets with the GenElute Direct mRNA MiniPrep Kit (Sigma) following the manufacturer's protocols. mRNA samples were treated with 100 U/ml DNaseI at 37° C. for 15 min and purified by phenol-chloroform extraction and ethanol precipitation. Reverse transcription was performed with 300 ng mRNA, 2 pmol of each primer, 10 nmol dNTP, 40 U RNaseOUT, 5 mM DTT, 1× First-Strand Buffer, and 200 U SuperScript III Reverse Transcriptase (Invitrogen) in a 20 µl reaction following the manufacturer's protocols. Gene-specific primers (Hprt1 reverse, IL-15 reverse) were used in the cDNA synthesis reactions. The resulting cDNA samples were subsequently treated with 2.5 U of RNaseH at 37° C. for 20 min, followed by heat inactivation at 65° C. for 20 min.

qRT-PCR reactions were performed in a 25 µl reaction with 200 nM of each primer, 5 µl DNA, and 1×SYBR Green SuperMix (Bio-Rad) on an iCycler Real-Time PCR machine (Bio-Rad; Hercules, Calif.). Separate reactions were performed for the housekeeping gene Hprt1 (Hprt1 forward, Hprt1 reverse) and the target gene il-15 (IL-15 forward, IL-15 reverse). The qRT-PCR protocol included 32 cycles of a 15 sec annealing step at 50° C. and a 30 sec extension step at 72° C., followed by a melt curve analysis to verify absence of nonspecific products. All reactions were performed in triplicates, and threshold cycle ($C_t$) values were averaged to obtain the arithmetic mean. Relative IL-15 expression levels were calculated with the following formula (Livak, K. J. & Schmittgen, T. D. Analysis of relative gene expression data using real-time quantitative PCR and the 2(-Delta Delta C(T)) Method. Methods 25, 402-408 (2001)):

$$RE = \frac{\varepsilon_{Hprt1}^{(C_{t,Hprt1})}}{\varepsilon_{IL-15}^{(C_{t,IL-15})}}$$

where RE indicates relative IL-15 expression, ε indicates primer efficiency for gene x, and $C_{t,x}$ indicates the averaged $C_t$ value for gene x. Standard deviation was calculated with the following formula:

$$STD = \sqrt{[RE1n(\varepsilon_{Hprt1})]^2(Std_{Hprt1})^2 + [RE1n(\varepsilon_{IL-15})]^2(Std_{IL-15})^2}$$

where STD indicates standard deviation in relative IL-15 expression and $Std_x$ indicates standard deviation calculated from the triplicate samples for gene x. Reported error bars indicate 1 standard deviation.

Example 22

Western Blot Analysis of STAT5 Levels

Clonal stable cell lines were cultured under regular conditions (see above), washed twice with HBSS, and split into two identical aliquots. The aliquots were grown in the absence of IL-2 and either in the presence or absence of 500 µM theophylline for 3 days. Approximately $2 \times 10^6$ cells of each sample were harvested and washed with 1 ml HBSS each day, frozen with liquid nitrogen, and stored at −80° C. until lysis. Cell pellets were lysed with 50 µl Triton-X lysis buffer (1% Triton-X, 10 mM Tris-HCl, pH 7.4, 130 mM NaCl, 5 mM EDTA, protease inhibitor, 5% phosphatase inhibitor cocktail II) and incubated on ice for 1 hour. Lysates were centrifuged at 14,000×g for 20 min at 4° C. The supernatant was collected and immediately frozen at −80° C.

Lysate samples were thawed on ice and a standard Bradford assay using Protein Assay Dye (Bio-Rad) was performed with a BSA standard to determine protein concentrations. Samples were run on NuPAGE 4-12% Bis-Tris Gels (Invitrogen) at 90 V for 2.5 hours, where 50 µg of protein from each sample was loaded. Blotting was performed with Mini Trans-Blot Filter Paper (Bio-Rad) and 0.45 µm Nitrocellulose Membranes (Bio-Rad) wetted with NuPAGE transfer buffer (Invitrogen) and transferred at 40 mA per gel with a Hoefer Semi-Phor Blotter (Hoefer Scientific Instruments; Holliston, Mass.). Membranes were blocked with Odyssey Blocking Buffer (Li-Cor; Lincoln, Nebr.) at 4° C. for 1 hour and probed with Rabbit-anti-pSTAT5 antibody (Cell Signaling; Danvers, Mass.) or IRDye 800CW-conjugated anti-β-actin antibody (Rockland; Gilbertsville, Pa.) at 4° C. overnight in the dark. Membranes probed with p-STAT5 antibodies were washed 4 times with 100 ml TTBS (1× Tris-Buffered Saline (TBS, Bio-RAD), 0.1% Tween 20 (Sigma)) and further stained with IRDye 800CW-conjugated goat-anti-rabbit antibody (Li-Cor) at room temperature for 1 hour. Membranes stained for l3-actin and p-STAT5 were washed 4 times with 100 ml TTBS and once with 100 ml TBS before fluorescent images were acquired and quantified with the Odyssey Infrared Imaging System (Li-Cor). Integrated band intensity was calculated with the Odyssey system using blank gel areas surrounding each band for background subtraction. Relative p-STAT5 expression levels were calculated by normalizing the integrated intensity of the p-STAT5 band by that of the β-actin band from the same protein sample. Data shown are representative of two independent experiments.

Example 23

Lentivirus Production $5.0 \times 10^6$ 293T cells were seeded in a final volume of 9 ml per 10-cm tissue culture plate and transfected with 1 ml solution containing vector DNA, 62 mM $CaCl_2$, and 1×HBS. Cells were washed twice with 5 ml 1×PBS without magnesium and calcium the following morning and fed 10 ml of complete DMEM with 60 mM sodium butyrate. At 24-, 48-, and 72-hours post transfection, viral supernatants were harvested by centrifugation at 2,000 rpm for 10 min at 4° C. and filtered through 0.45 µM vacuum filtration unit. Viral supernatants from all time points were pooled and mixed with ¼ volume of 40% PEG. After rotating overnight at 4° C., samples were centrifuged at 3,000 rpm for 20 min at 4° C. and the supernatants discarded. Pellets were resuspended in 35 ml serum-free DMEM and ultracentrifuged at 24,500 rpm for 1.5 hours at 4° C. Resulting pellets were resuspended in 50 µl serum-free FBS and vortexed at 4° C. for 2 hours. 10% FBS was added and the samples stored at −80° C. until tittering and use.

Example 24

Derivation of Central Memory T ($T_{CM}$) Cells from Human Peripheral Blood Mononuclear Cells (PBMCs)

$5 \times 10^8$ PBMCs were isolated from donor apheresis products, washed twice with 35 ml MACS buffer (2 mM EDTA and 0.5% BSA in PBS), resuspended in 1.5 ml MACS buffer. Washed cells were stained with 0.75 ml each of CD4, CD14, and CD45RA microbeads (Miltenyi Biotec; Germany), and depleted for CD4, CD14, and CD45RA using an autoMACS Separator (Miltenyi). Depleted cells were washed once with 35 ml MACS buffer, resuspended in 3.5 ml MACS buffer with 10.5 µl anti-CD62L DREG56-biotin antibody (City of Hope Center for Biomedicine and Genetics; Duarte, Calif.), and incubated for 20 min in the dark at 4° C. Cells were washed twice with 35 ml MACS buffer and resuspended in 1.2 ml MACS buffer with 300 µl anti-biotin microbeads (Miltenyi). Cells were enriched for CD62L using an autoMACS Separator, placed in fresh RPMI 1640 media supplemented with 10% FBS and stored in 37° C. incubator.

Example 25

Lentiviral Transduction of $T_{cM}$ Cells $0.5 \times 10^6$ $T_{CM}$ cells were seeded in a total volume of 500 µl per well in 48-well plate. $1.5 \times 10^6$ Anti-CD3/anti-CD28 Dynabeads (Invitrogen) were washed with 1% heat-inactivated human serum in PBS (pH 7.4), resuspended in 500 µl T-cell media (RPMI 1640 supplemented with 10% heat-inactivated fetal bovine serum) containing $0.5 \times 10^6$ $T_{CM}$ cells, and added to each of 2 wells in a 48-well plate. Each well was fed with 50 U/ml IL-2 and 0.5 ng/ml IL-15, infected with viruses at a multiplicity of infection (MOI) of 5, and treated with protamine sulfate at a final concentration of 5 µg/ml. The plate was centrifuged at 2100 rpm for 30 min at 32° C. and incubated at 37° C. for 4 hours. 500 µl of warm T-cell media was added to each well and the plate was incubated at 37° C. Cells were assayed by flow cytometry on day 8 post transduction and Dynabeads were removed on day 14 post transduction.

Example 26

$T_{CM}$ Cell CD19 Expression Time-Course Study $T_{CM}$ cells transduced with the cd19-t2a-il15-L2bulge9(3x) or cd19-t2a-il15-inactive ribozyme constructs were stimulated with $100 \times 10^6$ PBMCs, $10 \times 10^6$ TM-LCLs, and 30 ng/ml OKT2 for each T75 flask and cultured under regular conditions for 12 days. On day 12 post stimulation, each cell line was used to seed four 25-ml cultures at $0.2 \times 10^6$ cells/ml. 500 µM theophylline was added to 2 flasks of each cell line, and no IL-2 or IL-15 was fed to any flask. Two aliquots from each culture were sampled every 24 hours for staining with PE-conjugated CD19 antibody (Beckman Coulter; Fullerton, Calif.). Fluorescence data were obtained with a Quanta Cell Lab Flow Cytometer using a 488-nm laser and a 575/30-nm band-pass filter. Percent CD19 expression was calculated by measuring the CD19 expression level of CD19+ gated cells and normalizing results of the L2bulge9(3x) sample by those of the inactive ribozyme sample cultured at the same theophylline concentration.

Example 27

$T_{CM}$ Cell Apoptosis Time-Course Study $T_{CM}$ cells transduced with the cd19-t2a-il15-L2bulge9(3x) or cd19-t2a-il15-inactive ribozyme constructs were stimulated as described above. On day 12 post stimulation, each cell line was washed twice with HBSS and used to seed six 25-ml cultures at $0.45 \times 10^6$ cells/ml. 500 µM theophylline was added to 3 flasks of each cell line, and no IL-2 or IL-15 was fed to any flask. 500 µl of each culture was sampled every 24 hours for antibody staining with PE-conjugated CD19 antibody followed by viability staining with Pacific Blue-conjugated annexin V and SYTOX AAD dead cell stain (Invitrogen) following manufacturer's protocols. Fluorescence data were obtained using a Quanta Cell Lab Flow Cytometer with both a 488-nm laser and an UV arc lamp. Pacific Blue, PE, and SYTOX AAD were detected through 465/30-nm band pass, 575/30-nm band pass, and 610-nm long pass filters, respectively, Only SYTOX AAD-cells were included in data analyses. The population of live CD19+ cells was determined by gating for annexin V−/PE+ cells and the population of apoptotic CD19+ cells was determined by gating for annexin V+/PE+ cells. Relative population distribution was calculated by normalizing results of the L2bulge9(3x) sample to those of the inactive ribozyme sample cultured at the same theophylline concentration.

Example 28

Controlling for Toxicity and Nonspecific Effects of Nucleofection and Small Molecule Ligand Inputs on Growth and Gene Expression Like most T cell lines, CTLL-2 cells cannot be effectively transfected by lipid-based transfection reagents. Therefore, electroporation with Amaxa Nucleofector technology is the method of choice for transfecting CTLL-2 cells. The trauma of nucleofection results in high cell mortality and affects the health of surviving cells. To account for the toxicity of nucleofection, all experiments conducted with CTLL-2 cells included as a positive control cells nucleofected with a similar DNA construct harboring an inactive, scrambled ribozyme that lacks an attached aptamer. This control construct has no ribozyme-based knockdown activity, no ligand-responsive cleavage activity, and represents the maximum possible expression level from the regulatory system. Viability and fluorescence data from all other samples were reported relative to those of the positive control treated with the same concentration of small molecule ligand, as it has been verified by multiple nucleofection experiments that nucleofection toxicities from similar DNA constructs purified in the identical manner are similar.

Figure 5:
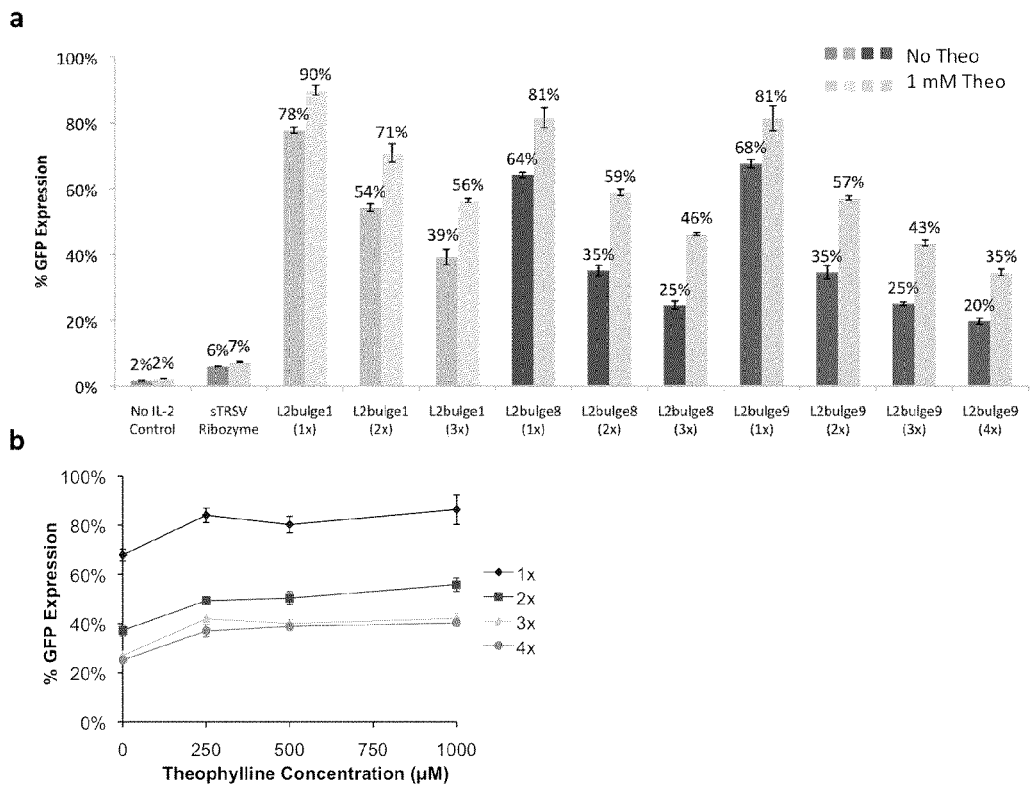
FIG. 5a shows GFP expression levels for constructs encoding theophylline-responsive switches (L2bulge1, 8, 9) in one (1×), two (2×), three (3×), and four (4×) copies through transient transfections in CTLL-2 cells grown in 0 (left bar of the pairs) and 1 mM theophylline (right bar of the pairs).
FIG. 5b shows GFP expression levels for multiple-copy L2bulge9 regulatory systems at various theophylline concentrations.
Figure 15:
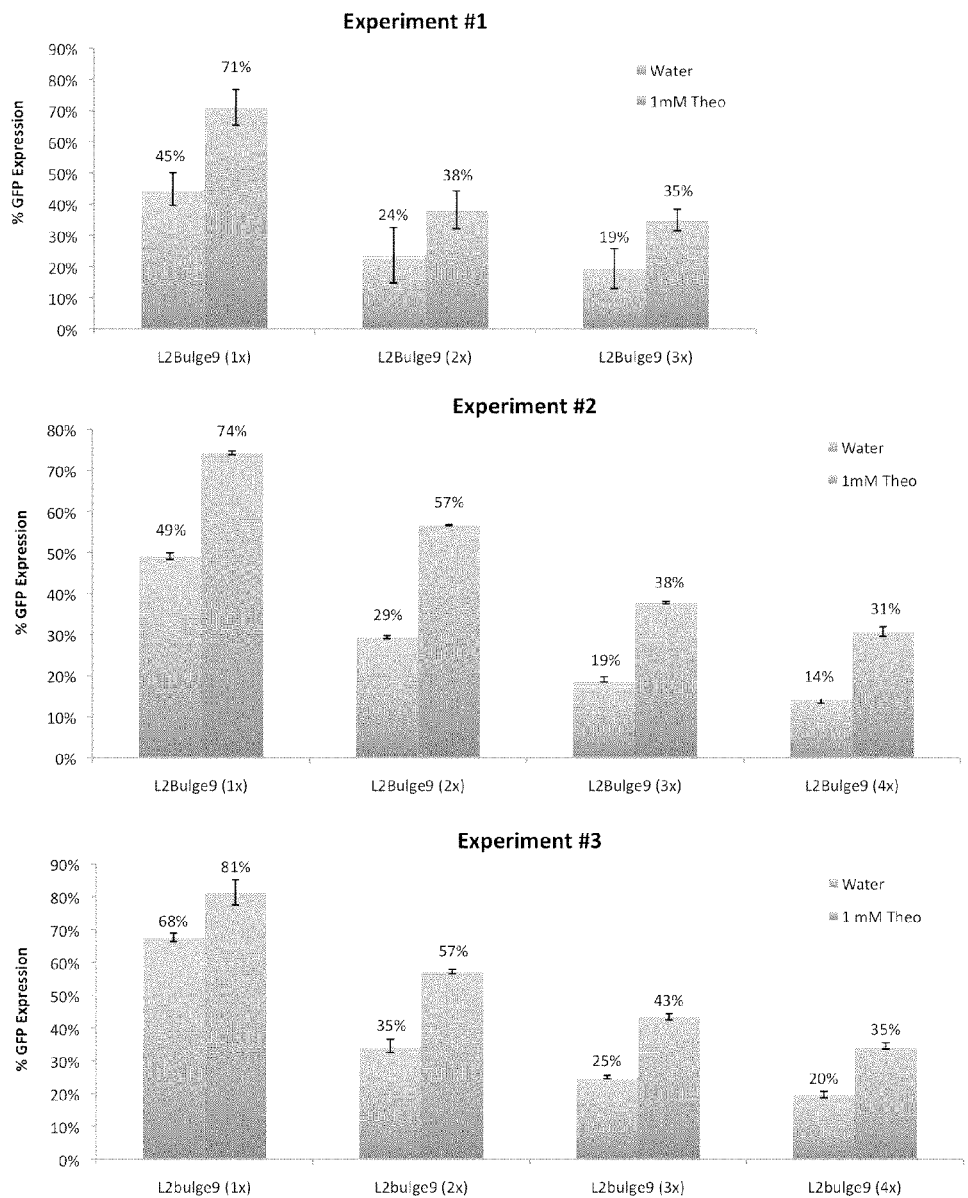
FIG. 15 shows the expression of GFP in three independent transient transfection experiments on different days in the presence (right bar of the pairs) or absence of theophylline (left bar of the pairs).
Figure 16:
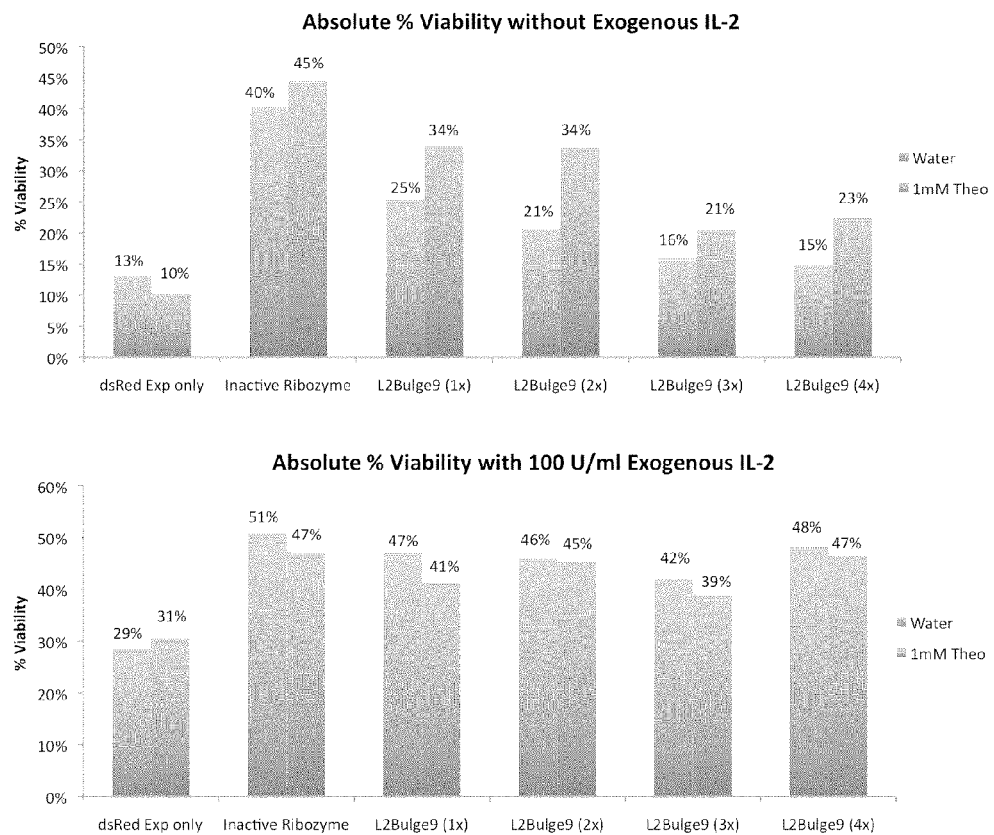
FIG. 16 shows the absolute viability (viable population as percent of total population) of CTLL-2 cells transiently transfected with ribozyme-based regulatory systems as measured by flow cytometry in the presence (left bar of the pairs) and absence of theophylline (right bar of the pairs).
Figure 17:
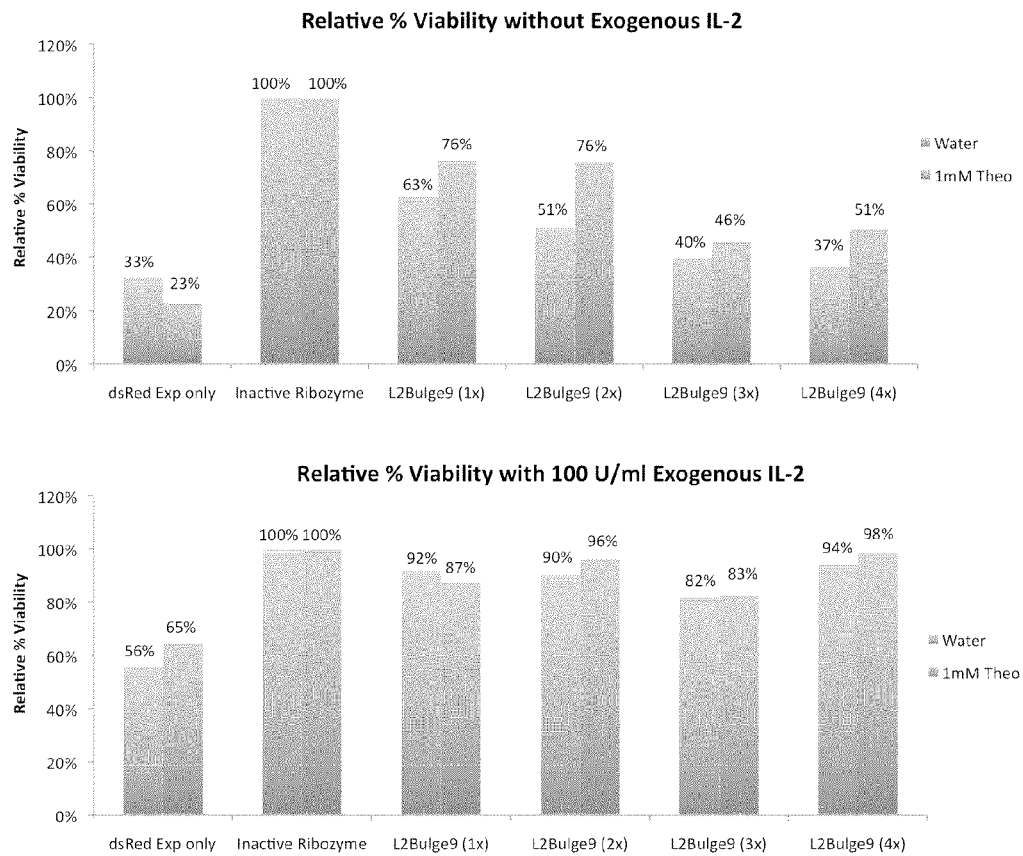
FIG. 17 shows the relative viability (absolute viability of test sample normalized by absolute viability of inactive ribozyme control) of CTLL-2 cells transiently transfected with ribozyme-based regulatory systems in the presence (left bar of the pairs) and absence of theophylline (right bar of the pairs).

The reproducible agreement between two characterization methods—viability (a phenotypic response) and fluorescence (a measure of reporter gene expression)—provided further confirmation of ligand-responsive gene regulatory activity (FIGS. 2 and 5). To verify that the different viability and fluorescence levels observed from the various ribozyme switch constructs are not due to random variations in nucleofection toxicity, multiple transfection experiments were performed on different days and consistent results were observed (FIG. 15). Reproducible results support that the observed regulatory activity is specific to the regulatory system. Fluorescence values shown in FIG. 15 were normalized. Values are mean±s.d. from at least two replicate samples. To further verify that growth cytokine withdrawal (and not nucleofection toxicity) is responsible for the decrease in viability levels observed for cells transfected with active ribozyme switch constructs, transfected samples were split into two identical aliquots, one of which was fed with 100 U/ml of exogenous IL-2. The IL-2-treated samples had significantly higher viability levels compared to identical samples not treated with exogenous IL-2, both in absolute terms (FIG. 16) and relative to the inactive ribozyme control (FIG. 17). FIG. 16 shows that the presence of exogenous IL-2 elevates viability in all samples and abolishes the inverse correlation between viability and ribozyme switch copy number observed in the absence of exogenous IL-2. These results suggests that the reduced viability at high switch copy numbers observed in the absence of exogenous IL-2 is specifically caused by more efficient knockdown of the cytokine transgene encoded by the regulatory system and the resultant cytokine withdrawal. Furthermore, the inverse correlation between viability and ribozyme switch copy number disappears in the presence of exogenous IL-2, suggesting that the reduced viability at high switch copy numbers is specifically caused by more efficient gene expression knockdown and the resultant cytokine withdrawal in the absence of exogenous IL-2.

Figure 18:
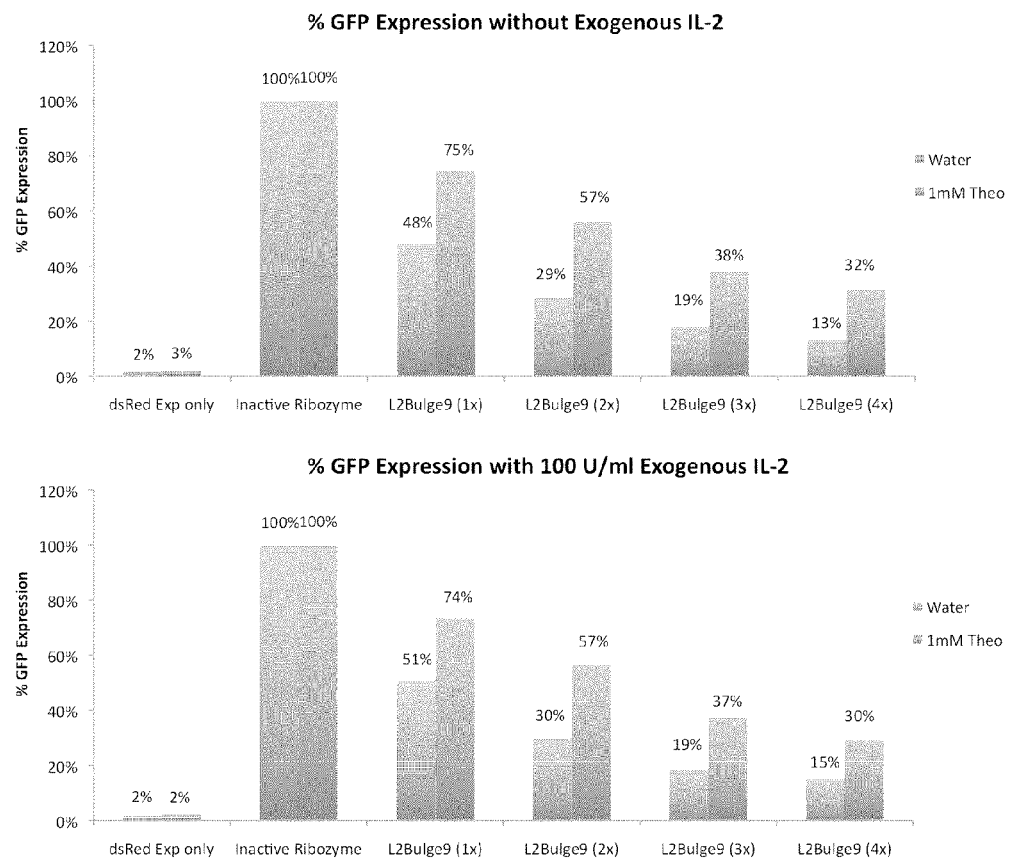
FIG. 18 shows normalized GFP expression levels in CTLL-2 cells transiently transfected with ribozyme-based regulatory systems in the presence (left bar of the pairs) and absence of theophylline (right bar of the pairs).

In contrast, the addition of exogenous IL-2 does not affect fluorescence levels (FIG. 18). The samples shown in FIG. 17 are identical to those in FIG. 18, and the trends match those observed in the absolute viability data. In contrast to viability behaviors shown in FIGS. 16 and 17, switch activity as measured by fluorescence and shown in FIG. 18 is unaffected by the presence of exogenous IL-2, indicating that the gene expression modulation is specific to the regulatory system. Taken together, these results indicate that the observed variations in viability levels are specific to the regulatory systems.

Figure 19:
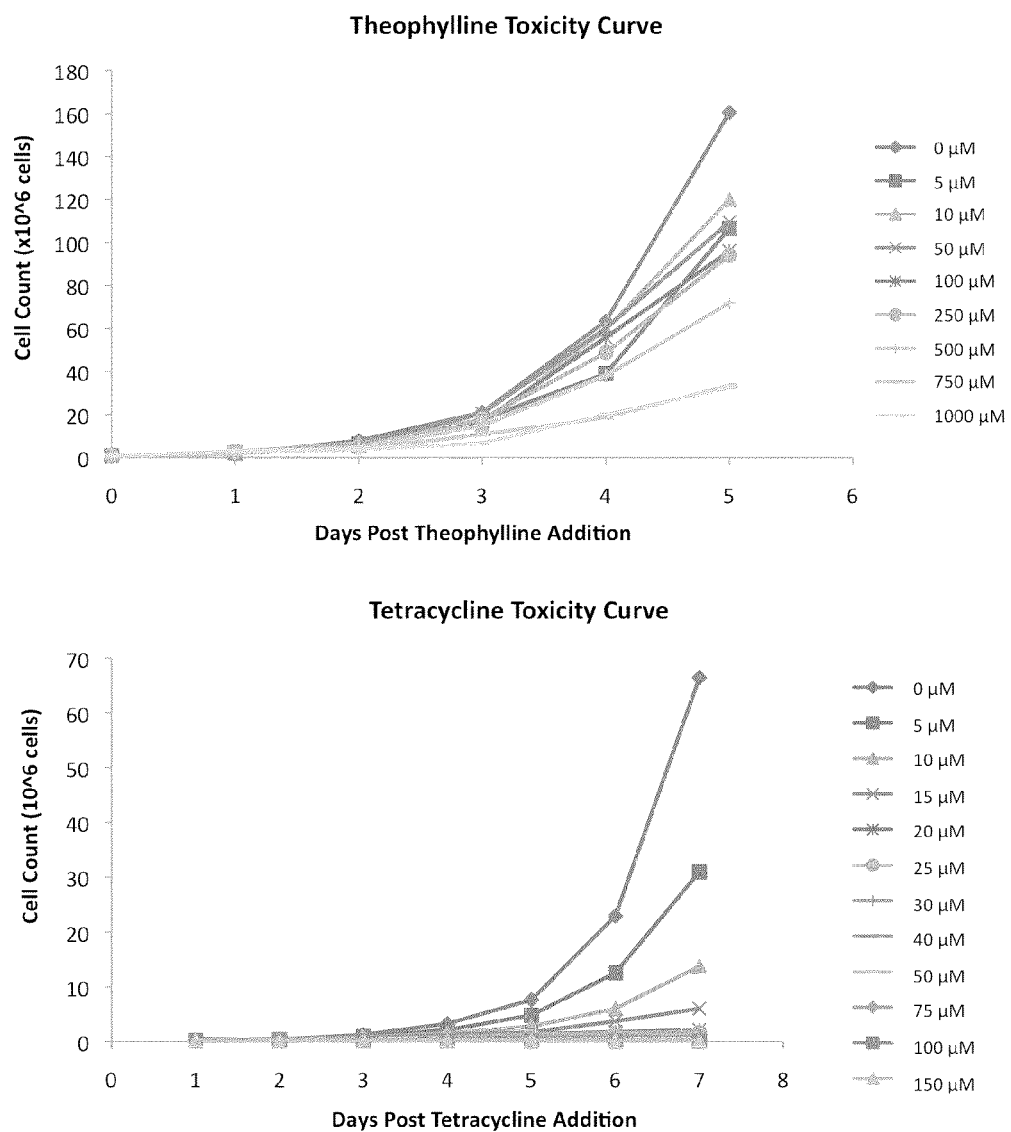
FIG. 19 shows small molecule toxicity curves for CTLL-2 cells. Cells were cultured in media containing the indicated concentration of (a) theophylline and (b) tetracycline.

The toxicity and potential pleiotropic effects of the small-molecule ligands theophylline and tetracycline were also considered. Theophylline and tetracycline both exhibit some toxicity to CTLL-2 cells (FIG. 19). In the experiment shown in FIG. 19, 100 U/ml of IL-2 was fed to all cultures every 48 hours, and cell count was obtained every 24 hours by flow cytometry. In transient transfection experiments the fluorescence and viability values of all samples were normalized to that of the inactive ribozyme control treated with the same concentration of the small molecule ligand (as described above) to account for non-aptamer-mediated effects of the ligand, as it is assumed that the nonspecific effects of the ligand will be similar for the sample and the control. Negative controls, such as cells transfected with vectors that encode either no growth cytokine or a growth cytokine gene coupled to a fully active, non-switch hammerhead ribozyme control (sTRSV), were included in all transient transfection experiments. The relative viability and fluorescence levels from the negative control samples exhibited no response to ligand addition, indicating that the normalization method adequately accounts for the toxicity and pleiotropic effects of the small molecule ligands (FIGS. 2b and 5a).

By using the inactive ribozyme as the normalizing control for all switch constructs, we report the regulatory output of the switches relative to the maximum possible expression range. Compared to the more commonly used method of internal normalization, where each switch construct is normalized to its own internal high value, our method has the effect of reducing the apparent dynamic range of each switch. However, the reporting of switch output to a consistent standard control allows for direct and accurate comparison of the various switches, which is important for system development and characterization.

Figure 7:
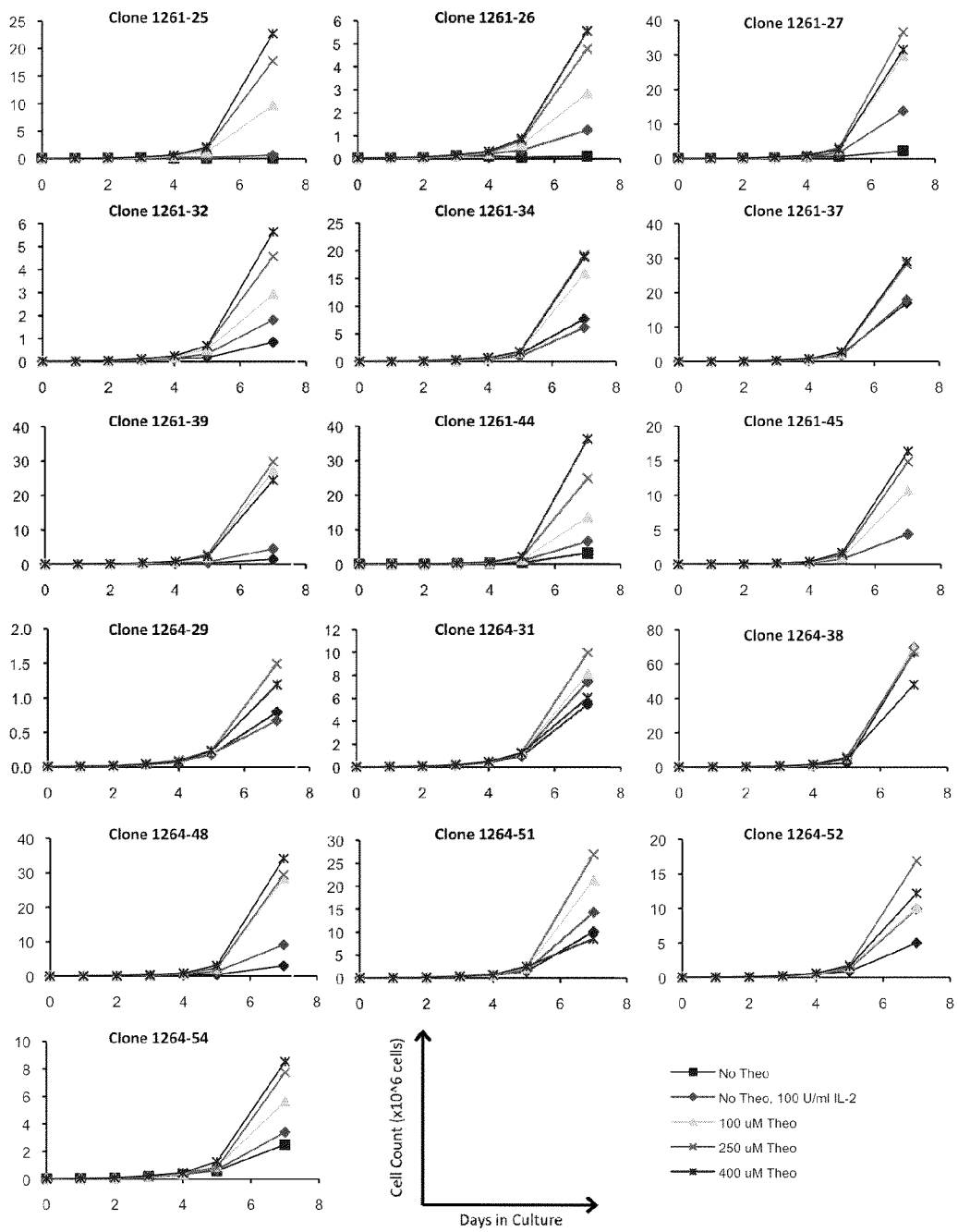
FIG. 7 shows graphs of cell count for various clonal CTLL-2 cell lines stably expressing engineered ribozyme switch systems over a range of theophylline concentrations.
Figure 20:
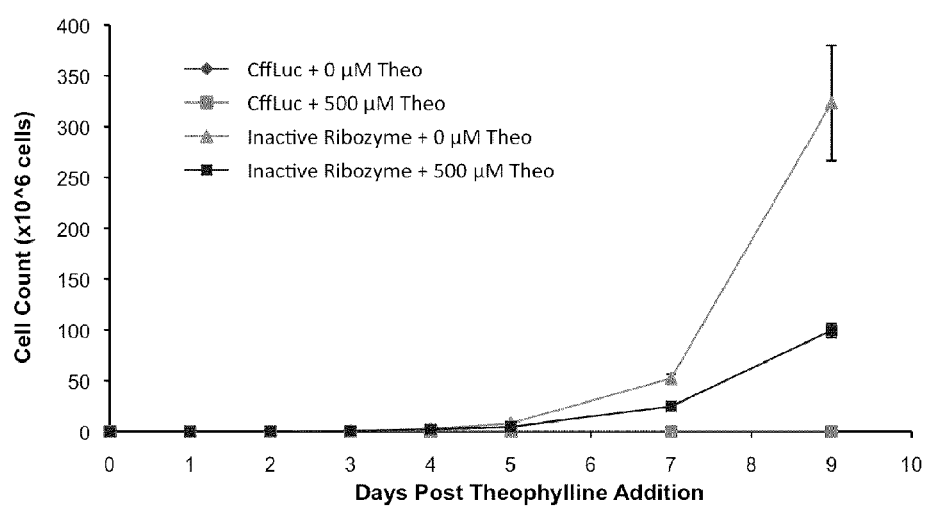
FIG. 20 shows the growth (measured by cell count) of CffLuc cells and a clonal cell line stably expressing the inactive ribozyme cultured in the presence or absence of 500 µM theophylline without exogenous IL-2.

In the characterization of cell lines stably expressing the ribozyme switch constructs, a clonal cell line expressing the positive control construct (inactive ribozyme) was included to identify any nonspecific effects of theophylline. As an example, an in vitro growth assay was performed on clonal cell lines in the presence or absence of 500 µM theophylline. The cell line expressing the inactive ribozyme exhibited a decreased growth rate in the presence of theophylline (FIG. 20), indicating theophylline toxicity and verifying that the theophylline-induced increase in absolute growth rate observed from clones expressing the active ribozyme switches were not due to any nonspecific growth-stimulatory effects of theophylline (FIGS. 3b and 7). As another example, positive and negative control cell lines were included in the animal studies and no significant theophylline-dependent differences were observed in the in vivo growth pattern of cells that either do not express growth cytokines or express the inactive ribozyme control (FIGS. 4a and 4c). In contrast, the in vitro and in vivo growth rates of clonal cell lines expressing functional ribozyme switch systems show increases in absolute growth rate (not normalized to the inactive ribozyme control) in response to theophylline addition (FIGS. 3b, 4b, 7, 11). Taken together, these results indicate that the observed T-cell growth behaviors were specific to the ligand-responsive regulatory system.

While the present teachings have been described in terms of these exemplary embodiments, the skilled artisan will readily understand that numerous variations and modifications of these exemplary embodiments are possible without undue experimentation. All such variations and modifications are within the scope of the current teachings.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

EQUIVALENTS

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A nucleic acid that encodes: (a) a gene product that affects a cell fate decision of a lymphocyte, and (b) two or more copies of an RNA switch nucleic acid domain, each comprising a sensor domain and an actuator domain, wherein the sensor domain is configured to bind to theophylline and the actuator domain modulates expression of the gene product; wherein binding of theophylline to the sensor domain modulates the functional activity of the actuator domain modulating the expression of the gene product, thereby providing control over basal expression level of the gene product, wherein the sensor domain is encoded by a sequence comprising L2bulge9 (SEQ ID NO: 28).

2. The nucleic acid of claim 1, wherein the nucleic acid encodes three or more copies of the RNA switch nucleic acid domain, and wherein the sensor domains of each RNA switch nucleic acid domain bind to theophylline independently.

3. The nucleic acid of claim 1, wherein the cell fate decision is T-cell activation, proliferation, apoptosis or differentiation.

4. The nucleic acid of claim 1, wherein the actuator domain is a ribozyme.

5. The nucleic acid of claim 4, wherein the ribozyme is a hammerhead ribozyme.

6. The nucleic acid of claim 4, wherein the ribozyme is located in the 3' untranslated region of the gene product.

7. The nucleic acid of claim 6, wherein the ribozyme cleaves the 3' untranslated region in the absence of theophylline.

8. The nucleic acid of claim 6, wherein the ribozyme cleaves the 3' untranslated region in the presence of theophylline.

9. The nucleic acid of claim 1, wherein the gene product is a cytokine receptor, or a cytokine-cytokine receptor fusion protein.

10. The nucleic acid of claim 1, wherein the gene product is a cytokine.

11. The nucleic acid of claim 10, wherein the cytokine is IL-2, IL-4, IL-7, IL-9 or IL-15.

12. The nucleic acid of claim 1, wherein the nucleic acid further encodes a fluorescent protein.

13. The nucleic acid of claim 1, wherein the nucleic acid further encodes a safety protein that kills a host cell comprising said system, in the presence of a drug or a prodrug.

14. The nucleic acid of claim 1, wherein the gene product is a T-cell receptor targeting a tumor-associated antigen.

15. The nucleic acid of claim 14, wherein the T-cell receptor targeting the tumor-associated antigen is patient-derived, or is synthetic.

16. The nucleic acid of claim 13, wherein the safety protein is a thymidylate kinase, or CD20.

17. A lymphocyte comprising the nucleic acid of claim 1.

18. The nucleic acid of claim 1, wherein the nucleic acid that encodes the gene product is a multi-gene transgene.

19. The lymphocyte of claim 17, further comprising a nucleic acid encoding a receptor for a tumor-associated antigen.

20. A method of affecting the proliferation or activation of a T cell in a mammal, the method comprising: providing to the mammal, a mammalian cell comprising the nucleic acid of claim 1.

21. The method of claim 20, further comprising providing to the mammal an effective amount of theophylline to affect proliferation or activation of the T cell.

* * * * *